(12) United States Patent
Souda et al.

(10) Patent No.: US 9,475,828 B2
(45) Date of Patent: Oct. 25, 2016

(54) ORGANOPOLYSILOXANE AND USE THEREOF AS SURFACTANT, POWDER TREATMENT AGENT, THICKENING AGENT OF OIL-BASED RAW MATERIAL OR GELLING AGENT, GEL AND EMULSION COMPOSITIONS, AS WELL AS, PREPARATIONS FOR EXTERNAL USE AND COSMETICS COMPRISING THE SAME

(75) Inventors: Tatsuo Souda, Ichihara (JP); Seiki Tamura, Ichihara (JP); Tomohiro Iimura, Sodegaura (JP); Akito Hayashi, Ichihara (JP); Sayuri Sawayama, Ichihara (JP); Haruhiko Furukawa, Chiba (JP)

(73) Assignee: DOW CORNING TORAY CO., LTD., Chiyoda-Ku, Tokyo (JP)

( * ) Notice: Subject to any disclaimer, the term of this patent is extended or adjusted under 35 U.S.C. 154(b) by 872 days.

(21) Appl. No.: 13/643,666

(22) PCT Filed: Apr. 28, 2011

(86) PCT No.: PCT/JP2011/060799
§ 371 (c)(1),
(2), (4) Date: Apr. 11, 2013

(87) PCT Pub. No.: WO2011/136393
PCT Pub. Date: Nov. 3, 2011

(65) Prior Publication Data
US 2013/0210930 A1 Aug. 15, 2013

(30) Foreign Application Priority Data
Apr. 30, 2010 (JP) .................. 2010-105896

(51) Int. Cl.
| | | |
|---|---|---|
| C07F 7/00 | (2006.01) | |
| C07F 7/08 | (2006.01) | |
| A61K 8/891 | (2006.01) | |
| A61K 8/892 | (2006.01) | |
| A61Q 1/00 | (2006.01) | |
| A61Q 19/00 | (2006.01) | |
| C08G 77/06 | (2006.01) | |
| C08G 77/14 | (2006.01) | |
| C08G 77/16 | (2006.01) | |
| C08L 83/06 | (2006.01) | |
| C08G 77/50 | (2006.01) | |
| A61K 8/02 | (2006.01) | |

(52) U.S. Cl.
CPC .......... *C07F 7/0849* (2013.01); *A61K 8/0241* (2013.01); *A61K 8/891* (2013.01); *A61K 8/892* (2013.01); *A61Q 1/00* (2013.01); *A61Q 19/00* (2013.01); *C08G 77/06* (2013.01); *C08G 77/14* (2013.01); *C08G 77/16* (2013.01); *C08G 77/50* (2013.01); *C08L 83/06* (2013.01); *A61K 2800/624* (2013.01); *A61K 2800/651* (2013.01)

(58) Field of Classification Search
CPC .. C07F 7/0849; A61K 8/0241; A61K 8/892; A61K 8/891; C08G 77/50; C08G 77/14
USPC ........................... 424/401; 514/772; 556/453
See application file for complete search history.

(56) References Cited

U.S. PATENT DOCUMENTS

| | | | |
|---|---|---|---|
| 4,431,789 | A | 2/1984 | Okazaki et al. |
| 4,698,178 | A | 10/1987 | Hüttinger et al. |
| 4,980,167 | A | 12/1990 | Harashima et al. |
| 5,628,989 | A | 5/1997 | Harashima et al. |
| 5,654,362 | A | 8/1997 | Schulz, Jr. et al. |
| 5,891,977 | A | 4/1999 | Dietz et al. |
| 5,939,478 | A | 8/1999 | Beck et al. |
| 5,981,680 | A | 11/1999 | Petroff et al. |
| 6,051,216 | A | 4/2000 | Barr et al. |
| 6,238,656 | B1 | 5/2001 | Morita et al. |
| 6,280,748 | B1 | 8/2001 | Morita et al. |
| 7,001,971 | B2 | 2/2006 | Nakanishi |
| 7,482,419 | B2 | 1/2009 | Caprasse et al. |
| 7,612,051 | B2 | 11/2009 | Kamei et al. |
| 7,649,087 | B2 | 1/2010 | Yoshitake et al. |
| 7,771,709 | B2 | 8/2010 | Nakanishi et al. |
| 8,288,498 | B2 | 10/2012 | Hayashi et al. |
| 8,592,547 | B2 | 11/2013 | Sakuta et al. |
| 2002/0131947 | A1 | 9/2002 | Nakanishi |
| 2007/0207176 | A1 | 9/2007 | Kamei et al. |

(Continued)

FOREIGN PATENT DOCUMENTS

| | | |
|---|---|---|
| DE | 112008000839 T5 | 2/2010 |
| EP | 0879840 A2 | 11/1998 |

(Continued)

OTHER PUBLICATIONS

English language abstract for JP 50-004199; Jun. 10, 2015, 1 page.

(Continued)

*Primary Examiner* — Porfirio Nazario Gonzalez
(74) *Attorney, Agent, or Firm* — Howard & Howard Attorneys PLLC

(57) ABSTRACT

The present invention provides a co-modified organopolysiloxane having a specified chemical structure in which a sugar alcohol-modified group and a silylalkyl group having a siloxane dendron structure, and optionally a long-chain hydrocarbon group are present. The co-modified organopolysiloxane is blended, as a surfactant, a powder treatment agent, a gelling agent or the like, or as a cosmetic raw material together with powder (s), oil agent (s) or the like, in a preparation for external use, and in particular, a cosmetic.

26 Claims, No Drawings

(56) References Cited

U.S. PATENT DOCUMENTS

| | | |
|---|---|---|
| 2008/0311060 A1 | 12/2008 | Sakuta et al. |
| 2010/0113731 A1 | 5/2010 | Hayashi et al. |
| 2013/0177516 A1 | 7/2013 | Tamura et al. |
| 2014/0371330 A1 | 12/2014 | Hayashi et al. |
| 2015/0080480 A1 | 3/2015 | Tamura et al. |

FOREIGN PATENT DOCUMENTS

| | | |
|---|---|---|
| EP | 0976775 A2 | 2/2000 |
| EP | 1031592 A2 | 8/2000 |
| EP | 1327668 A1 | 7/2003 |
| EP | 2492333 A1 | 8/2012 |
| JP | 50-004199 A | 1/1975 |
| JP | 57149290 A | 9/1982 |
| JP | 61-090732 A | 5/1986 |
| JP | 61-293903 A | 12/1986 |
| JP | 62-068820 A | 3/1987 |
| JP | 63-139106 A | 6/1988 |
| JP | 2243612 A | 9/1990 |
| JP | 05-186596 A | 7/1993 |
| JP | 06-157236 A | 6/1994 |
| JP | 07-041417 A | 2/1995 |
| JP | 08-012524 A | 1/1996 |
| JP | 08-012546 A | 1/1996 |
| JP | 8012545 A | 1/1996 |
| JP | 09-071504 A | 3/1997 |
| JP | 09-241511 A | 9/1997 |
| JP | 10-036219 A | 2/1998 |
| JP | 2719303 B2 | 2/1998 |
| JP | 10-167946 A | 6/1998 |
| JP | 11-193331 A | 7/1999 |
| JP | 2000-044579 A | 2/2000 |
| JP | 2000038450 A | 2/2000 |
| JP | 2000063225 A | 2/2000 |
| JP | 2000-072784 A | 3/2000 |
| JP | 2000281523 A | 10/2000 |
| JP | 2001512164 A | 8/2001 |
| JP | 2002038013 A | 2/2002 |
| JP | 2002-119840 A | 4/2002 |
| JP | 2002179798 A | 6/2002 |
| JP | 2003146991 A | 5/2003 |
| JP | 2005042097 A | 2/2005 |
| JP | 2007532754 A | 11/2007 |
| JP | 2008-115358 A | 5/2008 |
| JP | 2008274241 A | 11/2008 |
| WO | WO 9906473 A1 | 2/1999 |
| WO | WO 2005100444 A1 | 10/2005 |
| WO | WO 2008123318 A1 | 10/2008 |
| WO | WO 2011/136394 A1 | 11/2011 |
| WO | WO 2011/136397 A1 | 11/2011 |

OTHER PUBLICATIONS

English language abstract and machine-assisted English translation for JP 2000-044579 extracted from the PAJ database on Jun. 10, 2015, 30 pages.

English language abstract and machine-assisted English translation for JP 2000-072784 extracted from the PAJ database on Jun. 10, 2015, 33 pages.

English language abstract for JP 2008-115358 extracted from espacenet.com database on Jun. 10, 2015, 2 pages.

Chemical Sampling Information of Decamethylcyclopentasiloxane (US Dept of Labor, OSHA, updated Jun. 22, 2006).

English language abstract not available for DE 112008000839; however, see English language equivalent U.S. Pat. No. 8,288,498. Original Document extracted from the espacenet.com database on Feb. 20, 2013, 25 pages.

English language abstract for EP 0879840 extracted from the espacenet.com database on Feb. 20, 2013, 15 pages.

English language abstract for JP 2243612 extracted from espacenet.com database on Feb. 20, 2013, 10 pages.

English language abstract and machine-assisted English translation for JP 05-186596 extracted from the PAJ database on Feb. 19, 2013, 52 pages.

English language abstract and machine-assisted English translation for JP 06-157236 extracted from the PAJ database on Feb. 19, 2013, 26 pages.

English language abstract and machine-assisted English translation for JP 07-041417 extracted from the PAJ database on Feb. 19, 2013, 30 pages.

English language abstract and machine-assisted English translation for JP 08-012524 extracted from the PAJ database on Feb. 20, 2013, 28 pages.

English language abstract for JP 8012545 extracted from the espacenet.com database on Feb. 20, 2013, 7 pages.

English language abstract and machine-assisted English translation for JP 08-012546 extracted from the PAJ database on Feb. 20, 2013, 26 pages.

English language abstract and machine-assisted English translation for JP 09-071504 extracted from the PAJ database on Feb. 19, 2013, 29 pages.

English language abstract and machine-assisted English translation for JP 09-241511 extracted from the PAJ database on Feb. 20, 2013, 31 pages.

English abstract and machine-assisted English translation for JP 10-036219 extracted from the PAJ database on Feb. 20, 2013, 35 pages.

English language abstract for JP 10-167946 extracted from the PAJ database on Feb. 20, 2013, 27 pages.

English language abstract for JP 11-193331 extracted from the espacenet.com database on Feb. 20, 2013, 15 pages.

English language abstract for JP 57149290 extracted from the espacenet.com database on Feb. 19, 2013, 12 pages.

English language abstract for JP 61-293903 extracted from the PAJ database on Feb. 19, 2013, 13 pages.

English language abstract for JP 62-068820 extracted from the PAJ database on Feb. 19, 2013, 4 pages.

English language abstract for JP 63-139106 extracted from the PAJ database on Feb. 19, 2013, 9 pages.

English language abstract for JP 2000038450 extracted from the espacenet.com database on Feb. 20, 2013, 13 pages.

English language abstract for JP 2000063225 extracted from the espacenet.com database on Feb. 20, 2013, 17 pages.

English language abstract for JP 2000281523 extracted from the espacenet.com database on Feb. 20, 2013, 24 pages.

English language abstract not available for JP 2001512164; however see English language equivalent U.S. Pat. No. 6,051,216. Original document extracted from the espacenet.com database on Feb. 20, 2013, 69 pages.

English language abstract for JP 2002038013 extracted from the espacenet.com database on Feb. 20, 2013, 19 pages.

English language abstract and machine-assisted English translation for JP 2002-119840 extracted from the PAJ database on Feb. 19, 2013, 25 pages.

English language abstract for JP 2002179798 extracted from the espacenet.com database on Feb. 20, 2013, 27 pages.

English language abstract for JP 2003146991 extracted from the espacenet.com database on Feb. 20, 2013, 11 pages.

English language abstract for JP 2005042097 extracted from the espacenet.com database on Feb. 19, 2013, 59 pages.

English language abstract not available for JP 2007532754; however, see English language equivalent U.S. Pat. No. 7,482,419. Original document extracted from the espacenet.com database on Feb. 20, 2013, 39 pages.

English language abstract for JP 2008274241 extracted from the espacenet.com database on Feb. 20, 2013, 25 pages.

Machine-assisted English translation for JP 2719303 extracted from the PAJ database on Feb. 20, 2013, 23 pages.

English language abstract for WO 2008123318 extracted from the espacenet.com database on Feb. 20, 2013, 40 pages.

International Search Report for Application No. PCT/JP2011/060799 dated Sep. 5, 2011, 4 pages.

International Search Report for Application No. PCT/JP2011/060800 dated Oct. 11, 2011, 4 pages.

International Search Report for Application No. PCT/JP2011/060803 dated Sep. 23, 2011, 3 pages.

ORGANOPOLYSILOXANE AND USE THEREOF AS SURFACTANT, POWDER TREATMENT AGENT, THICKENING AGENT OF OIL-BASED RAW MATERIAL OR GELLING AGENT. GEL AND EMULSION COMPOSITIONS, AS WELL AS, PREPARATIONS FOR EXTERNAL USE AND COSMETICS COMPRISING THE SAME

RELATED APPLICATIONS

This application is the National Stage of International Patent Application No. PCT/JP2011/060799, filed on Apr. 28, 2011, which claims priority to and all the advantages of Japanese Patent Application No. 2010-105896, filed on Apr. 30, 2010, the content of which is incorporated herein by reference.

TECHNICAL FIELD

The present invention relates to a novel organopolysiloxane having both a hydrophilic group and a siloxane dendron structure. In particular, the present invention relates to a surfactant, an emulsion composition, a powder treatment agent, a thickening agent for an oil-based raw material, a gelling agent, a gel composition, and a cosmetic raw material comprising the aforementioned organopolysiloxane, as well as a preparation for external use comprising the same, and in particular, a cosmetic.

BACKGROUND ART

A silicone having a hydrophilic group has superior surface activity power because of possessing both a silicone moiety exhibiting properties such as a hydrophobic property, flexibility, a lubricating property, chemical stability and the like, and a hydrophilic-group moiety exhibiting properties such as a hydrophilic property, a moisture-retaining property, an adhesive property and the like. For this reason, the silicones having hydrophilic groups are widely used in food, resins, paint, cosmetics and the like. In particular, in a cosmetic, a silicone oil such as a low-molecular cyclosiloxane or the like is blended in order to improve sensation during use in many cases. It has been proposed that as a cosmetic raw material such as a surfactant or the like, for example, a polyether-modified silicone is used due to good miscibility with a silicone oil in many cases (JP-A-S61-293903 and the like).

However, a polyether group is sometimes insufficient in view of a hydrophilic property. For this reason, a (poly)glycerol-modified silicone and the application thereof to a cosmetic have been proposed in order to improve the hydrophilic property (see JP-A-S57-149290, JP-A-H06-157236, JP-A-H09-071504 and JP-A-2005-042097). However, the hydrophilic property may be still insufficient even in the case of using the (poly)glycerol group. In order to further enhance hydroxyl-group density, a sugar-modified silicone using a sugar or a polysaccharide as a polyhydric alcohol, and the application thereof to a cosmetic have been proposed (see JP-A-S62-068820, JP-A-S63-139106, JP-A-H05-186596, JP-A-H07-041417, JP-A-2002-119840, JP-A-2008-274241 and JP-A-2002-179798).

On the other hand, an oil agent used in a cosmetic is not restricted to a silicone oil, and various types of oil agents such as a hydrocarbon oil, an ester oil and the like or a mixture thereof are used. For this reason, a material having surface activity power which is superior in miscibility with respect to various types of oil agents, an emulsifying property, stability of the emulsion and the like has been desired. The sugar alcohol-modified silicones described in JP-A-S62-068820, JP-A-S63-139106, JP-A-H05-186596, JP-A-H07-041417, JP-A-2002-119840, JP-A-2008-274241 and JP-A-2002-179798 have the characteristic of a sugar alcohol group which is rich in a hydrophilic property, but the surface-active effect thereof is still restrictive. A surfactant which can stably emulsify various types of oil agents containing not only a silicone oil, but also an organic oil has been desired.

In addition, the aforementioned sugar alcohol-modified silicone has problems described below.

JP-A-S62-068820 and JP-A-S63-139106 indicate a sugar alcohol-modified silicone in which a sugar alcohol residue is bound to a silicone via an amino group, and an application thereof to a cosmetic. However, the sugar alcohol-modified silicone obtained by the aforementioned method contains an amino group, and for this reason, the usages thereof are restricted. For example, for use in a cosmetic, the sugar alcohol-modified silicone is restrictly applied a hair cosmetic due to skin irritation.

JP-A-H05-186596 indicates examples of a sugar alcohol-modified silicone in which a sugar alcohol residue is bound to a silicone via an oxygen atom. However, JP-A-H05-186596 merely describes simple evaluation results of miscibility with an oil agent and an emulsifying property, and fails to describe a blending example in a cosmetic or the blending effects thereof. In addition, there is no description about the molecular structure therefor, and the evaluation results are also insufficient in view of effects of emulsifying various oil agents. In addition, JP-A-H05-186596 merely describes that the sugar alcohol-modified silicone may be applied to a cosmetic, and fails to describe detailed formulation effects.

JP-A-H07-041417 describes examples in which a sugar alcohol-modified silicone having a sugar alcohol residue bound to a silicone via an oxygen atom is applied to a hair cosmetic. However, JP-A-H07-041417 merely describes effects as a hair cosmetic, and fails to clarify the miscibility with oil agents and blending effects.

JP-A-2002-119840 describes an example in which a sugar alcohol-modified silicone having a sugar alcohol bound to a silicone via an intermediate binding chain is applied as a surfactant. However, JP-A-2002-119840 describes a method for producing the aforementioned sugar-modified silicone, but fails to sufficiently describe the structure of the organosilicon compound which is a silicone component or the detailed functions thereof. In addition, the evaluation for emulsifying ability thereof is extremely restricted.

In addition, in a sugar alcohol-modified silicone described in JP-A-2008-274241, the structure of the silicone component is specified, but evaluation results of emulsifying with a silicone oil are merely described, and there is no description regarding an emulsifying property or compatibility with other oil agents or no description regarding a blending example in a cosmetic or blending effects.

In addition, JP-A-2002-179798 describes a silicone modified with a polyhydric alcohol covering a sugar alcohol and the application thereof to a cosmetic. The aforementioned polyhydric alcohol-modified silicone contains branches derived from linear silicone chains in a molecule, and for this reason, miscibility with a silicone oil may be improved. Even if, miscibility with a silicone oil can be enhanced by introducing the linear silicone chains, it is difficult to enhance miscibility with widely-ranged organic oil agents such as a hydrocarbon oil, an ester oil and the like. Use of the aforementioned polyhydric alcohol-modified silicone as a surfactant is insufficient in view of emulsifying widely-ranged oil agents and stability of the emulsions. In addition, the obtained emulsions impart a strong oily feeling on touch, and therefore, are insufficient emulsions.

On the other hand, a sugar alcohol-modified silicone having a siloxane dendron structure is proposed (JP-A-2003-146991). Although the aforementioned sugar alcohol-modified silicone is superior in view of a hydrophilic property since the sugar alcohol group is present at the terminal of the molecule, it is difficult to sufficiently exhibit properties of the siloxane dendron structure since the sugar alcohol group binds to the siloxane dendron structure. Therefore, the aforementioned sugar alcohol-modified silicone is inferior in view of affinity and miscibility with various types of oil agents. In addition, JP-A-2003-146991 merely describes that the sugar alcohol-modified silicone can be applied to a cosmetic and fails to describe detailed formulation effects thereof.

As described above, in conventional sugar alcohol-modified silicones, insufficient miscibility with widely-ranged oil agents is exhibited. For this reason, a surfactant exhibiting a superior emulsifying property and superior stability of an emulsion has been desired. In addition, an emulsion obtained by the aforementioned surfactant, which has a wide application range and exhibits superior storage stability, has been desired.

As application examples of the silicones having hydrophilic groups, mention may be made of, in addition to a surfactant, a powder treatment agent for modifying conditions of the surface of inorganic powders or organic powders by effectively coating the surface thereof, a powder which has been subjected to a surface treatment with the aforementioned powder treatment agent, a mixture between a powder treatment agent and a powder, and a composition in which the silicones are dispersed in an oil agent such as a silicone oil, a hydrocarbon oil, an ester oil or the like. However, in the application of the polyhydric alcohol-modified silicone containing a sugar alcohol to a cosmetic, JP-A-2002-179798 describes an example of a cosmetic composition containing a powder, but fails to describe a dispersing property of the powder, and the effects thereof are insufficient. In addition, JP-A-2002-038013 describes an example of using a silicone having an alcoholic hydroxyl group in a powder treatment, but merely describes modification with a (poly)glycerol group, and fails to indicate effects due to a sugar alcohol group.

DISCLOSURE OF INVENTION

Technical Problems

The present invention has been made in view of the circumstances of the aforementioned prior art. The objective of the present invention is to provide a novel organopolysiloxane in which a rich hydrophilic property is exhibited, not only superior miscibility with a hydrophilic component, but also a hydrophobic property are exhibited, and superior miscibility with both a silicone oil and a non-silicone oil such as a hydrocarbon oil, an ester oil or the like can be exhibited, and provide various usages of the aforementioned novel organopolysiloxane by developing the superior characteristics thereof such as good surface activity power, a distinctive sensation during use, increased stability and the like.

Technical Solution

The objective of the present invention can be achieved by a co-modified organopolysiloxane represented by the following general formula (1):

  (1)

wherein
$R^1$ represents a monovalent organic group, with the proviso that $R^2$, $L^1$ and Q are excluded therefrom;
$R^2$ represents a substituted or non-substituted, and linear or branched monovalent hydrocarbon group having 9 to 30 carbon atoms, or a linear organosiloxane group represented by the following general formula (2-1):

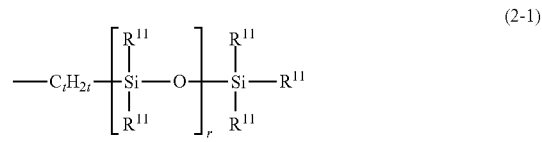  (2-1)

wherein $R^{11}$ is a substituted or non-substituted monovalent hydrocarbon group having 1 to 30 carbon atoms, a hydroxyl group or a hydrogen atom, and at least one $R^{11}$ is the aforementioned monovalent hydrocarbon group; t is the number ranging from 2 to 10; and r is the number ranging from 1 to 500,
or represented by the following general formula (2-2):

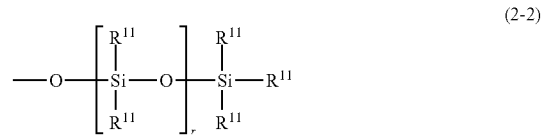  (2-2)

wherein $R^{11}$ and r are the same as defined above;
$L^1$ represents a silylalkyl group having a siloxane dendron structure, in the case of i=1, represented by the following general formula (3):

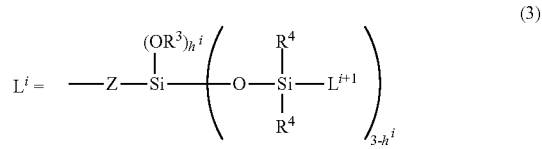  (3)

wherein
$R^3$ represents a substituted or non-substituted, and linear or branched monovalent hydrocarbon group having 1 to 30 carbon atoms;
$R^4$ independently represents an alkyl group having 1 to 6 carbon atoms or a phenyl group;
Z represents a divalent organic group;
i specifies the number of generations of the aforementioned silylalkyl group, represented by $L^i$, in the case in which the number of generations of the aforementioned silylalkyl group, which is the number of repetitions of the aforementioned silylalkyl group, is k, i is an integer ranging from 1 to k, and the number of generations k is an integer ranging from 1 to 10;
$L^{i+1}$ is the aforementioned silylalkyl group in the case of i<k, and $L^{i+1}$ is $R^4$ in the case of i=k; and $h^i$ is the number ranging from 0 to 3;
Q represents an organic group containing a sugar alcohol group; and
each of a, b, c and d is independently the number having the following range: $1.0 \leq a \leq 2.5$, $0 \leq b \leq 1.5$, $0.0001 \leq c \leq 1.5$, and $0.0001 \leq d \leq 1.5$.

In the aforementioned general formula (1), the monovalent organic group, which is $R^1$, preferably represents a substituted or non-substituted, and linear or branched monovalent hydrocarbon group having 1 to 8 carbon atoms, a polyoxyalkylene group represented by the following formula: $-R^5O(AO)_nR^6$ wherein AO represents an oxyalkylene group having 2 to 4 carbon atoms; $R^5$ represents a substituted or non-substituted, and linear or branched divalent hydrocarbon group having 3 to 5 carbon atoms; $R^6$ represents a hydrogen atom, a substituted or non-substituted, and linear or branched monovalent hydrocarbon group having 1 to 24 carbon atoms, or a substituted or non-substituted, and linear or branched acyl group having 2 to 24 carbon atoms; and n=1 to 100, an alkoxy group, a hydroxyl group or a hydrogen atom, with the proviso that all R's do not represent a hydroxyl group, a hydrogen atom, the aforementioned alkoxy group or the aforementioned polyoxyalkylene group.

In the aforementioned general formula (1), Q is preferably an organic group containing a sugar alcohol group represented by the following general formula (4-1):

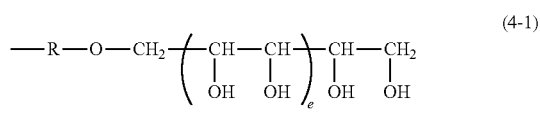
(4-1)

wherein R represents a divalent organic group; and e is 1 or 2, or represented by the following general formula (4-2):

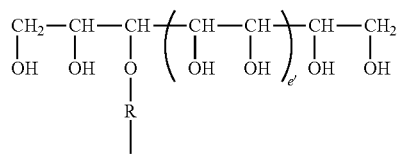
(4-2)

wherein R is the same as defined above; and e' is 0 or 1.

In the aforementioned general formula (4-1) or (4-2), the divalent organic group, which is R, is preferably a substituted or non-substituted, and linear or branched divalent hydrocarbon group having 3 to 5 carbon atoms.

In the aforementioned general formula (1), the silylalkyl group having a siloxane dendron structure, represented by $L^1$, is preferably a functional group represented by the following general formula (3-1):

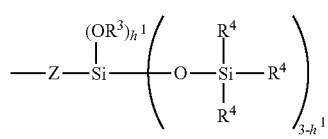
(3-1)

or represented by the following general formula (3-2):

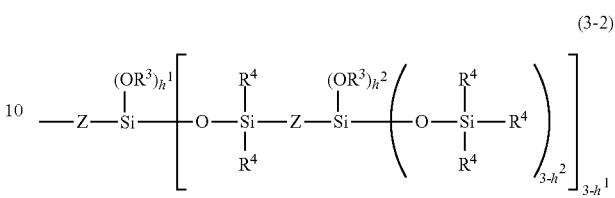
(3-2)

wherein $R^3$, $R^4$ and Z are the same as defined above; and each of $h^1$ and $h^2$ is independently the number ranging from 0 to 3.

The co-modified organopolysiloxane of the present invention is preferably represented by the following structural formula (1-1):

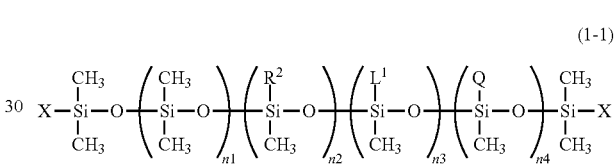
(1-1)

wherein $R^2$, $L^1$ and Q are the same as defined above;

X is a group selected from the group consisting of a methyl group, $R^2$, $L^1$ and Q;

each of n1, n2, n3 and n4 is independently the number ranging from 0 to 2,000, and n1+n2+n3+n4 is the number ranging from 0 to 2,000, with the proviso that in the case of n3=0, at least one X is $L^1$, and in the case of n4=0, at least one X is Q.

The co-modified organopolysiloxane of the present invention is more preferably represented by the following structural formula (1-1-1):

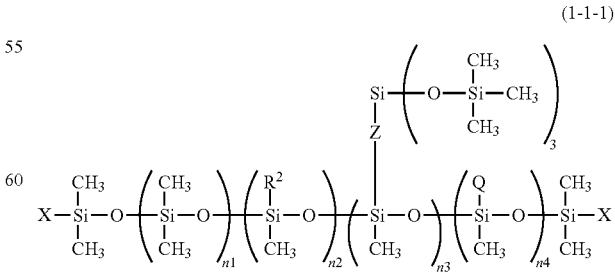
(1-1-1)

wherein $R^2$, Q, X, Z, n1, n2, n3 and n4 are the same as defined above, or represented by the following structural formula (1-1-2):

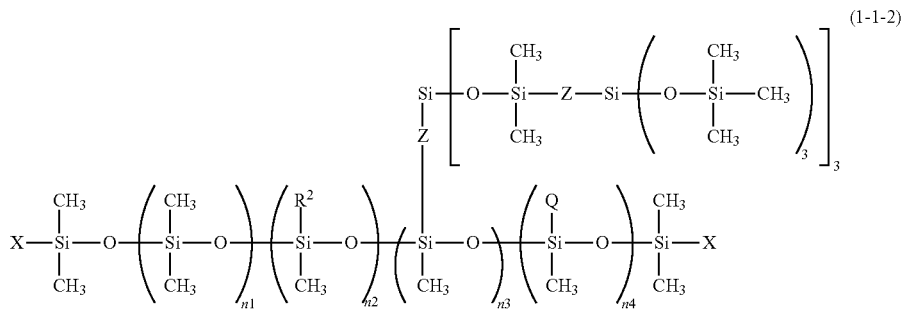

wherein $R^2$, Q, X, Z, n1, n2, n3, and n4 are the same as defined above.

Z is independently and preferably a group selected from divalent organic groups represented by the following general formulae:

—$R^7$—

—$R^7$—CO—

—$R^7$—COO—$R^8$—

—CO—$R^7$—

—$R^7$—COO—$R^8$—

—$R^7$—CONH—$R^8$—

—$R^7$—$R^8$— wherein
each $R^7$ independently represents a substituted or non-substituted, and linear or branched, alkylene or alkenylene group having 2 to 22 carbon atoms or an arylene group having 6 to 22 carbon atoms;
$R^8$ is a group selected from the group consisting of the following groups:

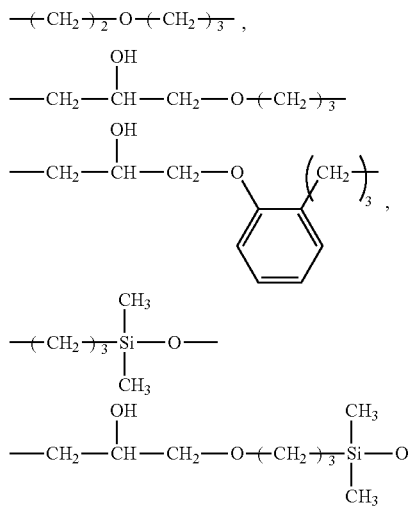

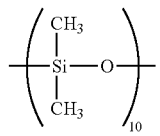

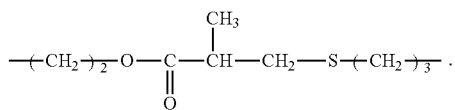

The co-modified organopolysiloxane of the present invention can be used as a surfactant. Therefore, the aforementioned (A) co-modified organopolysiloxane can constitute an emulsion composition together with (B) water and (C) at least one oil agent, which is in the form of a liquid at 5 to 100° C., and is selected from the group consisting of a silicone oil, a non-polar organic compound and a low-polar organic compound.

The aforementioned co-modified organopolysiloxane can be used as a powder treatment agent, and in particular, a powder surface treatment agent. The present invention also relates to a powder of which the surface has been treated with the aforementioned treatment agent.

A combination obtained from the aforementioned (A) co-modified organopolysiloxane and (D) powder, and optionally from (C) at least one oil agent, which is in the form of a liquid at 5 to 100° C., and is selected from the group consisting of a silicone oil, a non-polar organic compound and a low-polar organic compound is useful as a cosmetic raw material.

The aforementioned co-modified organopolysiloxane can be used as a thickening agent or a gelling agent. Therefore, the aforementioned (A) co-modified organopolysiloxane can constitute a gel composition together with (C) at least one oil agent, which is in the form of a liquid at 5 to 100° C., and is selected from the group consisting of a silicone oil, a non-polar organic compound and a low-polar organic compound.

The aforementioned co-modified organopolysiloxane can be blended in a preparation for external use, and in particular, in a cosmetic, as it is, or in the form of the aforementioned emulsion composition, the aforementioned powder, the aforementioned cosmetic raw material or the aforementioned gel composition.

The co-modified organopolysiloxane of the present invention can be obtained by reacting (a) an organopolysiloxane having hydrogen atoms binding to silicon atoms,
(b) an organic compound having one reactive unsaturated group in a molecule,
(c) a siloxane dendron compound having one reactive unsaturated group in a molecule, and
(d) a sugar alcohol functional organic compound having one reactive unsaturated group in a molecule,
in the presence of a catalyst for a hydrosilylation reaction.

In addition, optionally, (e) a hydrocarbon compound having one reactive unsaturated group in one molecule or a linear organopolysiloxane having one reactive unsaturated group in a molecule is preferably reacted.

The aforementioned (c) a siloxane dendron compound having one reactive unsaturated group in a molecule is preferably a compound having a siloxane dendron structure having one carbon-carbon double bond at the terminal of the molecular chain, represented by the following general formula (3'):

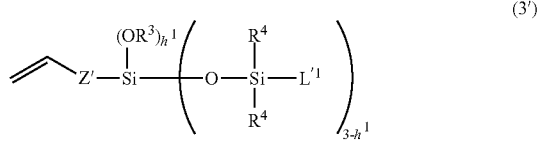

wherein
$R^3$ and $R^4$ are the same as defined above;
$Z'$ represents a divalent organic group;
$h^1$ is the number ranging from 0 to 3;
$L'^1$ represents $R^4$ or a silylalkyl group, in the case of $j=1$, represented by the following general formula (3''):

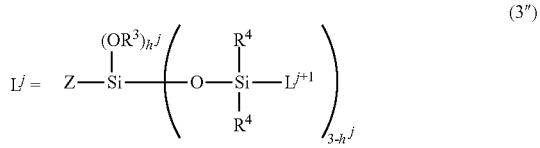

wherein $R^3$ and $R^4$ are the same as defined above;
Z represents a divalent organic group;
j specifies the number of generations of the aforementioned silylalkyl group, represented by $L^j$, in the case in which the number of generations of the aforementioned silylalkyl group, which is the number of repetitions of the aforementioned silylalkyl group, is k', j is an integer ranging from 1 to k', and the number of generations k' is an integer ranging from 1 to 9;
$L^{j+1}$ is the aforementioned silylalkyl group in the case of $j<k'$, and is $R^4$ in the case of $j=k'$; and $h^j$ is the number ranging from 0 to 3.

Advantageous Effects of Invention

The co-modified organopolysiloxane of the present invention is a novel silicone in which a sugar alcohol-containing organic group and a siloxane dendron structure are independently provided on the silicone main chain. By virtue of the presence of the aforementioned siloxane dendron structure, a distinctive feeling on touch and response capability with respect to various oil agents, that are different from properties obtained in the case of introducing a linear diorganopolysiloxane structure into the silicone main chain, can be exhibited. The distinctive feeling on touch is a specific property for the co-modified organopolysiloxane of the present invention. Namely, in the case of blending the co-modified organopolysiloxane of the present invention in a preparation for external use, and in particular, a cosmetic, a very smooth slippy sensation and light touch are provided, and as a result, an oily sensation caused by an organic oil and the like is reduced, and a cosmetic in which a moisturized feeling on touch is provided can be designed.

The co-modified organopolysiloxane of the present invention independently possesses both a sugar alcohol-containing organic group and a siloxane dendron structure in one molecule, and can also further possess a long-chain alkyl group and/or a linear diorganopolysiloxane group. For this reason, the co-modified organopolysiloxane can exhibit not only superior miscibility with a hydrophilic component, but also superior miscibility with a silicone oil, as well as, with a non-silicone oil such as a hydrocarbon oil, an ester oil or the like. Therefore, the co-modified organopolysiloxane of the present invention possesses extremely increased affinity with various oil agents, and has good surface activity power. When the co-modified organopolysiloxane of the present invention is used as a surfactant, a stable emulsion can be obtained.

In addition, the co-modified organopolysiloxane of the present invention can provide sensation during use in which both a moisturized aqueous sensation and a smooth, light and good spreading property are exhibited, with respect to an emulsified product, and the aforementioned sensation during use can be retained. Therefore, the co-modified organopolysiloxane of the present invention can be preferably blended in a preparation for external use, and in particular, a cosmetic. More particularly, the co-modified organopolysiloxane of the present invention can be preferably blended in a preparation for external use, and in particular, a cosmetic, as a raw material such as a surfactant, a powder treatment agent, a gelling agent or the like, optionally together with a powder, an oil agent or the like.

Therefore, a preparation for external use, and in particular, a cosmetic of the present invention possesses superior storage stability, a superior outer appearance, and a superior sensation during use, and in particular, is superior in water resistance, sebum resistance, glossiness, feeling on touch, an adhesive property with respect to hair and/or skin, and the like.

By further introducing a long-chain hydrocarbon group into the silicone main chain of the co-modified organopolysiloxane of the present invention, affinity to a non-silicone oil is further improved, and a miscibility effect with respect to various oil agents or an anchor effect can be increased. Thereby, more superior surface activity power can be exhibited.

BEST MODES FOR CARRYING OUT THE INVENTION

The co-modified organopolysiloxane of the present invention is represented by the following general formula (1):

wherein
$R^1$ represents a monovalent organic group, with the proviso that $R^2$, $L^1$ and Q are excluded therefrom;
$R^2$ represents a substituted or non-substituted, and linear or branched monovalent hydrocarbon group having 9 to 30 carbon atoms, or a linear organosiloxane group represented by the following general formula (2-1):

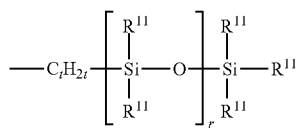

(2-1)

wherein $R^{11}$ is a substituted or non-substituted monovalent hydrocarbon group having 1 to 30 carbon atoms, a hydroxyl group or a hydrogen atom, and at least one $R^{11}$ is the aforementioned monovalent hydrocarbon group; t is the number ranging from 2 to 10; and r is the number ranging from 1 to 500,
or represented by the following general formula (2-2):

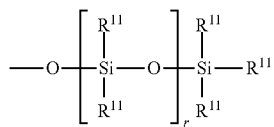

(2-2)

wherein $R^{11}$ and r are the same as defined above;
$L^1$ represents a silylalkyl group having a siloxane dendron structure, in the case of i=1, represented by the following general formula (3):

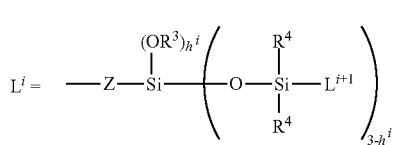

(3)

wherein
$R^3$ represents a substituted or non-substituted, and linear or branched monovalent hydrocarbon group having 1 to 30 carbon atoms;
$R^4$ independently represents an alkyl group having 1 to 6 carbon atoms or a phenyl group;
Z represents a divalent organic group;
i specifies the number of generations of the aforementioned silylalkyl group, represented by $L^i$, in the case in which the number of generations of the aforementioned silylalkyl group, which is the number of repetitions of the aforementioned silylalkyl group, is k, i is an integer ranging from 1 to k, and the number of generations k is an integer ranging from 1 to 10;
$L^{i+1}$ is the aforementioned silylalkyl group in the case of i<k, and is $R^4$ in the case of i=k; and $h^i$ is the number ranging from 0 to 3;
Q represents an organic group containing a sugar alcohol group;
each of a, b, c and d is independently the number having the following range: $1.0 \leq a \leq 2.5$, $0 \leq b \leq 1.5$, $0.0001 \leq c \leq 1.5$, and $0.0001 \leq d \leq 1.5$.

The monovalent organic group, which is $R^1$, is not particularly restricted as long as the monovalent organic group is not a functional group corresponding to $L^1$, $R^2$ or Q. The monovalent organic group preferably represents a substituted or non-substituted, and linear or branched monovalent hydrocarbon group having 1 to 8 carbon atoms, a polyoxyalkylene group represented by the following formula: $—R^5O(AO)_nR^6$ (wherein AO represents an oxyalkylene group having 2 to 4 carbon atoms; $R^5$ represents a substituted or non-substituted, and linear or branched divalent hydrocarbon group having 3 to 5 carbon atoms; $R^6$ represents a hydrogen atom, a substituted or non-substituted, and linear or branched monovalent hydrocarbon group having 1 to 24 carbon atoms, or a substituted or non-substituted, and linear or branched acyl group having 2 to 24 carbon atoms; and n=1 to 100), a hydroxyl group, an alkoxy group or a hydrogen atom, with the proviso that all $R^1$s do not represent a hydroxyl group, a hydrogen atom, the aforementioned alkoxy group or the aforementioned polyoxyalkylene group.

As examples of monovalent hydrocarbon groups having 1 to 8 carbon atoms, mention may be made of, for example, alkyl groups such as a methyl group, an ethyl group, a propyl group, a butyl group, a pentyl group, a hexyl group, a heptyl group, an octyl group and the like; cycloalkyl groups such as a cyclopentyl group, a cyclohexyl group and the like; alkenyl groups such as a vinyl group, an allyl group, a butenyl group and the like; aryl groups such as a phenyl group, a tolyl group and the like; aralkyl groups such as a benzyl group and the like; substituted groups thereof in which the hydrogen atoms binding to the carbon atoms of the aforementioned groups are at least partially substituted with a halogen atom such as a fluorine atom or the like, or an organic group containing an epoxy group, a glycidyl group, an acyl group, a carboxyl group, an amino group, a methacryl group, a mercapto group or the like, with the proviso that the total number of the carbon atoms ranges from 1 to 8 carbon atoms. The monovalent hydrocarbon group is preferably a group other than an alkenyl group, and a methyl group, an ethyl group or a phenyl group is, in particular, preferred. In addition, as examples of alkoxy groups, mention may be made of lower alkoxy groups such as a methoxy group, an ethoxy group, an isopropoxy group, a butoxy group and the like; higher alkoxy groups such as a laurylalkoxy group, a myristylalkoxy group, a palmitylalkoxy group, an oleylalkoxy group, a stearylalkoxy group, a behenylalkoxy group and the like.

The substituted or non-substituted, and linear or branched monovalent hydrocarbon group having 9 to 30 carbon atoms as $R^2$ of the aforementioned general formula (1) is a long-chain hydrocarbon group or a linear organosiloxane group represented by the aforementioned general formula (2-1) or (2-2). By introducing into the main chain and/or the side chain of the polysiloxane, an emulsifying property and a dispersing property with respect to an oil agent, a powder and, the like can be further improved, and in addition, sensation during use in the case of blending in a cosmetic can also be further improved. In addition, the aforementioned monovalent long-chain hydrocarbon group or linear organopolysiloxane group is a hydrophobic functional group, and for this reason, miscibility and/or blending stability with respect to an organic oil having an increased amount of an alkyl group can be further improved. All $R^2$s may be the aforementioned monovalent long-chain hydrocarbon group or linear organopolysiloxane group, and may also be both of the aforementioned functional groups. In the co-modified organopolysiloxane of the present invention, in particular, a part or all of the $R^2$s is/are preferably a monovalent long-chain hydrocarbon group. By possessing the aforementioned monovalent long-chain hydrocarbon group in a molecule, the co-modified organopolysiloxane of the present invention can exhibit superior miscibility with respect to not only a silicone oil, but also a non-silicone oil having an increased amount of an alkyl group. For example, an emulsion or dispersion formed from a non-silicone oil, which exhibits superior thermal stability and superior stability over time, can be obtained.

The substituted or non-substituted, and linear or branched monovalent hydrocarbon groups having 9 to 30 carbon atoms, binding to a silicon atom, represented by $R^2$ of the aforementioned general formula (1) may be the same or different, and the structure thereof is selected from a linear structure, a branched structure, and a partially branched structure. In the present invention, in particular, a non-substituted and linear monovalent hydrocarbon group is preferably used. As examples of non-substituted monovalent hydrocarbon groups, mention may be made of, for example, an alkyl group, an aryl group, or an aralkyl group, having 9 to 30 carbon atoms, and preferably having 10 to 25 carbon atoms. On the other hand, as examples of substituted monovalent hydrocarbon groups, mention may be made of, for example, a perfluoroalkyl group, an aminoalkyl group, an amidoalkyl group, and a carbinol group, having 9 to 30 carbon atoms, and preferably having 10 to 25 carbon atoms. In addition, a part of the carbon atoms of the aforementioned monovalent hydrocarbon group may be substituted with an alkoxy group, and as examples thereof, mention may be made of, a methoxy group, an ethoxy group, and a propoxy group. The aforementioned monovalent hydrocarbon group is, in particular, preferably an alkyl group having 9 to 30 carbon atoms, and examples thereof include a group represented by the following general formula: —$(CH_2)_v$—$CH_3$ wherein v is the number ranging from 8 to 30. An alkyl group having 10 to 25 carbon atoms is, in particular, preferred.

The linear organosiloxane group represented by the aforementioned general formula (2-1) or (2-2) is different from the silylalkyl group having a siloxane dendron structure, and has a linear polysiloxane chain structure. In the aforementioned general formula (2-1) or (2-2), each $R^{11}$ is independently a substituted or non-substituted monovalent hydrocarbon group having 1 to 30 carbon atoms, a hydroxyl group or a hydrogen atom. The substituted or non-substituted monovalent hydrocarbon group having 1 to 30 carbon atoms is preferably an alkyl group having 1 to 30 carbon atoms, an aryl group having 6 to 30 carbon atoms, an aralkyl group having 6 to 30 carbon atoms, or a cycloalkyl group having 6 to 30 carbon atoms. As examples thereof, mention may be made of alkyl groups such as a methyl group, an ethyl group, a propyl group, a butyl group, a pentyl group, a hexyl group, a heptyl group, an octyl group, a decyl group and the like; cycloalkyl groups such as a cyclopentyl group, a cyclohexyl group and the like; and aryl groups such as a phenyl group, a tolyl group and the like. The hydrogen atoms binding to the carbon atoms of the aforementioned groups may be at least partially substituted with a halogen atom such as a fluorine atom or the like, or an organic group containing an epoxy group, an acyl group, a carboxyl group, an amino group, a methacryl group, a mercapto group and the like. As examples of particularly preferable groups as $R^{11}$, mention may be made of a methyl group, a phenyl group or a hydroxyl group. A mode in which a part of $R^{11}$ is a methyl group, and another part thereof is a long-chain alkyl group having 8 to 30 carbon atoms is also preferred.

In the aforementioned general formula (2-1) or (2-2), each t is the number ranging from 2 to 10, r is the number ranging from 1 to 500, and r is preferably the number ranging from 2 to 500. The aforementioned linear organosiloxane group is hydrophobic, and in view of miscibility with various oil agents, r is preferably the number ranging from 1 to 100, and more preferably the number ranging from 2 to 30.

As examples of substituted or non-substituted, and linear or branched monovalent hydrocarbon groups having 1 to 30 carbon atoms, represented by $R^3$ of the aforementioned general formula (3), mention may be made of, for example, alkyl groups such as a methyl group, an ethyl group, a propyl group, a butyl group, a pentyl group, a hexyl group, a heptyl group, an octyl group and the like; cycloalkyl groups such as a cyclopentyl group, a cyclohexyl group and the like; alkenyl groups such as a vinyl group, an allyl group, a butenyl group and the like; aryl groups such as a phenyl group, a tolyl group and the like; aralkyl groups such as a benzyl group and the like; substituted groups thereof in which the hydrogen atoms binding to the carbon atoms of the aforementioned groups are at least partially substituted with a halogen atom such as a fluorine atom or the like, or an organic group containing an epoxy group, a glycidyl group, an acyl group, a carboxyl group, an amino group, a methacryl group, a mercapto group or the like, with the proviso that the total number of the carbon atoms ranges from 1 to 30 carbon atoms.

In the co-modified organopolysiloxane according to the present invention, in order to provide a further functional property, a modified group other than the group having a siloxane dendron structure (-$L^1$) and the hydrophilic group (-Q), and in particular, a short-chain or medium-chain hydrocarbon-based group may be introduced as $R^1$, and the organopolysiloxane can be designed. Namely, in the case of $R^1$ being a substituted monovalent hydrocarbon group, a substituent can be appropriately selected in accordance with a property and a usage to be provided. For example, in the case of using the co-modified organopolysiloxane as a raw material of a cosmetic, for the purpose of improving sensation during use, feeling on touch, and durability, an amino group, an aminoethyl aminopropyl group, a carboxyl group or the like can be introduced as a substituent of the monovalent hydrocarbon group.

In particular, $R^1$ is preferably a monovalent hydrocarbon group or a monovalent fluorinated hydrocarbon group, having 1 to 8 carbon atoms and having no aliphatic unsaturated bond. As examples of the monovalent hydrocarbon group having no aliphatic unsaturated bond belonging to $R^3$, mention may be made of alkyl groups such as a methyl group, an ethyl group, a propyl group, a butyl group, a pentyl group, a hexyl group and the like; aryl groups such as a phenyl group, a tolyl group, a xylyl group and the like; and aralkyl groups such as a benzyl group and the like. As examples of monovalent fluorinated hydrocarbon groups, mention may be made of perfluoroalkyl groups such as a trifluoropropyl group, a pentafluoroethyl group and the like. From an industrial point of view, $R^3$ is preferably a methyl group, an ethyl group, or a phenyl group. In particular, from an industrial point of view, 90% by mol to 100% by mol of all $R^1$s is preferably a group selected from the group consisting of a methyl group, an ethyl group and a phenyl group.

In the aforementioned general formula (1), a group represented by $L^1$ is a silylalkyl group having a siloxane dendron structure, and is defined as a silylalkyl group represented by the aforementioned general formula (3) in the case of i=1. The aforementioned silylalkyl group having a siloxane dendron structure includes a structure in which carbosiloxane units are spread in the form of a dendrimer, and is a functional group exhibiting increased water-repellency, as compared with linear polysiloxane units or simply branched polysiloxane units. The co-modified organopolysiloxane of the present invention can enhance increased miscibility with not only a silicone oil, but also various oil agents such as a hydrocarbon oil, an ester oil and the like, by virtue of the presence of the siloxane dendron structure. In addition, the co-modified organopolysiloxane of the present invention can obtain a distinctive superior sensation during use by virtue of the presence of the siloxane dendron structure. In addition, since good balance of the combination with a hydrophilic group is exhibited, a superior effect of thickening an oil agent and superior gelling ability can be provided to the co-modified organopolysiloxane of the present invention. Furthermore, the aforementioned silylalkyl group having a siloxane dendron structure is a chemically stable functional group which is capable of imparting an advantageous property that widely-ranged cosmetic ingredients can be combined therewith and can be used.

In the aforementioned general formula (3), $R^4$ is an alkyl group having 1 to 6 carbon atoms or a phenyl group. As examples of alkyl groups having 1 to 6 carbon atoms, mention may be made of linear, branched or cyclic alkyl groups such as a methyl group, an ethyl group, a n-propyl group, an i-propyl group, a n-butyl group, an i-butyl group, a s-butyl group, a pentyl group, a neopentyl group, a cyclopentyl group, a hexyl group and the like.

In the aforementioned general formula (3), i specifies the number of generations of the aforementioned silylalkyl group, represented by $L^i$, in the case in which the number of generations of the aforementioned silylalkyl group, which is the number of repetitions of the aforementioned silylalkyl group, is k, i is an integer ranging from 1 to k, and the number of generations k is an integer ranging from 1 to 10. $L^{i+1}$ is the aforementioned silylalkyl group in the case of i<k, and $L^{i+1}$ is a methyl group or a phenyl group in the case of i=k. In particular, in the case of i=k, $L^{i+1}$ is preferably a methyl group. $h^i$ is the number ranging from 0 to 3.

The aforementioned number of generations k is preferably an integer ranging from 1 to 3, and more preferably 1 or 2 from an industrial viewpoint. In each number of generations, the group represented by $L^1$ is represented as follows, wherein $R^2$ and Z are the same groups as described above.

In the case of the number of generations k=1, $L^1$ is represented by the following general formula (3-1):

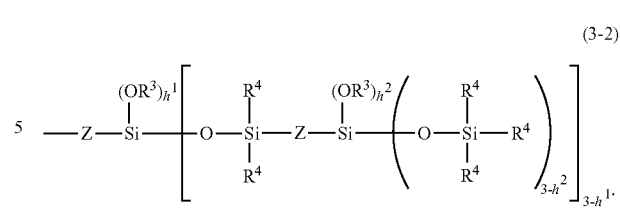

In the case of the number of generations k=2, $L^1$ is represented by the following general formula (3-2):

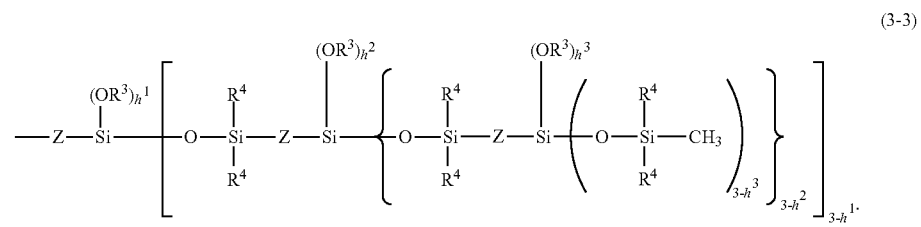

In the case of the number of generations k=3, $L^1$ is represented by the following general formula (3-3):

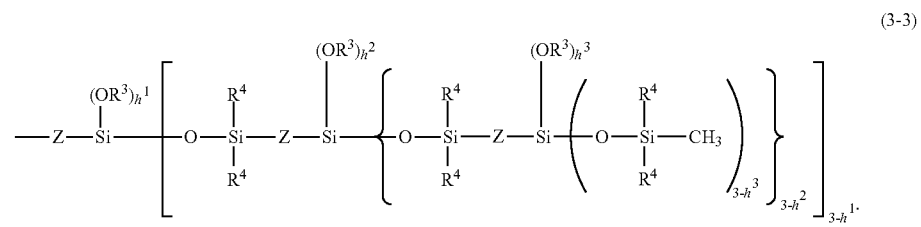

In the aforementioned general formula (3), each $h^i$ is independently the number ranging from 0 to 3. In the structures represented by the aforementioned general formulae (3-1) to (3-3) in the case of the number of generations ranging from 1 to 3, each of $h^1$, $h^2$ and $h^3$ is independently the number ranging from 0 to 3. The aforementioned $h^i$ is preferably the number particularly ranging from 0 to 1, and $h^1$ is, in particular, preferably 0.

In the aforementioned general formulae (3) and (3-1) to (3-3), each Z is independently a divalent organic group. In particular, as examples thereof, mention may be made of a divalent organic group formed by addition-reacting a silicon-binding hydrogen atom and a functional group having an unsaturated hydrocarbon group such as an alkenyl group, an acryloxy group, a methacryloxy group or the like at the terminal. In accordance with the method of introducing a silylalkyl group having a siloxane dendron structure, the functional groups can be appropriately selected and are not restricted to the aforementioned functional groups. Preferably, each Z is independently a group selected from divalent organic groups represented by the following general formulae:

—$R^7$—

—$R^7$—CO—

—$R^7$—COO—$R^8$—

—CO—$R^7$—

—$R^7$—COO—$R^8$—

—$R^7$—CONH—$R^8$—

—$R^7$—$R^8$—

In the aforementioned general formulae, each $R^7$ independently represents a substituted or non-substituted, and linear or branched alkylene or alkenylene group having 2 to 22 carbon atoms, or an arylene group having 6 to 22 carbon atoms. More particularly, as examples of $R^7$, mention may be made of linear alkylene groups such as an ethylene group, a propylene group, a butylene group, a hexylene group and the like; and branched alkylene groups such as a methylmethylene group, a methylethylene group, a 1-methylpentylene group, a 1,4-dimethylbutylene group and the like. $R^7$ is preferably a group selected from an ethylene group, a propylene group, a methylethylene group and a hexylene group.

In the aforementioned general formulae, $R^8$ is a group selected from divalent organic groups represented by the following formulae:

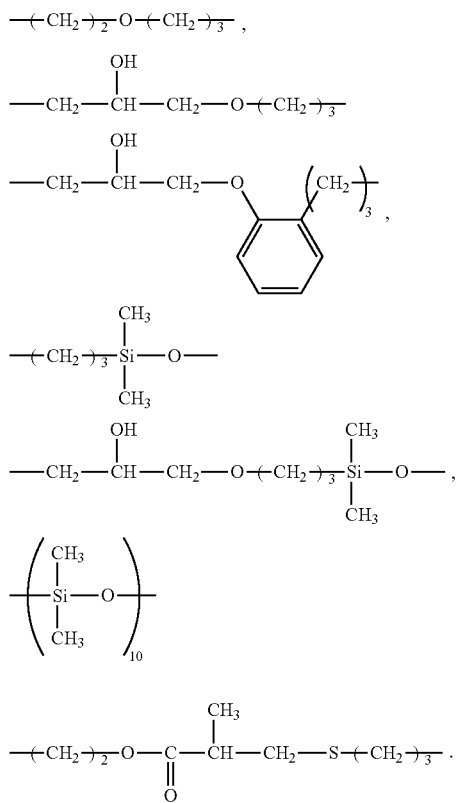

In particular, Z in $L^1$ is preferably a divalent organic group represented by the following general formula: —$R^7$—, introduced by a reaction between a silicon-binding hydrogen atom and an alkenyl group. In the same manner, Z is preferably a divalent organic group represented by the following general formula: —$R^7$—COO—$R^8$—, introduced by a reaction between a silicon-binding hydrogen atom and an unsaturated carboxylic ester group. On the other hand, in the silylalkyl group represented by $L^i$, in which the number of generations k is 2 or more, and $L^i$ is $L^2$ to $L^k$, Z is preferably an alkylene group having 2 to 10 carbon atoms, in particular, preferably a group selected from an ethylene group, a propylene group, a methylethylene group and a hexylene group, and most preferably an ethylene group.

In the aforementioned general formula (1), Q is a sugar alcohol-containing organic group, and constitutes a hydrophilic moiety of the co-modified organopolysiloxane of the present invention. Q is not particularly restricted in the structure as long as the structure has a sugar alcohol moiety. In Q, a sugar alcohol residue is preferably bound to a silicon atom via a divalent organic group.

Therefore, Q is preferably represented by the following general formula (4-1):

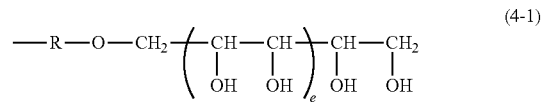

wherein
R represents a divalent organic group; and
e is 1 or 2,
or represented by the following general formula (4-2):

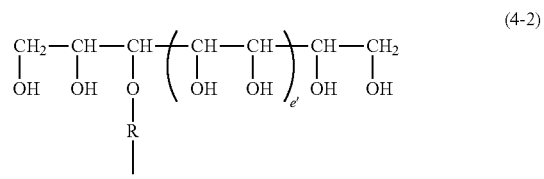

wherein
R is the same as defined above; and
e' is 0 or 1.

The co-modified organopolysiloxane according to the present invention is characterized in that among the sugar alcohol-containing organic groups represented by the aforementioned general formula (4-1) or (4-2), at least one type of the groups binds to a silicon atom. In addition, the co-modified organopolysiloxane may be an organopolysiloxane in which two or more types of sugar alcohol-containing organic groups selected from the aforementioned sugar alcohol-containing organic groups are possessed in an identical molecule. In the same manner, a mixture of the organopolysiloxanes having different sugar alcohol-containing organic groups may be used.

The divalent organic group represented by R of the aforementioned general formula (4-1) or (4-2) is not particularly restricted, and as an example thereof, mention may be made of a substituted or non-substituted, and linear or branched divalent hydrocarbon group having 1 to 30 carbon atoms. A substituted or non-substituted, and linear or branched divalent hydrocarbon group having 3 to 5 carbon atoms is preferred. As examples of the substituted or non-substituted, and linear or branched divalent hydrocarbon group having 1 to 30 carbon atoms, mention may be made of, for example, linear or branched alkylene groups having 1 to 30 carbon atoms such as a methylene group, a dimethylene group, a trimethylene group, a tetramethylene group, a pentamethylene group, a hexamethylene group, a heptamethylene group, an octamethylene group and the like; alkenylene groups having 2 to 30 carbon atoms such as a vinylene, an allylene group, a butenylene group, a hexenylene group, an octenylene group and the like; arylene groups having 6 to 30 carbon atoms such as a phenylene group, a diphenylene group and the like; alkylenearylene groups having 7 to 30 carbon atoms such as a dimethylenephenylene group and the like; and substituted groups thereof in which hydrogen atoms binding to carbon atoms of the aforementioned groups are at least partially substituted by a halogen atom such as a fluorine atom or the like, or an organic group containing a carbinol group, an epoxy group, a glycidyl group, an acyl group, a carboxyl group, an amino group, a methacryl group, a mercapto group, an amide group, an oxyalkylene group or the like. The divalent hydrocarbon group is preferably an alkylene group having 1 to 30 carbon atoms, more preferably an alkylene group having 1 to 6 carbon atoms, and further preferably an alkylene group having 3 to 5 carbon atoms.

As the sugar alcohol-containing organic group, the case in which R is a propylene group and e=1 in the aforementioned general formula (4-1) is, in particular, preferred. In the same manner as described above, as the sugar alcohol-containing organic group, the case in which R is a propylene group and e'=0 in the aforementioned general formula (4-2) is, in particular, preferred. The sugar alcohol-containing organic group in this case is a xylitol residue (hereinafter, merely referred to as "xylitol residue" or "xylitol-modified group") represented by the following structural formula: —$C_3H_6$—$OCH_2[CH(OH)]_3CH_2OH$ or the following structural formula: —$C_3H_6$—$OCH\{CH(OH)CH_2OH\}_2$, respectively in the case of the aforementioned general formula (4-1) or (4-2).

The binding site of the sugar alcohol-containing organic group may be any one of the side chains or the terminals of the polysiloxane which is the main chain. A structure in which two or more sugar alcohol-containing organic groups are present in one molecule of the co-modified organopolysiloxane may be used. In addition, the aforementioned two or more sugar alcohol-containing organic groups may be the same or different sugar alcohol-containing organic groups. A structure in which the aforementioned two or more sugar alcohol-containing organic groups bind to only the side chains, only the terminals, or both the side chain and the terminal of the polysiloxane which is the main chain may be used.

A co-modified organopolysiloxane possessing a silylalkyl group (-$L^1$) having a siloxane dendron structure and a sugar alcohol group-containing organic group (-Q), represented by the aforementioned general formula (1) is preferably a co-modified organopolysiloxane possessing a linear polysiloxane structure represented by the following structural formula (1-1):

(1-1)

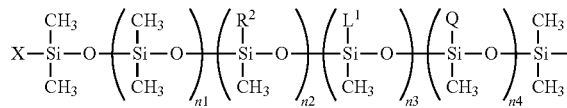

wherein
$R^2$, $L^1$ and Q are the same as defined above;
X is a group selected from the group consisting of a methyl group, $R^2$, $L^1$ and Q;
each of n1, n2, n3 and n4 is independently the number ranging from 0 to 2,000, and n1+n2+n3+n4 is the number ranging from 0 to 2,000, with the proviso that in the case of n3=0, at least one X is $L^1$, and in the case of n4=0, at least one X is Q.

In the aforementioned structural formula (1-1), each Q is independently a sugar alcohol-containing organic group represented by the aforementioned general formula (4-1) or general formula (4-2). In the co-modified organopolysiloxane according to the present invention, all Qs may be sugar alcohol-containing organic groups represented by the aforementioned general formula (4-1) or general formula (4-2), or alternatively, a part of Q in one molecule may be a sugar alcohol-containing organic group represented by the aforementioned general formula (4-1), and the remaining Q may be a sugar alcohol-containing organic group represented by the aforementioned general formula (4-2).

In addition, the co-modified organopolysiloxane according to the present invention may be one type of the co-modified organopolysiloxane represented by the aforementioned general formula (1) or a mixture of two or more types thereof.

In particular, in the co-modified organopolysiloxane according to the present invention, represented by the aforementioned general formula (1), Q is preferably a sugar alcohol-containing organic group which is a xylitol residue.

As described above, the xylitol residue is a group represented by the structural formula: —$C_3H_6$—$OCH_2[CH(OH)]_3CH_2OH$ or the structural formula: —$C_3H_6$—$OCH\{CH(OH)CH_2OH\}_2$. In the co-modified organopolysiloxane according to the present invention, the aforementioned xylitol residues may be one type or two types. Therefore, in the aforementioned general formula (1), all Qs may consist of only the xylitol residue represented by the structural formula: —$C_3H_6$—$OCH_2[CH(OH)]_3CH_2OH$ or the structural formula: —$C_3H_6$—$OCH\{CH(OH)CH_2OH\}_2$, or alternatively, Qs may consist of two types of xylitol residues represented by the structural formula: —$C_3H_6$—$OCH_2[CH(OH)]_3CH_2OH$ and represented by the structural formula: —$C_3H_6$—$OCH\{CH(OH)CH_2OH\}_2$. In the latter case, the composition ratio (weight ratio) preferably ranges from 5:5 to 10:0, and in particular, preferably ranges from 8:2 to 10:0. The case of 10:0 means that Q substantially consists of only a xylitol residue represented by the structural formula: —$C_3H_6$—$OCH_2[CH(OH)]_3CH_2OH$.

In addition, in the case in which the co-modified organopolysiloxane according to the present invention is a mixture of two or more types of co-modified organopolysiloxanes, the aforementioned mixture can comprise at least two types of co-modified organopolysiloxanes selected from the group consisting of a co-modified organopolysiloxane in which Q in the aforementioned general formula (1) consists of only a xylitol residue represented by the structural formula: —$C_3H_6$—$OCH_2[CH(OH)]_3CH_2OH$, a co-modified organopolysiloxane in which Q in the aforementioned general formula (1) consists of only a xylitol residue represented by the structural formula: —$C_3H_6$—$OCH\{CH(OH)CH_2OH\}_2$, and a co-modified organopolysiloxane in which Q in the aforementioned general formula (1) consists of two types of xylitol residues represented by the structural formula: —$C_3H_6$—$OCH_2[CH(OH)]_3CH_2OH$ and the structural formula: —$C_3H_6$—$OCH\{CH(OH)CH_2OH\}_2$ in a constitutional ratio (weight ratio) preferably ranging from 5:5 to 10:0 and in particular, preferably ranging from 8:2 to 10:0. In addition, the co-modified organopolysiloxane according to the present invention may be a mixture of at least two types of co-modified organopolysiloxanes in which Q in the aforementioned general formula (1) consists of two types of xylitol residues represented by the structural formula: —$C_3H_6$—$OCH_2[CH(OH)]_3CH_2OH$ and the structural formula: —$C_3H_6$—$OCH\{CH(OH)CH_2OH\}_2$ in a constitutional ratio (weight ratio) preferably ranging from 5:5 to 10:0 and in particular, preferably ranging from 8:2 to 10:0, in which the constitutional ratio is different from each other.

In the aforementioned formula (1-1), (n1+n2+n3+n4) is preferably the number ranging from 0 to 1,000, and in particular, preferably the number ranging from 0 to 500. n1 is preferably the number ranging from 0 to 1,000, and more preferably the number ranging from 0 to 500. n2 is preferably the number ranging from 0 to 200, and more preferably the number ranging from 0 to 150. In the case of R2 being the aforementioned long-chain alkyl group, in particular, n2>1 is preferred in view of surface activity and miscibility with oil agents other than silicones. n3 is preferably the number ranging from 0 to 250, and in particular, it is preferred that n3>1 and one or more silylalkyl groups (-L¹) having a siloxane dendron structure at the side chain part be possessed. n4 is the number ranging from 0 to 100, and preferably the number ranging from 0 to 50, with the proviso that in the case of n4=0, at least one X must be Q.

As the co-modified organopolysiloxane of the present invention, a co-modified organopolysiloxane represented by the following structural formula (1-1-1):

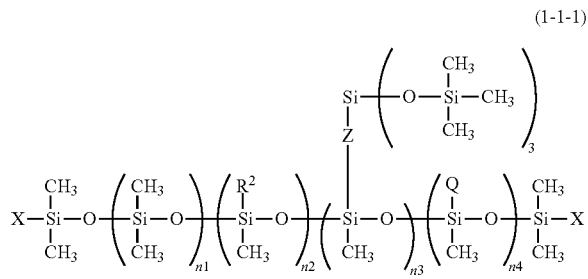

wherein
R², Q, X, Z, n1, n2, n3 and n4 are the same as defined above, or represented by the following structural formula (1-1-2):

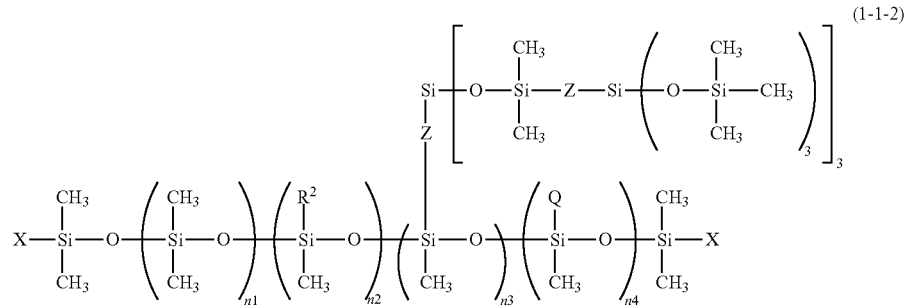

wherein
R², Q, X, Z, n1, n2, n3 and n4 are the same as defined above, is preferred.

A modification index of an organopolysiloxane with a sugar alcohol-containing organic group preferably ranges from 1 to 50% by mol, more preferably ranges from 2.5 to 40% by mol, further preferably ranges from 5 to 30% by mol, and in particular, preferably ranges from 10 to 20% by mol, among all functional groups binding to the polysiloxane which is the main chain. In the co-modified organopolysiloxane represented by the aforementioned structural formula (1-1), the modification index with a sugar alcohol-containing organic group is indicated by the following equation:

Modification index (% by mol)=100×(the number of sugar alcohol-containing organic groups binding to a silicon atom in one molecule)/{6+2×(a+b+c)}.

For example, in the case of a co-modified organopolysiloxane formed from a trisiloxane possessing one sugar alcohol-containing organic group, one functional group binding to a silicon atom among eight functional groups binding to silicon atoms is modified with a sugar alcohol-containing organic group. For this reason, the modification index with a sugar alcohol-containing organic group is 12.5% by mol.

The co-modified organopolysiloxane of the present invention can be obtained by reacting (a) an organopolysiloxane having hydrogen atoms binding to silicon atoms, (b) an organic compound having one reactive unsaturated group in one molecule, (c) a siloxane dendron compound having one reactive unsaturated group in one molecule, and (d) a sugar alcohol-functional organic compound having one reactive unsaturated group in one molecule, in the presence of a catalyst for a hydrosilylation reaction. As preferable examples of the aforementioned reactive unsaturated group, mention may be made of an alkenyl group or an unsaturated fatty acid ester group, which is an unsaturated functional group having a carbon-carbon double bond. The aforementioned —R¹ is introduced by the aforementioned component (b), and the aforementioned -L¹ is introduced by the aforementioned component (c).

The aforementioned (d) sugar alcohol-functional organic compound having one reactive unsaturated group in one molecule can be replaced with a ketal derivative of a sugar alcohol compound which has a reactive unsaturated group in a molecule and in which a hydroxyl group is protected, and the ketal derivative can be used as a raw material. In this case, the ketal derivative is subjected to an addition reaction to an organopolysiloxane having a silicon-hydrogen bond, followed by subjecting to an acid hydrolyzing treatment to deprotect the hydroxyl group. Thereby, a co-modified organopolysiloxane according to the present invention can be produced.

The co-modified organopolysiloxane of the present invention can be obtained, for example, in the following manner.

The co-modified organopolysiloxane of the present invention can be obtained by addition-reacting an organopolysiloxane having silicon-hydrogen bonds with an unsaturated organic compound having a carbon-carbon double bond at one terminal of the molecular chain, a siloxane dendron compound having a carbon-carbon double bond at one terminal of the molecular chain, and an unsaturated ether compound of a sugar alcohol having a carbon-carbon double bond in the molecule. In addition, an unsaturated long-chain hydrocarbon compound having a carbon-carbon double bond at one terminal of the molecular chain or a linear organopolysiloxane having a carbon-carbon double bond at one terminal of the molecular chain can be further subjected to an addition reaction. By using the aforementioned unsaturated long-chain hydrocarbon compound or linear organopolysiloxane having a carbon-carbon double bond at one terminal of the molecular chain, the aforementioned —R² can be introduced.

In the case described above, the co-modified organopolysiloxane of the present invention can be obtained as a hydrosilylation reaction product between a siloxane containing SiH groups and the aforementioned unsaturated organic compound, the aforementioned siloxane dendron compound and the aforementioned unsaturated ether compound of a sugar alcohol, as well as, optionally the aforementioned unsaturated long-chain hydrocarbon compound or linear organopolysiloxane. Thereby, an organic group, a silylalkyl group having a siloxane dendron structure, and a sugar alcohol-containing organic group, as well as, optionally a long-chain hydrocarbon group or a linear organopolysiloxane group can be introduced into the polysiloxane chain of the co-modified organopolysiloxane of the present invention.

For example, the co-modified organopolysiloxane of the present invention can be obtained by at least reacting (a') an organohydrogensiloxane represented by the following general formula (1'):

$$R^1_a H_{b+c} SiO_{(4-a-b-c-d)/2} \quad (1')$$

wherein,
$R^1$, a, b and c are the same as defined above,
(c) a siloxane dendron compound having one reactive unsaturated group in one molecule, and (d) a sugar alcohol-functional organic compound having one reactive unsaturated group in one molecule, in the presence of a catalyst for a hydrosilylation reaction. (e) A hydrocarbon compound having one reactive unsaturated group in one molecule or a linear organopolysiloxane having one reactive unsaturated group in one molecule is preferably further reacted therewith.

The co-modified organopolysiloxane of the present invention can be preferably produced by reacting the aforementioned (c) component, the aforementioned (d) component, and the aforementioned (a') organohydrogensiloxane represented by the aforementioned general formula (1'), as well as optionally, the aforementioned (e) hydrocarbon compound having one reactive unsaturated group in one molecule or the aforementioned linear organopolysiloxane having one reactive unsaturated group in one molecule, under the condition of at least co-existing (c) the siloxane dendron compound having one reactive unsaturated group in one molecule and (d) the sugar alcohol-functional organic compound having one reactive unsaturated group in one molecule. Alternatively, the co-modified organopolysiloxane of the present invention can be preferably produced by reacting the aforementioned (a') organohydrogensiloxane and the aforementioned (c) component in an amount of 0.9 equivalent or less with respect to the amount of the silicon-binding hydrogen atoms of the aforementioned (a') component, followed by subjecting the aforementioned (d) component and optionally the aforementioned (e) component to an addition reaction therewith.

As the aforementioned (a) organopolysiloxane having silicon atom-binding hydrogen atoms and the aforementioned (a') organohydrogensiloxane, an organohydrogensiloxane represented by the following structural formula (1-1)':

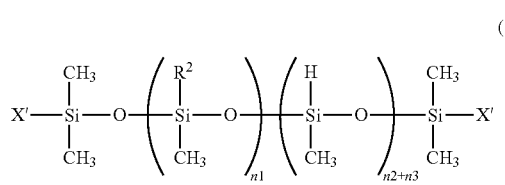

(1-1)' wherein,
each $R^1$ is the same as defined above;
X' is a group selected from $R^1$ and a hydrogen atom;
n1, n2 and n3 are the same as defined above, with the proviso that in the case of n2+n3=0, at least one X' is a hydrogen atom,
is preferred.

As the aforementioned (c) siloxane dendron compound having one reactive unsaturated group in one molecule, a compound having a siloxane dendron structure having one carbon-carbon double bond at the terminal of the molecular chain, represented by the following general formula (3'):

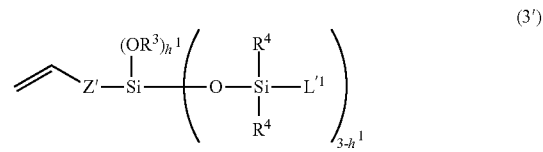

(3')

wherein
$R^3$ and $R^4$ are the same as defined above;
Z' represents a divalent organic group;
$h^1$ is the number ranging from 0 to 3;
$L'^1$ represents $R^4$ or a silylalkyl group, in the case of j=1, represented by the following general formula (3"):

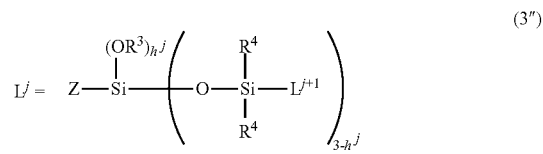

(3")

wherein $R^3$ and $R^4$ are the same as defined above;
Z represents a divalent organic group;
j specifies the number of generations of the aforementioned silylalkyl group, represented by $L^j$, in the case in which the number of generations of the aforementioned silylalkyl group, which is the number of repetitions of the aforementioned silylalkyl group, is k', j is an integer ranging from 1 to k', and the number of generations k' is an integer ranging from 1 to 9;
$L^{j+1}$ is the aforementioned silylalkyl group in the case of j<k', and $L^{j+1}$ is $R^4$ in the case of j=k'; and $H^j$ is the number ranging from 0 to 3,
is preferred.

As the aforementioned (d) sugar alcohol-functional organic compound having one reactive unsaturated group in one molecule, a mono-unsaturated ether compound of a sugar alcohol represented by the following general formula (4'-1):

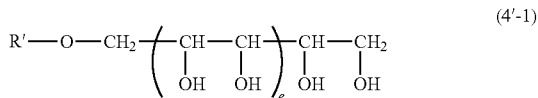

(4'-1)

wherein
R' represents an unsaturated organic group;
e is 1 or 2 and preferably 1, or represented by the following general formula (4'-2):

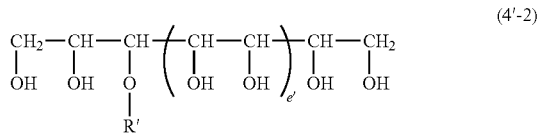

wherein
R' represents an unsaturated organic group;
e' is 0 or 1 and preferably 1,
is preferred.

The aforementioned unsaturated organic group is not particularly restricted as long as the organic group has an unsaturated group. A substituted or non-substituted, and linear or branched, unsaturated hydrocarbon group having 3 to 5 carbon atoms is preferred. As examples of unsaturated hydrocarbon groups having 3 to 5 carbon atoms, mention may be made of alkenyl groups such as a vinyl group, an allyl group, a butenyl group and the like. An allyl group is preferred.

As the aforementioned mono-unsaturated ether compound of a sugar alcohol, a monoallyl ether of a sugar alcohol is preferred, and xylitol monoallyl ether (hereinafter, referred to as "xylitol monoallyl ether") represented by the following structural formula: $CH_2=CH-CH_2-OCH_2[CH(OH)]_3CH_2OH$ or represented by the following structural formula: $CH_2=CH-CH_2-OCH\{CH(OH)CH_2OH\}_2$ is more preferred. The xylitol monoallyl ether can be synthesized in accordance with a conventional method, and some products are commercially available.

As the aforementioned xylitol monoallyl ether, either one or a mixture of a compound represented by the following structural formula: $CH_2=CH-CH_2-OCH_2[CH(OH)]_3CH_2OH$ and a compound represented by the following structural formula: $CH_2=CH-CH_2-OCH\{CH(OH)CH_2OH\}_2$ can be used without particular restriction. Preferably, either one of the xylitol monoallyl ethers represented by the following structural formula: $CH_2=CH-CH_2-OCH_2[CH(OH)]_3CH_2OH$ and represented by the following structural formula: $CH_2=CH-CH_2-OCH\{CH(OH)CH_2OH\}_2$ is purified and used as a raw material. Alternatively, a xylitol monoallyl ether mixture containing xylitol monoallyl ethers represented by the following structural formula: $CH_2=CH-CH_2-OCH_2[CH(OH)]_3CH_2OH$ and represented by the following structural formula: $CH_2=CH-CH_2-OCH\{CH(OH)CH_2OH\}_2$ in a weight (mass) ratio ranging from 5:5 to 10:0 is preferably used as a raw material. In the latter case, use of the xylitol monoallyl ether having a ratio ranging from 8:2 to 10:0 is more preferred. In the case of using a ratio of 10:0, the raw material is a purified product consisting substantially of the xylitol monoallyl ether represented by the following structural formula: $CH_2=CH-CH_2-OCH_2[CH(OH)]_3CH_2OH$.

In addition, as described above, in order to obtain the aforementioned co-modified organopolysiloxane, a derivative of a sugar alcohol compound (a ketal compound) in which a hydroxyl group of the sugar alcohol compound corresponding to a sugar alcohol-modified group to be introduced is protected by a ketalizing agent such as 2,2-dimethoxypropane or the like in the presence of an acid catalyst, can also be used as a raw material. More particularly, the ketal derivative of the sugar alcohol having a carbon-carbon double bond in the molecule, which is obtained by purifying a reaction product between the aforementioned ketal compound and an alkenyl halide, instead of the aforementioned monounsaturated ether compound of a sugar alcohol, is subjected to an addition reaction with an organopolysiloxane having silicon-hydrogen bonds. After the addition reaction, a de-ketalization reaction can be carried out by means of an acid hydrolysis treatment to deprotect the hydroxyl group. Thereby, the co-modified organopolysiloxane according to the present invention can also be produced. Even by the aforementioned method using the aforementioned ketal derivative, after deprotection, an organopolysiloxane having a sugar alcohol-modified group can be obtained. For this reason, any one of the preparation methods may be selected in accordance with the desirable yield or the conditions such as production facilities, purification of raw materials and the like. In addition, in order to improve a quality such as purification or a desirable property of the co-modified organopolysiloxane according to the present invention, any one of the preparation methods may be selected.

As the aforementioned (e) hydrocarbon compound having one reactive unsaturated group in one molecule or the aforementioned linear organopolysiloxane having one reactive unsaturated group in one molecule, a monounsaturated organic compound represented by the following general formula:

$$R'—R^{2'}$$

wherein R' is the same as defined above;
$R^{2'}$ represents a substituted or non-substituted, and linear or branched monovalent hydrocarbon group having 7 to 28 carbon atoms or a linear organosiloxane group represented by the following general formula (2-1):

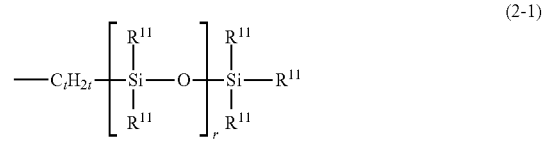

wherein $R^{11}$, t and r are the same as defined above,
or represented by the following general formula (2-2):

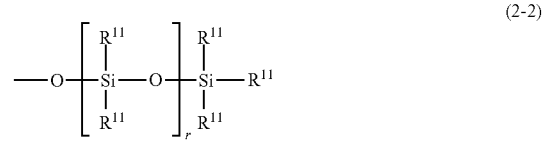

wherein $R^{11}$ and r are as defined above,
is preferred.

As the aforementioned (e) hydrocarbon compound having one reactive unsaturated group in one molecule, a monounsaturated hydrocarbon having 9 to 30 carbon atoms is preferred, and a 1-alkene is more preferable. As examples of 1-alkene, mention may be made of 1-nonene, 1-decene, 1-undecene, 1-dodecene, 1-tridecene, 1-tetradecene and the like. As examples of the aforementioned linear organopolysiloxane having one reactive unsaturated group in one molecule, mention may be made of a dimethylpolysiloxane in which one terminal is capped by a vinyl group, a methylphenylpolysiloxane in which one terminal is capped by a vinyl group, and the like.

The hydrosilylation reaction is preferably carried out in the presence of a catalyst. As examples of the catalyst, mention may be made of a compound such as platinum, ruthenium, rhodium, palladium, osmium, iridium or the like. A platinum compound is, in particular, effective since the catalytic activity thereof is high. As examples of platinum compounds, mention may be made of chloroplatinic acid; platinum metal; a platinum metal-supported carrier such as platinum-supported alumina, platinum-supported silica, platinum-supported carbon black or the like; and a platinum complex such as platinum-vinylsiloxane complex, platinum phosphine complex, platinum-phosphite complex, platinum alcholate catalyst or the like. The usage amount of the catalyst may range from 0.5 to 1,000 ppm as a platinum metal in the case of using a platinum catalyst.

In addition, the aforementioned co-modified organopolysiloxane may be subjected to a hydrogenation treatment in order to ameliorate odor after the reaction due to the residual unsaturated compound. For the hydrogenation treatment, there are a method using a pressurized hydrogen gas and a method using a hydrogen adding agent such as a metal hydride or the like. In addition, in the aforementioned hydrogenation treatment, there are a homogeneous reaction and a heterogeneous reaction. One of these reactions can also be carried out, and the reactions can also be carried out in combination. Considering an advantage in that the used catalyst does not remain in a product, a heterogeneous catalytic hydrogenation reaction using a solid catalyst is most preferable.

As the solid catalyst (hydrogenation catalyst), a common noble metal-based catalyst such as a platinum-based catalyst, a palladium-based catalyst or the like, and a nickel-based catalyst can be used. More particular, as examples thereof, mention may be made of an elemental substance such as nickel, palladium, platinum, rhodium, cobalt or the like, and a catalyst of a combination of plural metals such as platinum-palladium, nickel-copper-chromium, nickel-copper-zinc, nickel-tungsten, nickel-molybdenum or the like. As examples of a catalyst carrier optionally used, mention may be made of activated carbon, silica, silica alumina, alumina, zeolite and the like. In addition, a copper-containing hydrogenation catalyst such as Cu—Cr, Cu—Zn, Cu—Si, Cu—Fe—Al, Cu—Zn—Ti and the like may be mentioned. The form of the aforementioned hydrogenation catalyst cannot be completely determined since the form may vary depending on the type of reactor, and can be appropriately selected from powders, granules, tablets and the like. In addition, the platinum catalyst used in the synthesis step (hydrosilylation reaction) can also be used as it is. The aforementioned hydrogenation catalyst can be used alone or in combination with two or more types thereof.

The hydrogenation treatment can also be used in order to purify a crude product of the co-modified organopolysiloxane obtained by the aforementioned addition reaction. More particularly, the aforementioned purification can be carried out by deodoration due to the hydrogenation treatment in a solvent or without a solvent in the presence of a hydrogenation catalyst. The aforementioned purified product can preferably be used in a cosmetic in which reduction of odor and miscibility with other cosmetic components are desired. In addition, as the pre-step or post-step of the aforementioned deodoration, a stripping treatment in which light products are removed by distillation by contacting a nitrogen gas with respect to a crude product or a hydrogenated product of a co-modified organopolysiloxane can preferably be carried out.

Alternatively, the odor of the crude product of the co-modified organopolysiloxane obtained by the aforementioned addition reaction can also be easily reduced by carrying out a stripping step in which light products are removed by distillation by contacting a nitrogen gas after an unreacted unsaturated product is hydrolyzed by adding an acid substance.

In the aforementioned hydrogenation treatment, acid treatment, and stripping treatment, solvents, reaction conditions, pressure-reduction conditions and the like used in purification of conventional organopolysiloxane copolymers or polyether-modified silicones can be applied and selected without any restrictions.

The co-modified organopolysiloxane of the present invention is useful as a powder treatment agent, a surfactant, a thickening agent or a gelling agent, and can be suitably blended in a preparation for external use, and in particular, in a cosmetic. In addition, powder which has been subjected to a surface treatment with a powder treatment agent comprising the co-modified organopolysiloxane of the present invention are useful as a cosmetic raw material. The mixture of powders and powder treatment agents comprising the aforementioned co-modified organopolysiloxane is also useful as a cosmetic raw material. In addition, a composition which comprises a powder treatment agent comprising the aforementioned co-modified organopolysiloxane, a powder or powders, and an oil agent or agents is, in particular, useful as a cosmetic raw material. In addition, an emulsion composition comprising the co-modified organopolysiloxane of the present invention, water and an oil agent, as well as, a gel composition comprising the co-modified organopolysiloxane of the present invention and an oil agent are useful as a raw material for a preparation for external use, and in particular, a cosmetic.

Hereinafter, the above aspects of the present invention are described in detail.

Powder Treatment Agent

The co-modified organopolysiloxane of the present invention can impart suitable water-repellency by means of orientation on the hydrophilic surface of various types of powders. For this reason, the co-modified organopolysiloxane can be suitably used as a powder treatment agent, and in particular, as a powder surface treatment agent. The blending amount of the aforementioned co-modified organopolysiloxane in the powder treatment agent of the present invention is not particularly restricted as long as a powder treatment effect, and in particular, a powder surface-treatment effect can be exhibited. The blending amount can range from 50 to 100% by weight (mass), preferably ranges from 70 to 100% by weight (mass) and more preferably ranges from 90 to 100% by weight (mass).

The co-modified organopolysiloxane of the present invention can exhibit good affinity with various other components which are hydrophilic or hydrophobic in a cosmetic, and can improve dispersing ability and stability of powders contained in a cosmetic. Therefore, the powder treatment agent and powder surface-treatment agent of the present invention can improve stability of a cosmetic comprising powder(s) and improve homogeneous dispersing ability of the aforementioned powder(s). In addition, the cosmetic comprising powder(s) which has/have been surface-treated with the aforementioned powder surface-treatment agent can exhibit superior stability and the aforementioned powders can be uniformly dispersed in the cosmetic.

In the case of using the co-modified organopolysiloxane of the present invention in the surface treatment of powder(s), the aforementioned co-modified organopolysiloxane may preferably be used in an amount ranging from 0.1 to 10 parts by weight (mass) with respect to 100 parts by weight (mass) of the powder(s). If the amount is below the aforementioned lower limit, an effect by the surface treatment may be insufficient. On the other hand, if the amount exceeds the upper limit, remarkable change of texture in accordance with the increased amount may not be exhibited, and tendency of obtaining a homogenous mixture of the powders and the co-modified organopolysiloxane may be increased.

In addition, the powder(s) may be subjected to a surface treatment in combination with other conventional surface treatment(s). As examples of other conventional surface treatment(s), mention may be made of, for example, treatments with a methylhydrogenpolysiloxane, a silicone resin, a metal soap, a silane coupling agent, an inorganic oxide such as silica, alumina, titanium oxide or the like, a fluorine compound such as a perfluoroalkylsilane, a perfluoroalkyl phosphoric acid ester salt and the like. Therefore, the powder surface treatment agent of the present invention may include the other surface treatment agent(s) in an amount ranging from 0.1 to 50% by weight (mass), preferably ranging from 1 to 30% by weight (mass) and more preferably ranging from 5 to 10% by weight (mass) with respect to the amount of the powder surface treatment agent.

Powder

"Powder" in the present invention is that commonly used as a component of a cosmetic, and includes white and colored pigments and extender pigments. The white and colored pigments are used in coloring a cosmetic, and on the other hand, the extender pigments are used in improvement in feeling on touch of a cosmetic and the like. As the "powder" in the present invention, white or colored pigments and extender pigments which are commonly used in cosmetics can be used without any restrictions. One type of powder may be used, or two or more types of powders are preferably blended.

With respect to powders, there is no restriction on the form thereof (sphere, bar, needle, plate, amorphous, spindle or the like), the particle size (aerosol, microparticle, pigment-grade particle, or the like), and the particle structure (porous, non-porous or the like) thereof. The average primary particle size of the powders preferably ranges from 1 nm to 100 μm.

As examples of powders, mention may be made of, for example, inorganic powders, organic powders, surfactant metal salt powders (metallic soaps), colored pigments, pearl pigments, metal powder pigments and the like. In addition, hybrid products of the aforementioned pigments can also be used.

More particularly, as examples of inorganic powders, mention may be made of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like. As examples of organic powders, mention may be made of polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, polymethylsilsesquioxane spherical powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, microcrystalline fiber powder, starch powder, lauroyl lysine and the like.

As examples of surfactant metal salt powders, mention may be made of zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like.

As examples of colored pigments, mention may be made of inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like, laked pigments of natural pigments such as carminic acid, laccaic acid, carthamin, brazilin, crocin and the like.

As examples of pearl pigments, mention may be made of titanium oxide-coated mica, titanium mica, iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like.

As examples of metal powder pigments, mention may be made of powders of metals such as aluminum, gold, silver, copper, platinum, stainless steel, and the like.

In addition, in the aforementioned powders, a part or all parts thereof may, in particular, preferably be subjected to a surface treatment such as a water-repellent treatment, a hydrophilic treatment or the like. In addition, composited products in which the aforementioned powders are mutually composited may be used. In addition, surface-treated products in which the aforementioned powders have been subjected to a surface treatment with a general oil agent, a silicone compound other than the co-modified organopolysiloxane of the present invention, a fluorine compound, a surfactant, a thickening agent or the like can also be used. One type thereof or two or more types thereof can be used, as necessary.

The water-repellant treatments are not particularly restricted. The aforementioned powders can be treated with various types of water-repellant surface treatment agents. As examples thereof, mention may be made of organosiloxane treatments such as a methylhydrogenpolysiloxane treatment, a silicone resin treatment, a silicone gum treatment, an acryl silicone treatment, a fluorinated silicone treatment and the like; metallic soap treatments such as a zinc stearate treatment and the like; silane treatments such as a silane coupling agent treatment, an alkylsilane treatment and the like; fluorine compound treatments such as a perfluoroalkylsilane treatment, a perfluoroalkyl phosphate treatment, a perfluoro polyether treatment and the like; amino acid treatments such as an N-lauroyl-L-lysine treatment and the like; oil agent treatments such as a squalane treatment and the like; acryl treatments such as an alkyl acrylate treatment and the like. The aforementioned treatments can be used in combination of two or more types thereof.

As the powders, silicone elastomer powders can be used. The silicone elastomer powder is a crosslinked product of a linear diorganopolysiloxane mainly formed from a diorganosiloxane unit (D unit). The silicone elastomer powder can be preferably produced by crosslink-reacting an organohydrogenpolysiloxane having a silicon-binding hydrogen atom at the side chain or the terminal and a diorganopolysiloxane having an unsaturated hydrocarbon group such as an alkenyl group or the like at the side chain or the terminal, in the presence of a catalyst for a hydrosilylation reaction. The silicone elastomer powder has an increased flexibility and elasticity, and exhibits a superior oil-absorbing property, as compared with a silicone resin powder formed from T units and Q units. For this reason, the silicone elastomer powder absorbs sebum on the skin and can prevent makeup running. In addition, when a surface treatment is carried out by the aforementioned co-modified organopolysiloxane, a moisturized feeling on touch can be imparted without reducing a suede-like feeling on touch of the silicone elastomer powder. In addition, in the case of blending the aforementioned co-modified organopolysiloxane together with the silicone elastomer powder in a cosmetic, dispersion stability of the aforementioned powder in the entire cosmetic can be improved, and a stable cosmetic over time can be obtained.

The silicone elastomer powders can be in various forms such as a spherical form, a flat form, an amorphous form and the like. The silicone elastomer powders may be in the form of an oil dispersant. In the cosmetic of the present invention, silicone elastomer powders in the form of particles, which have a primary particle size observed by an electron microscope and/or an average primary particle size measured by a laser diffraction/scattering method ranging from 0.1 to 50 µm, and in which the primary particle is in a spherical form, can be preferably blended. In addition, the silicone elastomer constituting the silicone elastomer powders may have a hardness preferably not exceeding 80, and more preferably not exceeding 65, when measured by means of a type A durometer according to JIS K 6253 "Method for determining hardness of vulcanized rubber or thermoplastic rubber".

The silicone elastomer powders may be subjected to a surface treatment with a silicone resin, silica or the like. As examples of the aforementioned surface treatments, mention may be made of, for example, those described in Japanese Unexamined Patent Application, First Publication No. H02-243612; Japanese Unexamined Patent Application, First Publication No. H08-12545; Japanese Unexamined Patent Application, First Publication No. H08-12546; Japanese Unexamined Patent Application, First Publication No. H08-12524; Japanese Unexamined Patent Application, First Publication No. H09-241511; Japanese Unexamined Patent Application, First Publication No. H10-36219; Japanese Unexamined Patent Application, First Publication No. H11-193331; Japanese Unexamined Patent Application, First Publication No. 2000-281523 and the like. As the silicone elastomer powders, crosslinking silicone powders listed in "Japanese Cosmetic Ingredients Codex (JCIC)" correspond thereto. As commercially available products, there are Trefil E-506S, Trefil E-508, 9701 Cosmetic Powder, and 9702 Powder, manufactured by Dow Corning Toray Co., Ltd., and the like. As examples of the surface treatment agents, mention may be made of methylhydrogenpolysiloxane, silicone resins, metallic soap, silane coupling agents, inorganic oxides such as silica, titanium oxide and the like and fluorine compounds such as perfluoroalkylsilane, perfluoroalkyl phosphoric ester salts and the like.

A mixture of the aforementioned co-modified organopolysiloxane and powder(s) can be obtained by mixing an excess amount of the co-modified organopolysiloxane and powder(s). The aforementioned mixture is in the form of a powder dispersion in the co-modified organopolysiloxane. The blending amount of the powder(s) in the aforementioned mixture is not particularly restricted, and may preferably range from 50 to 99% by weight (mass) and more preferably may range from 80 to 90% by weight (mass) with respect to the total amount of the mixture.

The powder which has been subjected to a surface treatment with a powder surface treatment agent comprising the aforementioned co-modified organopolysiloxane, or a mixture of the aforementioned co-modified organopolysiloxane and powder(s) can provide powder(s) which can well be dispersed in a cosmetic. Therefore, they can be preferably used as a cosmetic raw material. In addition, a cosmetic obtained by using them as a raw material can exhibit superior stability.

A composition comprising a powder treatment agent comprising the aforementioned co-modified organopolysiloxane, powder(s) and oil agent(s) can also be preferably used as a cosmetic raw material. The powder(s) in the aforementioned composition can be stably dispersed. For this reason, the aforementioned composition can exhibit increased stability and superior storage stability.

Oil Agent

The "oil agent" in the present invention is commonly used as a component of a cosmetic, and is not particularly restricted. The oil agent is usually in the form of a liquid at room temperature, and may be in the form of a solid such as a wax or in the form of a gum or a paste which has an increased viscosity and is thickened.

The oil agent is preferably at least one type of a liquid at 5 to 100° C., selected from the group consisting of a silicone oil, a non-polar organic compound and a low polar organic compound.

The silicone oils are hydrophobic, and the molecular structure thereof may be a cyclic, linear or branched structure. The viscosity of the silicone oils at 25° C. usually ranges from 0.65 to 100,000 mm$^2$/s and preferably ranges from 0.65 to 10,000 mm$^2$/s.

As examples of the aforementioned silicone oils, mention may be made of, for example, linear organopolysiloxanes, cyclic organopolysiloxanes, and branched organopolysiloxanes. Among these, volatile, linear organopolysiloxanes, cyclic organopolysiloxanes, and branched organopolysiloxanes are preferred.

As the linear organopolysiloxanes, cyclic organopolysiloxanes, and branched organopolysiloxanes, for example, organopolysiloxanes represented by the following general formulae: (5), (6) and (7):

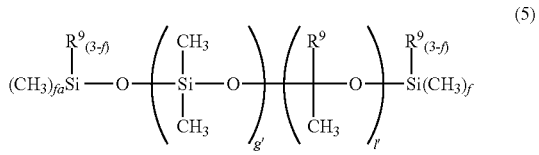

(5)

wherein
$R^9$ is a hydrogen atom, a hydroxyl group or a group selected from monovalent non-substituted or fluorine- or amino-substituted, $C_{1-30}$ alkyl groups, aryl groups, alkoxy groups and groups represented by $(CH_3)_3SiO\{CH_3)_2SiO\}_1Si(CH_3)_2CH_2CH_2$—,
wherein l is an integer ranging from 0 to 1,000;
f is an integer ranging from 0 to 3;
g' is an integer ranging from 0 to 1,000; and
l' is an integer ranging from 0 to 1,000, with the proviso that $1 \leq g'+l' \leq 2,000$,

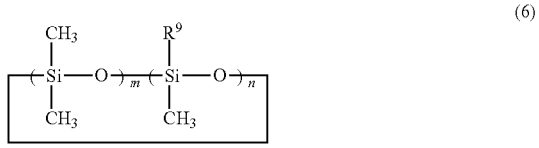

(6)

wherein
$R^9$ is the same as defined above;
m is an integer ranging from 0 to 8; and
n is an integer ranging from 0 to 8, with the proviso that $3 \leq m+n \leq 8$, $$R^9{}_{(4-p)}Si(OSiCH_3)_q \quad (7)$$

wherein
$R^9$ is the same as defined above;
p is an integer ranging from 1 to 4; and
q is an integer ranging from 0 to 500,
can be used.

As examples of monovalent non-substituted or fluorine- or amino-substituted $C_{1-30}$ alkyl groups, aryl groups, and alkoxy groups having 1 to 30 carbon atoms, mention may be made of, for example, linear or branched alkyl groups having 1 to 30 carbon atoms such as a methyl group, an ethyl group, a propyl group, a butyl group, a pentyl group, a hexyl group, a heptyl group, an octyl group, a decyl group, a dodecyl group and the like; cycloalkyl groups having 3 to 30 carbon atoms such as a cyclopentyl group, a cyclohexyl group and the like; aryl groups having 6 to 30 carbon atoms such as a phenyl group, a tolyl group, a xylyl group, a naphthyl group and the like; alkoxy groups having 1 to 30 carbon atoms such as a methoxy group, an ethoxy group, a propoxy group and the like; and substituted groups thereof, in which hydrogen atoms binding to carbon atoms of the aforementioned groups are at least partially substituted by a fluorine atom or an amino group. A non-substituted alkyl group or aryl group is preferred, and a non-substituted alkyl group or aryl group having 1 to 6 carbon atoms or aryl group is further preferred. A methyl group, an ethyl group or a phenyl group is, in particular, preferred.

As examples of linear organopolysiloxanes, mention may be made of a dimethylpolysiloxane in which both molecular terminals are capped with trimethylsiloxy groups (dimethylsilicone with a low viscosity such as 2 mPa·s or 6 mPa·s to dimethylsilicone with a high viscosity such as 1,000,000 mPa·s), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl(trimethylsiloxy)siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl(3,3,3-trifluoropropyl)siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone, dimethiconol and the like.

More particularly, as examples of cyclic organopolysiloxanes, mention may be made of hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(lauroyl)-3-aminopropyl)tetramethylcyclotetrasiloxane and the like.

As examples of branched organopolysiloxanes, mention may be made of methyltristrimethylsiloxysilane, ethyltristrimethylsiloxysilane, propyltristrimethylsiloxysilane, tetrakistrimethylsiloxysilane, phenyltristrimethylsiloxysilane and the like.

As the non-polar organic compounds and the low polar organic compounds, a hydrocarbon oil and a fatty acid ester oil are preferred. They are widely used, in particular, as a base material of a makeup cosmetic. The co-modified organopolysiloxane of the present invention exhibits a superior dispersing property with respect to these non-silicone-based oil agents. For this reason, hydrocarbon oils and fatty acid ester oils can be stably blended in cosmetics, and a moisturizing property obtained by these non-silicone-based oil agents can be maintained. Therefore, the aforementioned co-modified organopolysiloxane can improve stability of the aforementioned non-silicone-based oil agents in cosmetics over time.

By using the aforementioned silicone oils in combination with the hydrocarbon oils and/or fatty acid ester oils, advantages can be obtained in that moisture on the skin can be maintained, and a moisturizing sensation (also referred to as "moisturizing feeling on touch") such as moisturizing skin or hair and smooth feeling on touch, in addition to a refreshing feeling on touch which the silicone oils inherently possess, can be provided in cosmetics, and stability over time of cosmetics is not impaired. In addition, use of the cosmetics comprising the aforementioned silicone oils in combination with the hydrocarbon oils and/or fatty acid ester oils provides advantages in that these moisturizing components (the hydrocarbon oils and/or fatty acid ester oils) can be stably and uniformly applied on the skin or hair, the moisturizing effects of the moisturizing components on the skin can be increased, and therefore, superior smoothness and a superior moisturizing feeling can be provided, as compared with cosmetics comprising only non-silicone oils (the hydrocarbon oils and/or fatty acid ester oils).

As examples of hydrocarbon oils, mention may be made of liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene and the like.

As examples of fatty acid ester oils, mention may be made of hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-hexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), diisopropyl dimmer dilinoleate, diisostearyl dimmer dilinoleate, di(isostearyl/phytosteryl) dimmer dilinoleate, (phytosteryl/behenyl) dimmer dilinoleate, (phytosteryl/isostearyl/cetyl/stearyl/behenyl) dimmer dilinoleate, dimmer dilinoleyl dimmer dilinoleate, dimmer dilinoleyl diisostearate, dimmer dilinoleyl hydrogenated rosin condensate, dimmer dilinoleic acid hardened castor oil, hydroxyalkyl dimmer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri (caprylate/caprate), glyceryl tri(caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

As the low polar organic compound, a higher alcohol having 10 to 30 carbon atoms can be used. The aforementioned higher alcohol is a saturated or unsaturated monovalent aliphatic alcohol, and the moiety of the hydrocarbon group thereof may be linear or branched, but a linear one is preferred. As examples of higher alcohols having 10 to 30 carbon atoms, mention may be made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol and the like. In the present invention, use of a higher alcohol having a melting point ranging from 40 to 80° C. or use of a combination of plural higher alcohols so as to have a melting point thereof ranging from 40 to 70° C. is preferred.

In the present invention, in addition to the aforementioned oil agents, fats and oils, higher fatty acids, fluorine-based oils and the like may be used as other oil agents, and they may be used in combination of two or more types thereof. In particular, fats and oils derived from vegetables provide a healthy image derived from natural products and exhibit a superior moisture-retaining property and superior compatibility on the skin. For this reason, they are preferably used in a cosmetic of the present invention.

As examples of natural animal or vegetable fats and oils and semi-synthetic fats and oils, mention may be made of avocado oil, linseed oil, almond oil, ibota wax, perilla oil, olive oil, cacao butter, kapok wax, kaya oil, carnauba wax, liver oil, candelilla wax, beef tallow, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, olive oil, squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, POE cholesterol ether, monostearyl glycerol ether (batyl alcohol), monooleyl glycerol ether (selachyl alcohol), egg yolk oil and the like, with the proviso that POE means polyoxyethylene.

As examples of higher fatty acids, mention may be made of, for example, lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

As examples of fluorine-based oils, mention may be made of perfluoro polyether, perfluorodecalin, perfluorooctane and the like.

The blending amount of the oil agent(s) as the cosmetic raw material in the aforementioned composition is not particularly restricted, and may preferably range from 0.1 to 50% by weight (mass) and more preferably may range from 0.5 to 25% by weight (mass) with respect to the amount of the cosmetic raw material.

The aforementioned cosmetic raw material(s) can be used by being blended in cosmetics.

The cosmetic of the present invention can include the aforementioned co-modified organopolysiloxane and the aforementioned powder(s), derived from the aforementioned cosmetic raw material(s), as essential components, and can exhibit a superior dispersing property of the aforementioned powder(s). Therefore, the cosmetic of the present invention can exhibit superior stability over time and has a superior sensation during use.

The blending amount of the powder(s) in the cosmetic of the present invention may preferably range from 0.1 to 99% by weight (mass) in the total amount of the cosmetic. In particular, the blending amount in the case of a powdery solid cosmetic may preferably range from 80 to 99% by weight (mass) in the total amount of the cosmetic since the powder(s) are used as the base material of the cosmetic.

Surfactant

The co-modified organopolysiloxane of the present invention possesses a sugar alcohol-containing organic group which is hydrophilic and a long-chain hydrocarbon group which is hydrophobic in one molecule, and for this reason, the co-modified organopolysiloxane can be preferably used as a surfactant. The blending amount of the aforementioned co-modified organopolysiloxane in the surfactant of the present invention is not particularly restricted as long as a surface active effect can be exhibited. The amount can range, for example, from 50 to 100% by weight (mass), preferably ranges from 70 to 100% by weight (mass) and more preferably ranges from 90 to 100% by weight (mass) with respect to the total amount of the surfactant.

The co-modified organopolysiloxane of the present invention can constitute an emulsion composition, together with water and oil agent(s). The aforementioned emulsion composition can be in the form of an oil-in-water emulsion or a water-in-oil emulsion.

The co-modified organopolysiloxane of the present invention can exhibit a superior emulsifying property, and a particle size of the dispersion phase can be reduced. Therefore, an emulsion obtained by using the aforementioned co-modified organopolysiloxane can have a reduced particle size of the dispersion phase in the continuous phase, can have a homogenous outer appearance, and can be stable.

Water is not particularly restricted as long as it does not include any harmful components for human bodies and is clean. As examples thereof, mention may be made of tap water, purified water, and mineral water. In addition, in the emulsion composition of the present invention, the blending amount of water preferably ranges from 2 to 98% by weight (mass), in the case in which the total amount of all components of the emulsion is 100% by weight (mass). In a cosmetic in the form of a gel emulsion, optional components which are water soluble may be previously blended in water.

As the aforementioned oil agent(s), the same one(s) as described above can be used. The oil agent(s) may preferably be at least one type of compound which is in the form of a liquid at 5 to 100° C., and can be selected from the group consisting of silicone oils, non-polar organic compounds and low polar organic compounds.

The form of the emulsion may be not only an oil-in-water emulsion or water-in-oil emulsion, but also a multiple emulsion or microemulsion thereof. The form of the emulsion (oil-in-water type or water-in-oil type) and the particle size of the emulsion can be appropriately selected or adjusted.

In the case of the emulsion composition of the present invention in the form of an oil-in-water emulsion composition, the dispersion phase of the aforementioned composition is formed from particles of oil agents emulsified by the aforementioned co-modified organopolysiloxane. The average particle size thereof can be measured by a conventional measurement device using a laser diffraction/scattering method or the like. The cosmetic in the form of an oil-in-water emulsion may be a transparent microemulsion in which the average particle size of the dispersion phase measured is 0.1 μm or less, or may be a milky emulsion having a large particle size so that the average particle size exceeds 10.0 μm. In addition, in order to improve stability and transparency of the outer appearance of the emulsion, the emulsion particles can be miniaturized. In particular, in order to improve the adhesive property with respect to the hair or skin or sensation during use, an emulsion having an average particle size ranging from 0.5 to 20 μm can be selected, and is preferred.

The emulsion composition in the form of an oil-in-water emulsion or a water-in-oil emulsion can be produced by mixing components of the aforementioned cosmetic using a mechanical force by means of an apparatus such as a homomixer, a paddle mixer, a Henschel mixer, a homodisper, a colloid mill, a propeller stirrer, a homogenizer, an in-line type continuous emulsifier, an ultrasonic emulsifier, a vacuum kneader or the like.

The aforementioned surfactant or the emulsion composition can be used by blending preferably in a preparation for external use, and in particular, a cosmetic.

The preparation for external use, and in particular, the cosmetic of the present invention essentially comprises the aforementioned co-modified organopolysiloxane, and superior stability for dispersion of the dispersion phase can be exhibited. Therefore, the cosmetic of the present invention can exhibit superior stability over time, can have a uniform outer appearance, and can exhibit a superior sensation during use.

The preparations for external use, and in particular, cosmetics of the present invention, may comprise one or more types of other surfactants. The other surfactants can be selected from the group consisting of anionic surfactants, cationic surfactants, nonionic surfactants, amphoteric surfactants and semi-polar surfactants.

The blending amount of the other surfactants in the preparation for external use, and in particular, the cosmetic of the present invention is not particularly restricted. In order to improve a cleansing property, the other surfactants can be blended in an amount ranging from 0.1 to 90% by weight (mass) in the total amount of the preparation for external use. In view of a cleansing property, the amount is preferably 25% by weight (mass) or more.

As examples of anionic surfactants, mention may be made of saturated or unsaturated fatty acid salts such as sodium laurate, sodium stearate, sodium oleate, sodium linoleate and the like; alkylsulfuric acid salts; alkylbenzenesulfonic acids such as hexylbenzenesulfonic acid, octylbenzenesulfonic acid, dodecylbenzenesulfonic acid and the like, as well as salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamidesulfuric acid salts; alkyl- or alkenylphosphoric acid salts; alkylamidephosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. As examples of salts, mention may be made of alkali metal salts such as a sodium salt and the like, alkaline earth metal salts such as a magnesium salt and the like, alkanolamine salts such as a triethanolamine salt and the like, and an ammonium salt.

As examples of cationic surfactants, mention may be made of alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE) oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, stearic acid diethylaminoethylamide, stearic dimethylaminopropylamide, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

As examples of nonionic surfactants, mention may be made of polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethylene glycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. A polyoxyalkylene-modified silicone, a polyglycerol-modified silicone, or a glycerol-modified silicone in which an alkyl branch, a linear silicone branch, a siloxane dendrimer branch or the like may be possessed together with a hydrophilic group at the same time, if necessary, can also be preferably used.

The co-modified organopolysiloxane of the present invention possesses a hydrophilic moiety and a hydrophobic moiety in a molecule, and for this reason, the co-modified organopolysiloxane has a function as a dispersant. For this reason, in the case of using the co-modified organopolysiloxane together with a silicone-based nonionic surfactant, the organopolysiloxane may function as an auxiliary agent for improving stability of the nonionic surfactant and improve stability of the entire preparation. In particular, the aforementioned co-modified organopolysiloxane is preferably used together with a polyoxyalkylene-modified silicone, a polyglycerol-modified silicone, or a glycerol-modified silicone.

As examples of amphoteric surfactants, mention may be made of imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. More particularly, as examples thereof, mention may be made of imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt and the like; alkylbetaine-type amphoteric surfactants such as lauryl dimethylaminoacetic acid betaine, myristyl betaine and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyl dimethylamino acetic acid betaine, palmitic amidopropyl dimethylamino acetic acid betaine, stearic amidopropyl dimethylamino acetic acid betaine, oleic amidopropyl dimethylamino acetic acid betaine and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine and the like.

As examples of semi-polar surfactants, mention may be made of alkylamine oxide-type surfactants, alkylamine oxides, alkylamide amine oxides, alkylhydroxyamine oxides and the like. Alkyldimethylamine oxides having 10 to 18 carbon atoms, alkoxyethyl dihydroxyethylamine oxides having 8 to 18 carbon atoms and the like are preferably used. More particularly, as examples thereof, mention may be made of dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyl dimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

Thickening Agent or Gelling Agent

The co-modified organopolysiloxane of the present invention can also be used as a thickening agent or a gelling agent, and in particular, as a thickening agent or a gelling agent of an oil agent. The blending amount of the aforementioned co-modified organopolysiloxane in the thickening agent or the gelling agent of the present invention is not particularly restricted as long as a thickening effect or a gelling effect is exhibited. For example, the blending amount thereof can range from 50 to 100% by weight (mass), preferably ranges from 70 to 100% by weight (mass) and more preferably ranges from 90 to 100% by weight (mass) with respect to the total amount of the thickening agent or the gelling agent of the present invention.

Herein, the technical effect of "thickening" and the technical effect of "gelling" with respect to the oil agent cannot necessarily be clearly differentiated from each other since they involve a continuous phenomenon. In general, it is referred to as "thickening" when the viscosity of an oil agent having fluidity which is in the form of a liquid at room temperature is increased. In addition, a phenomenon in which the aforementioned thickening further proceeds to be a viscous fluid in the form of a mizuame (water candy), a cream or a paste, and subsequently, the oil agent almost loses fluidity to be in the form of a gel or a semi-solid or a soft solid, is referred to as "gelling". The co-modified organopolysiloxane of the present invention can be preferably used as a thickening agent or a gelling agent with respect to the oil agent components by selecting the usage amount or the structure thereof. For example, if the co-modified organopolysiloxane of the present invention is blended in a small amount with respect to the oil agent, the organopolysiloxane functions as a thickening agent. On the other hand, if it is blended in a large amount, the oil agent can be gelled.

In the field of a preparation for external use, and in particular, a cosmetic, by thickening or gelling the oil agent, large effects and changes in the outer appearance thereof, the blending system, sensation during use and the form can be obtained. For this reason, the thickening/gelling technology with respect to oil agents is highly important. In addition, the form of a cosmetic can be freely controlled from a liquid form to a mizuame, cream, paste, gel or solid form by a manufacturer of a cosmetic. For this reason, the thickening or gelling technology with respect to oil agents corresponds to an extremely important technology.

The co-modified organopolysiloxane of the present invention can gel the oil agents. On the other hand, in the form in which gelation is not preferred, the co-modified organopolysiloxane can also be used as a thickening agent with respect to the oil agents. Therefore, the co-modified organopolysiloxane of the present invention is useful with respect to an oil agent for use in a preparation for external use, and in particular in a cosmetic. The degree of gelation can be controlled by the usage amount of the co-modified organopolysiloxane. In addition, the co-modified organopolysiloxane of the present invention exhibits superior miscibility with respect to various types of oil agents. For this reason, even in the case of mixing with a non-silicone oil, the co-modified organopolysiloxane possesses an advantage in that the problem of phase separation would not occur.

As the aforementioned oil agent, the same oil agents as described above can be used. The oil agent is preferably at least one type of an oil agent which is in the form of a liquid at 5 to 100° C., and is preferably selected from the group consisting of a silicone oil, a non-polar organic compound and a low-polar organic compound.

A gel composition can be produced by mixing the thickening agent or the gelling agent of the present invention with an oil agent or agents by means of a conventional means to thicken or gel the aforementioned oil agent. In the aforementioned gel composition, other components can be further blended. The aforementioned gel composition can be stably present, and for this reason, superior storage stability can be exhibited. In addition, as described below, the gel composition can be used as a composition (a premix) for producing a cosmetic in order to prepare an aqueous composition.

In addition, an oil agent contained in a preparation for external use can be thickened or gelled by adding the thickening agent or the gelling agent of the present invention to a previously prepared preparation for external use, and in particular, a cosmetic, and subsequently uniformly dispersing them. In particular, by thickening or gelling the oil agent contained in a cosmetic, the viscosity or hardness of the cosmetic can be adjusted to an appropriate degree, the outer appearance, the blending property and sensation during use can be improved, and a desirable formulation or cosmetic form can be obtained.

The blending amount or blending ratio of the thickening agent or gelling agent of the present invention is not particularly restricted, and may preferably range from 1 to 99% by weight (mass) and more preferably may range from 5 to 40% by weight (mass), with respect to the total weight (mass) of the oil agent(s). The degree of thickening varies in accordance with the blending amount thereof into the oil agent(s). For this reason, the viscosity of the whole preparation for external use containing the oil agent, and in particular, the hardness of the gel composition (which is a property of the preparation for external use, and in particular, the cosmetic, also referred to as viscoelasticity or a texture with elasticity of the gel), can be controlled within a preferable range.

The co-modified organopolysiloxane of the present invention can be used as a thickening agent or a gelling agent for oil agent(s) as it is alone. In the case of using this together with powders, in addition to a thickening/gelling effect with respect to the oil agent(s), an effect of stably and uniformly dispersing the powder(s) in the obtained thickened gel composition can be exhibited. In particular, a dispersion, in which powder(s) is/are dispersed in an oil, exhibiting superior stability so that clumping or sedimentation of the powders in the mixed oil agent system does not occur can be provided. In addition, a superior cosmetic effect and natural skin feeling without an unpleasant sensation can be continued about one day even after the aforementioned powder-in-oil dispersion is applied to the skin, and a superior dispersion/fixing function can be exhibited.

As the aforementioned powders, the same powders as described above can be used.

The blending amount of the powders can be selected in accordance with the form of the preparation for external use, and may preferably range from 0.1 to 99% by weight (mass) of the total amount of the gel composition.

The aforementioned thickening agent or gelling agent, as well as the aforementioned gel composition can be used by preferably blending in a preparation for external use, and in particular, a cosmetic.

The gel composition containing the powder(s) can also be used as a gel cosmetic as it is. The blending amount of the powders in the case of a gel cosmetic may preferably range from 10 to 50% by weight (mass) in the total amount of the cosmetic. In addition, in the case of using a cosmetic in the form of a solid gel having reduced fluidity, the powder(s) can be blended in an amount ranging from 50 to 80% by weight (mass) of the total amount of the cosmetic.

In particular, a preparation for external use, and preferably an emulsion cosmetic, in any form having a reduced viscosity, as compared with a paste, cream, emulsion form, can be easily obtained by mixing and diluting with water and at least one type of alcohol selected from the group consisting of lower alcohols and polyhydric alcohols.

As examples of lower alcohols, mention may be made of ethanol, isopropanol, n-propanol, t-butanol, s-butanol and the like. As examples of polyhydric alcohols, mention may be made of divalent alcohols such as 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl hexylene glycol, octylene glycol and the like; trivalent alcohols such as glycerol, trimethylol propane, 1,2,6-hexanetriol and the like; polyhydric alcohols having 4 or more valences such as pentaerythritol, xylitol and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol and the like. In addition to the aforementioned low-molecule polyhydric alcohols, polyhydric alcohol polymers such as diethylene glycol, dipropylene glycol, triethylene glycol, propylene glycol, tetraethylene glycol, diglycerol, polyethylene glycol, triglycerol, tetraglycerol, polyglycerol and the like may be mentioned.

The gel composition containing the aforementioned alcohol may have advantages in that the self-emulsification property can be further improved, and studying conditions in detail, which is essential in the case of producing a stable water-in-oil emulsion cosmetic, is not almost necessary.

The alcohol is preferably ethanol, isopropanol, 1,3-butylene glycol, sorbitol, dipropylene glycol, glycerol, or polyethylene glycol, and can enhance stability of the emulsified product. Among these, 1,3-butylene glycol, sorbitol, dipropylene glycol, glycerol, and polyethylene glycol possess an effect of retaining moisture, and for this reason, they are preferred. In addition, use of a combination between ethanol and an alcohol other than ethanol in a weight (mass) ratio ranging from 5/5 to 9.9/0.1 is also preferred in view of the self-emulsification property of the gel composition. In addition, the weight (mass) ratio of ethanol and an alcohol other than ethanol of 6/4 or more is, in particular, preferred in view of the self-emulsification property.

The gel composition of the present invention can be used as a composition (premix) for use in the preparation of a hydrous preparation for external use, and in particular, a hydrous cosmetic. Thereby, a more stable hydrous cosmetic can be formed by means of a simple stirrer or mixer without using a specific high-pressure emulsifier. For this reason, there is an advantage in that it is not necessary to study the optimization for emulsification and dispersion conditions. In addition, a cosmetic produced using the gel composition of the present invention is a hydrous cosmetic, and in particular, a water-in-oil emulsion cosmetic, which can exhibit superior stability over time, superior feeling on touch, a superior moisture-retaining property, superior outer appearance and the like, and in which each of the aforementioned components can be stably and easily blended.

Preparation for External Use and Cosmetic

The preparation for external use, and in particular, the cosmetic of the present invention essentially comprises the aforementioned co-modified organopolysiloxane, and the blending amount thereof is not particularly restricted. The blending amount of the co-modified organopolysiloxane may preferably range from 0.1 to 20% by weight (mass), and more preferably may range from 1 to 10% by weight (mass) of the total amount of the preparation for external use.

The preparation for external use, and in particular, the cosmetic of the present invention may further comprise an oil agent. As the aforementioned oil agent, the same oil agent as described above can be used. The oil agent is preferably at least one oil agent, which is in the form of a liquid at 5 to 100° C., and is selected from the group consisting of a silicone oil, a non-polar organic compound and a low-polar organic compound.

The blending amount of the oil agent(s) in the preparation for external use of the present invention is appropriately selected in accordance with the forms, types, application parts and characteristics valued, and may preferably range from 0.1 to 95% by weight (mass) and more preferably may range from 0.5 to 75% by weight (mass), of the total amount of the preparation for external use. In addition, two or more types of oil agents which have independently different viscosities and the like may preferably be used.

In addition, the preparation for external use of the present invention may further comprise water. Therefore, the preparation for external use of the present invention can be in the form of an oil-in-water emulsion or a water-in-oil emulsion. In this case, the preparation for external use of the present invention exhibits superior emulsion stability and a superior sensation during use.

The preparation for external use of the present invention can comprise various other raw materials. The aforementioned raw materials are preferably hydrophobic so that they are completely insoluble in water at room temperature or the solubility thereof with respect to 100 g of water is below 1% by weight (mass).

As examples of the aforementioned raw materials, mention may be made of, for example, a silicone resin, a silicone elastomer, a water-soluble polymer, other surfactants, other oil-based gelling agents, an organo-modified clay mineral, a silicone gum, an organo-modified silicone, an ultraviolet controlling component, and the like.

The silicone resin is an organopolysiloxane with a highly branched molecular structure, a net-like molecular structure or a cage-like molecular structure, and may be in the form of a liquid or solid at room temperature. Any silicone resins usually used in preparations for external use can be used unless they are contrary to the purposes of the present invention. In the case of a solid silicone resin, the silicone resin may be in the form of particles such as spherical powders, scale powders, needle powders platy flake powders (including platy powders having an aspect ratio of particles and the outer appearance which are generally understood as a plate form) or the like. In particular, silicone resin powders containing a monoorganosiloxy unit (T unit) and/or a siloxy unit (Q unit) described below are preferably used.

Blending the silicone resin together with the co-modified organopolysiloxane of the present invention is useful, since the miscibility with the oil agents and the uniformly dispersing property can be improved, and at the same time, an effect of improving sensation during use such as uniform adhesiveness with respect to the part to be applied, obtained in accordance with blending the silicone resin can be obtained.

As examples of the solid silicone resins, mention may be made of, for example, MQ resins, MDQ resins, MTQ resins, MDTQ resins, TD resins, TQ resins, or TDQ resins comprising any combinations of a triorganosiloxy unit (M unit) (wherein the organo group is a methyl group alone, or a methyl group in combination with a vinyl group or a phenyl group), a diorganosiloxy unit (D unit) (wherein the organo group is a methyl group alone, or a methyl group in combination with a vinyl group or a phenyl group), a monoorganosiloxy unit (T unit) (wherein the organo group is a methyl group, a vinyl group or a phenyl group), and a siloxy unit (Q unit). In addition, as other examples thereof, mention may be made of trimethylsiloxysilicic acid, polyalkylsiloxysilicic acid, trimethylsiloxysilicic acid containing dimethylsiloxy units and alkyl(perfluoroalkyl) siloxysilicic acid. The aforementioned silicone resins are preferably oil soluble, and, in particular, preferably are soluble in a volatile silicone.

The silicone resin preferably used in the preparation for external use of the present invention possesses at least a monoorganosiloxy unit (T unit) and/or a siloxy unit (Q unit). The aforementioned silicone resin may preferably be blended in an amount ranging from 0.1 to 10% by weight (mass) with respect to the total amount of the preparation for external use. The aforementioned silicone resins having branched units have a net-like structure. In the case of applying these to the skin, hair or the like, a uniform film can be formed. Thereby, a protecting effect with respect to dryness and low temperatures can be provided, and make-up running occurred together with sebum by perspiration can be prevented. In addition, the aforementioned silicone resins having the branched units can tightly adhere to the skin, hair or the like, and can provide glossiness and a transparent impression to the skin, hair or the like.

In particular, a phenyl silicone resin with an increased refractive index which has an increased content of a phenyl group (such as 217 Flake Resin manufactured by Dow Corning Toray Co., Ltd.) can easily form silicone resin powders in the form of flakes. In the case of blending the powders in a preparation for external use, a brilliant transparent impression can be provided to the skin and hair.

The silicone elastomer can be blended as the aforementioned silicone elastomer powders or a crosslinking organopolysiloxane.

The aforementioned silicone elastomer powders can be used in the preparation for external use of the present invention, in the form of an aqueous dispersion. As examples of commercially available products of the aforementioned aqueous dispersions, mention may be made of, for example, "BY 29-129" and "PF-2001 PIF Emulsion" manufactured by Dow Corning Toray Co., Ltd., and the like. By blending an aqueous dispersion (=suspension) of the aforementioned silicone elastomer powders, sensation during use of the preparations for external use, and in particular, oil-in-water emulsion preparations for external use can be further improved.

The crosslinking organopolysiloxane preferably has a structure in which an organopolysiloxane chain is three-dimensionally crosslinked by a reaction with a crosslinking component formed from a polyether unit, an alkylene unit having 4 to 20 carbon atoms, and an organopolysiloxane unit, or the like.

The crosslinking organopolysiloxane can be particularly obtained by addition-reacting an organohydrogenpolysiloxane having silicon-binding hydrogen atoms, a polyether compound having unsaturated bonds at both terminals of the molecular chain, an unsaturated hydrocarbon having more than one double bonds in a molecule, and an organopolysiloxane having more than one double bond in a molecule. Here, the crosslinking organopolysiloxane may or may not have a modifying functional group such as an unreacted silicon-binding hydrogen atom, an aromatic hydrocarbon group such as a phenyl group or the like, a long chain alkyl group having 6 to 30 carbon atoms such as an octyl group, a polyether group, a carboxyl group, a silylalkyl group having the aforementioned carbosiloxane dendrimer structure or the like, and can be used without restrictions of physical modes and preparation methods such as dilution, properties and the like.

As one example, the aforementioned crosslinking organopolysiloxane can be obtained by addition-reacting an organohydrogenpolysiloxane which is formed from a structure unit selected from the group consisting of a $SiO_2$ unit, a $HSiO_{1.5}$ unit, a $R^b SiO_{1.5}$ unit, a $R^b HSiO$ unit, a $R^b_2 SiO$ unit, a $R^b_3 SiO_{0.5}$ unit and a $R^b_2 HSiO_{0.5}$ unit, wherein Rb is a substituted or non-substituted monovalent hydrocarbon group having 1 to 30 carbon atoms, excluding an aliphatic unsaturated group, and a part of Rb is a monovalent hydrocarbon group having 8 to 30 carbon atoms, and at the same time, includes 1.5 or more, on average, of hydrogen atoms binding to the silicon atom in the molecule, with a crosslinking component selected from the group consisting of a polyoxyalkylene compound having unsaturated hydrocarbon groups at both terminals of the molecular chain, a polyether compound such as a polyglycerol compound, a polyglycidyl ether compound or the like, an unsaturated hydrocarbon which is an α,ω-diene represented by the following general formula: $CH_2=CH-C_rH_{2r}-CH=CH_2$, wherein r is an integer ranging from 0 to 26, and an organopolysiloxane which is formed from a $SiO_2$ unit, a $(CH_2=CH)SiO_{1.5}$ unit, a $R^cSiO_{1.5}$ unit, a $R^c(CH_2=CH)SiO$ unit, a $R^c_2SiO$ unit, a $R^c_3SiO_{0.5}$, and a $R^c_2(CH_2=CH)SiO_{0.5}$, wherein $R^b$ is a substituted or non-substituted monovalent hydrocarbon group having 1 to 30 carbon atoms, excluding an aliphatic unsaturated group, and includes 1.5 or more, on average, of vinyl groups binding to the silicon atom. The aforementioned modifying functional group can be introduced by carrying out an addition reaction with respect to the unreacted hydrogen atoms binding to the silicon atom in a molecule. For example, 1-hexene is reacted with a crosslinking organopolysiloxane having an unreacted hydrogen atom binding to the silicon atom, and thereby, a hexyl group which is an alkyl group having 6 carbon atoms can be introduced thereinto.

The aforementioned crosslinking organopolysiloxanes can be used without restrictions of physical modes and preparation methods such as dilution, properties and the like. As particularly preferable examples thereof, mention may be made of α,ω-diene crosslinking silicone elastomers (as commercially available products, DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation in the USA) described in U.S. Pat. No. 5,654,362. In the same manner as described above, as examples of partially crosslinking organopolysiloxane polymers, mention may be made of (dimethicone/vinyldimethicone) crosspolymer, (dimethicone/phenylvinyldimethicone) crosspolymer, (PEG-8 to 30/C6 to C30 alkyldimethicone) crosspolymer, (vinyldimethicone/C6 to C30 alkyldimethicone) crosspolymer, (dimethicone/polyglycerol) crosspolymer and the like, in the case of using INCI names (International Nomenclature Cosmetic Ingredient labeling names).

In the case of blending an emulsifiable crosslinking organopolysiloxane formed by crosslinking by means of a polyether compound in a preparation for external use as a component, the aforementioned co-modified organopolysiloxane can function as a dispersant. For this reason, there is an advantage in that a uniform emulsification system can be formed.

On the other hand, in the case of blending a non-emulsifiable crosslinking organopolysiloxane formed by crosslinking by means of an unsaturated hydrocarbon group such as a diene or an organopolysiloxane in a preparation for external use as a component, an adhesive sensation to the skin can be improved. In addition, there is an advantage in that good compatibility with other oil agents can be exhibited, and the whole oil system can be uniformly and stably blended in the preparation for external use.

The aforementioned silicone elastomer can be blended alone or in combination with two or more types thereof in accordance with the purpose thereof. The silicone elastomer may be blended in an amount preferably ranging from 0.05 to 25% by weight (mass) and more preferably ranging from 0.1 to 15% by weight (mass), with respect to the total amount of the preparation for external use, in accordance with the purpose and blending intention.

The water-soluble polymer may be blended in order to prepare a preparation for external use in the desirable form, and improve sensation during use of the preparation for external use such as feeling on touch with respect to hair or the like, a conditioning effect or the like. Any one of amphoteric, cationic, anionic, and nonionic polymers, and water-swellable clay minerals can be used as long as they are commonly used in a preparation for external use. One type or two or more types of water-soluble polymers can be used. The aforementioned water-soluble polymers have an effect of thickening a hydrous component, and for this reason, they are useful in the case of obtaining a hydrous preparation for external use, and in particular, in the form of a gel, a water-in-oil emulsion preparation for external use, and an oil-in-water emulsion preparation for external use. As examples of natural water-soluble polymers, mention may be made of vegetable-based polymers such as gum Arabic, tragacanth gum, galactan, guar gum, carob gum, karaya gum, carrageenan, pectin, agar, quince seed, algal colloid, starch (rice, corn, potato, or wheat), glycyrrhizinic acid and the like; microorganism-based polymers such as xanthan gum, dextran, succinoglucan, pullulan, and the like; and animal-based polymers such as collagen, casein, albumin, gelatin, and the like. In addition, as examples of semi-synthetic water-soluble polymers, mention may be made of, for example, starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate and the like. As examples of synthetic water-soluble polymers, mention may be made of, for example, vinyl-based polymers such as polyvinyl alcohol, polyvinyl methyl ether-based polymer, polyvinylpyrrolidone, carboxyvinyl polymer (CARBOPOL 940, CARBOPOL 941; manufactured by The Lubrizol Corporation); polyoxyethylene-based polymers such as polyethylene glycol 20,000, polyethylene glycol 6,000, polyethylene glycol 4,000 and the like; copolymer-based polymers such as a copolymer of polyoxyethylene and polyoxypropylene, PEG/PPG methyl ether and the like; acryl-based polymers such as poly(sodium acrylate), poly (ethyl acrylate), polyacrylamide and the like; polyethylene imines; cationic polymers and the like. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride. They may be any one of natural ones and synthesized ones.

As examples of other cationic water-soluble polymers, in particular, as components which are preferably blended in preparations for external use on hair, mention may be made of quaternary nitrogen-modified polysaccharides such as cation-modified cellulose, cation-modified hydroxyethylcellulose, cation-modified guar gum, cation-modified locust bean gum, cation-modified starch and the like; dimethyldiallylammonium chloride derivatives such as a copolymer of dimethyldiallylammonium chloride and acrylamide, poly (dimethylmethylene piperidinium chloride) and the like; vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride and the like; and methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, methacryloylethyl trimethylammonium chloride and methoxy polyethylene glycol methacrylate, and the like.

In addition, in particular, as a component which can be preferably blended in a preparation for external use on hair, an amphoteric water-soluble polymer can be mentioned. More particularly, as examples thereof, mention may be made of amphoterized starches; dimethyldiallylammonium chloride derivatives such as a copolymer of acrylamide, acrylic acid, and dimethyldiallylammonium chloride, and a copolymer of acrylic acid and dimethyldiallylammonium chloride; and methacrylic acid derivatives such as polymethacryloylethyl dimethylbetaine, a copolymer of methacryloyloxyethyl carboxybetaine and alkyl methacrylate, a copolymer of octylacrylamide, hydroxypropyl acrylate and butylaminoethyl methacrylate, and a copolymer of N-methacryloyloxyethyl-N,N-dimethylammonium α-methylcarboxybetaine and alkyl methacrylate.

The blending amount of the water-soluble polymer in the preparation for external use of the present invention can be suitably selected in accordance with the type and purpose of the preparation for external use. The amount preferably may range from 0.01 to 5.0% by weight (mass) and more preferably may range from 0.1 to 3.0% by weight (mass) with respect to the total amount of the preparation for external use in order to particularly obtain a superior sensation during use. If the blending amount of the water-soluble polymer exceeds the aforementioned upper limit, a rough feeling with respect to the hair or skin may remain in some types of the preparations for external use. On the other hand, if the blending amount is below the aforementioned lower limit, advantageous technical effects such as a thickening effect, a conditioning effect and the like may not be sufficiently exhibited.

The surfactant excluding the co-modified organopolysiloxane of the present invention can function as an emulsifier, and for example, the same surfactant as described above can be used.

The usage amount of the other surfactant in the preparation for external use of the present invention is not particularly restricted, and can range from 0.1 to 50% by weight-(mass), and more preferably can range from 1% by weight (mass) to 20% by weight (mass), with respect to the total amount of the preparation for external use.

The oil-soluble gelling agent excluding the co-modified organopolysiloxane of the present invention is a gelling agent of an oil agent. In the case in which the preparation for external use of the present invention is an oil-based preparation for external use having an oil agent as a continuous phase, by thickening/gelling the oil-based component, the desirable formulation and feeling on touch can be obtained. As examples of oil-soluble gelling agents excluding the co-modified organopolysiloxane of the present invention, mention may be made of metallic soaps such as aluminum stearate, magnesium stearate, zinc myristate and the like; amino acid derivatives such as N-lauroyl-L-glutamic acid, α,γ-di-n-butylamine and the like; dextrin fatty acid esters such as dextrin palmitate, dextrin stearate, dextrin 2-ethylhexanoate palmitate and the like; sucrose fatty acid esters such as sucrose, palmitate, sucrose stearate and the like; benzylidene derivatives of sorbitol such as monobenzylidene sorbitol, dibenzylidene sorbitol and the like; and the like. The oil-soluble gelling agents can be used alone or in combination of two or more types thereof, if necessary.

The usage amount of the other oil-soluble gelling agent in the preparation for external use of the present invention is not particularly restricted, and may preferably range from 0.5 to 50 parts by weight (mass) and more preferably may range from 1 to 30 parts by weight (mass), with respect to 100 parts by weight (mass) of the oil agent(s).

When the other oil-soluble gelling agent is used in the preparation for external use in which the aforementioned co-modified organopolysiloxane, powder(s) and oil agent(s) are blended, there are advantages in view of qualities in that an oily sensation (oily and sticky feeling on touch) can be further totally controlled, and a skin-maintaining property can be further improved.

The organo-modified clay mineral can be used as a gelling agent for the oil agent(s) in the same manner as described in the aforementioned oil-soluble gelling agent. As examples of organo-modified clay minerals, mention may be made of, for example, dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate and the like. As examples of commercially available products thereof, mention may be made of Benton 27 (benzyldimethylstearylammonium chloride-treated hectorite, manufactured by Nationalred Co.), Benton 38 (distearyldimethylammonium chloride-treated hectorite, manufactured by Nationalred Co.) and the like.

The silicone gum is a linear diorganopolysiloxane having an ultra-high degree of polymerization, and is also referred to as a silicone raw rubber or an organopolysiloxane gum. The silicone raw rubber possesses a high degree of polymerization, and for this reason, it has a measurable degree of plasticity. In view of this, the silicone gum is different from the aforementioned oil silicones. The aforementioned silicone gum can be blended in the preparation for external use according to the present invention as it is, or as a liquid gum dispersion (an oil dispersion of the silicone gum) in which the silicone gum is dispersed in an oil silicone.

As examples of the aforementioned silicone raw rubber, mention may be made of substituted or non-substituted organopolysiloxanes having a dialkylsiloxy unit (D unit) such as dimethylpolysiloxane, methylphenylpolysiloxane, aminopolysiloxane, methylfluoroalkyl polysiloxane and the like, or those having a micro-crosslinking structure thereof and the like. As representative examples thereof, there are those represented by the following general formula:

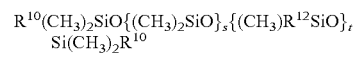

wherein $R^{12}$ is a group selected from a vinyl group, a phenyl group, an alkyl group having 6 to 20 carbon atoms, an aminoalkyl group having 3 to 15 carbon atoms, a perfluoroalkyl group having 3 to 15 carbon atoms, and a quaternary ammonium salt group-containing alkyl group having 3 to 15 carbon atoms; the terminal group $R^{10}$ is a group selected from an alkyl group having 1 to 8 carbon atoms, a phenyl group, a vinyl group, an aminoalkyl group having 3 to 15 carbon atoms, a hydroxyl group and an alkoxy group having 1 to 8 carbon atoms; $s=2,000$ to $6,000$; $t=0$ to $1,000$; and $s+t=2,000$ to $6,000$. Among these, a dimethylpolysiloxane raw rubber having a degree of polymerization ranging from 3,000 to 20,000 is preferred. In addition, an amino-modified methylpolysiloxane raw rubber having a 3-aminopropyl group, an N-(2-aminoethyl)-3-aminopropyl group or the like on the side chain or the terminal of the molecule is preferred. In addition, in the present invention, the silicone gum can be used alone or in combination with two or more types thereof, as necessary.

The silicone gum has an ultra-high degree of polymerization. For this reason, the silicone gum can exhibit a superior retention property on hair or skin, and can form a protective film with a superior aeration property. For this reason, the silicone gum is a component which can particularly provide glossiness and luster on hair and can impart a texture with tension on the entire hair during use and after use.

The blending amount of the silicone gum may range from 0.05 to 30% by weight (mass) and may preferably range from 1 to 15% by weight (mass), with respect to the total amount of the preparation for external use. When the silicone gum is used as an emulsion composition prepared via a step of preliminarily emulsifying (including emulsion polymerization), the silicone gum can be easily blended, and can stably be blended in the preparation for external use of the present invention. If the blending amount of the silicone gum is below the aforementioned lower limit, an effect of imparting specific feeling on touch or glossiness with respect to hair may be insufficient.

The organo-modified silicone is a silicone compound in which a functional group is introduced into a part of the polysiloxane chain, is an organo-modified silicone other than the aforementioned co-modified organopolysiloxane, and can be blended in the preparation for external use. As examples thereof, mention may be made of an amino-modified silicone, an aminopolyether-modified silicone, an epoxy-modified silicone, a carboxy-modified silicone, an amino acid-modified silicone, acryl-modified silicone, a phenol-modified silicone, an amidoalkyl-modified silicone, an aminoglycol-modified silicone, an alkoxy-modified silicone, and a silicone modified with a higher alkyl group having 8 to 30 carbon atoms.

The organo-modified silicone may have an alkylene chain, an aminoalkylene chain, or a polyether chain, in addition to a polysiloxane bond as a main chain, and includes so-called block copolymer. In addition, the aforementioned organo-modified group(s) may be present at the side chain(s) or at one or both of the terminal(s) of the polysiloxane chain.

The organo-modified silicone can be blended alone or in combination with two or more types thereof in accordance with the purpose thereof. A function as the aforementioned silicone-based surfactant, a function as a powder treatment agent, an effect of improving smoothness and glossiness with respect to hair, and in particular, a function of improving feeling on touch after rinsing the hair, and the like can be exhibited. In the preparation for external use of the present invention, the blending amount of the organo-modified silicone is not particularly restricted, and may preferably range from 0.05 to 25% by weight (mass) and more preferably may range from 0.1 to 15% by weight (mass), with respect to the total amount of the preparation for external use. If the amount is below the aforementioned lower limit, the desirable function of the organo-modified silicone may not be sufficiently exhibited. On the other hand, if the amount exceeds the aforementioned upper limit, balance of feeling on touch, functions, and the like of the preparation for external use may be impaired.

A UV-ray protective component is a component for blocking or diffusing UV rays. Among UV-ray protective components, there are inorganic UV-ray protective components and organic UV-ray protective components. If the preparations for external use of the present invention are sunscreen cosmetics, at least one type of inorganic or organic UV-ray protective component, and in particular, an organic UV-ray protective component is preferably contained.

The inorganic UV-ray protective components may be components in which the aforementioned inorganic powder pigments, metal powder pigments and the like are blended as UV-ray dispersants. As examples thereof, mention may be made of metal oxides such as titanium oxide, zinc oxide, cerium oxide, titanium suboxide, iron-doped titanium oxides and the like; metal hydroxides such as iron hydroxides and the like; metal flakes such as platy iron oxide, aluminum flake and the like; and ceramics such as silicon carbide and the like. Among these, at least one type of a material selected from fine particulate metal oxides and fine particulate metal hydroxides with an average particle size ranging from 1 to 100 nm in the form of granules, plates, needles, or fibers is, in particular, preferred. The aforementioned powders are preferably subjected to conventional surface treatments such as fluorine compound treatments, among which a perfluoroalkyl phosphate treatment, a perfluoroalkylsilane treatment, a perfluoropolyether treatment, a fluorosilicone treatment, and a fluorinated silicone resin treatment are preferred; silicone treatments, among which a methylhydrogenpolysiloxane treatment, a dimethylpolysiloxane treatment, and a vapor-phase tetramethyltetrahydrogencyclotetrasiloxane treatment are preferred; silicone resin treatments, among which a trimethylsiloxysilicic acid treatment is preferred; pendant treatments which are methods of adding alkyl chains after the vapor-phase silicone treatment; silane coupling agent treatments; titanium coupling agent treatments; silane treatments among which an alkylsilane treatment and an alkylsilazane treatment are preferred; oil agent treatments; N-acylated lysine treatments; polyacrylic acid treatments; metallic soap treatments in which a stearic acid salt or a myristic acid salt is preferably used; acrylic resin treatments; metal oxide treatments and the like. Multiple treatments described above are preferably carried out. For example, the surface of the fine particulate titanium oxide can be coated with a metal oxide such as silicon oxide, alumina or the like, and then, a surface treatment with an alkylsilane can be carried out. The total amount of the material used for the surface treatment may preferably range from 0.1 to 50% by weight (mass) based on the amount of the powder.

The organic UV-ray protective components are generally lipophilic. More particularly, as examples of the aforementioned organic UV-ray protective components, mention may be made of benzoic acid-based UV-ray absorbers such as paraminobenzoic acid (hereinafter, referred to as PABA), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester, 2-[4-(diethylamino)-2-hydroxybenzoyl]benzoic acid hexyl ester (trade name: Uvinul A Plus) and the like; anthranilic acid-based UV-ray absorbers such as homomethyl N-acetylanthranilate and the like; salicylic acid-based UV-ray absorbers such as amyl salicylate, menthyl salicylate, homomethyl salicylate, octyl salicylate, phenyl salicylate, benzyl salicylate, p-isopropanolphenyl salicylate and the like; cinnamic acid-based UV-ray absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxy cinnamate, ethyl α-cyano-β-phenylcinnamate, 2-ethylhexyl α-cyano-β-phenylcinnamate, glyceryl mono-2-ethylhexanoyl-diparamethoxycinnamate, 3-methyl-4-[methylbis(trimethylsiloxy)silyl]butyl 3,4,5-trimethoxycinnamate, dimethicodiethyl benzal malonate (trade name: Parsol SLX (INCI name=polysilicone-15) and the like; benzophenone-based UV-ray absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone 5-sulfonate, 4-phenylbenzophenone, 2-ethylhexyl-4'-phenylbenzophenone 2-carboxylate, hydroxy-4-n-octoxybenzophenone, 4-hydroxy-3-carboxybenzophenone and the like; 3-(4'-methylbenzylidene)-d,l-camphor; 3-benzylidene-d,l-camphor; urocanic acid; ethyl urocanate; 2-phenyl-5-methylbenzoxazole; benzotriazole-based UV-ray absorbers such as 2,2'-hydroxy-5-methylphenyl benzotriazole, 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butylbenzoylmethane, 5-(3,3-dimethyl-2-norbonylidene)-3-pentan-2-one, 2,2'-methylenebis(6-(2H-benzotriazol-2-yl)-4-(1,1,3,3-tetramethylbutyl)phenol) (trade name: trademark TINOSORB M) and the like; triazine-based UV-ray absorbers such as 2,4,6-tris[4-(2-ethylhexyloxycarbonyl)anilino]1,3,5-triazine (INCI: octyltriazone), 2,4-bis{[4-(2-ethyl-hexyloxy)-2-hydroxy]phenyl}-6-(4-methoxyphenyl)-1,3,5-triazine (INCI: bis-ethylhexyloxyphenol methoxyphenyl triazine, trade name: trademark TINOSORB S) and the like; 2-ethylhexyl 2-cyano-3,3-diphenylprop-2-enoate (INCI: octocrylene) and the like.

Furthermore, hydrophobic polymer powders containing the aforementioned organic UV-ray protective components inside thereof can also be used. The polymer powder may be hollow or not, may have an average primary particle size thereof ranging from 0.1 to 50 μm and may have a particle size distribution thereof of either broad or sharp. As examples of the polymers, mention may be made of acrylic resins, methacrylic resins, styrene resins, polyurethane resins, polyethylene, polypropylene, polyethylene terephthalate, silicone resins, nylons, acrylamide resins, and silylated polypeptide resins. Polymer powders containing the organic UV-ray protective components in an amount ranging from 0.1 to 30% by weight (mass) with respect to the amount of the powder are preferred. Polymer powders containing 4-tert-butyl-4'-methoxydibenzoylmethane, which is a UV-A absorber, are particularly preferred.

The UV-ray protective components which can be preferably used in the preparations for external use of the present invention may be at least one type of compound selected from the group consisting of fine particulate titanium oxide, fine particulate zinc oxide, 2-ethylhexyl paramethoxycinnamate, 4-tert-butyl-4'-methoxydibenzoylmethane, benzotriazole-based UV-ray absorbers and triazine-based UV-ray absorbers. The aforementioned UV-ray protective components are commonly used and easily available, and exhibit superior effects of preventing ultraviolet rays. For these reasons, the aforementioned UV-ray protective components are preferably used. In particular, inorganic UV-ray protective components and organic UV-ray protective components are preferably used in combination. In addition, UV-A protective components and UV-B protective components are further preferably used in combination.

In the preparation for external use of the present invention, by use of the aforementioned co-modified organopolysiloxane together with the UV-ray protective component(s), the whole feeling on touch and storage stability of the preparation for external use can be improved, and at the same time, the UV-ray protective component(s) can stably dispersed in the preparation for external use. For this reason, superior UV-ray protective functions can be provided to the preparation for external use.

In the preparation for external use of the present invention, the aforementioned UV-ray protective component(s) may be blended in a total amount preferably ranging from 0.1 to 40.0% by weight (mass), and more preferably ranging from 0.5 to 15.0% by weight (mass), with respect to the total amount of the preparation for external use can be blended.

In addition, in the preparation for external use of the present invention, at least one material selected from the group consisting of acryl silicone dendrimer copolymers, polyamide-modified silicones, alkyl-modified silicone waxes, and alkyl-modified silicone resin waxes.

Acryl silicone dendrimer copolymers are vinyl-based polymer having a carbosiloxane dendrimer structure at the side chain. As examples thereof, mention may be, in particular, preferably made of vinyl-based polymers described in Japanese Patent No. 4,009,382 (Japanese Unexamined Patent Application, First Publication No. 2000-063225). As examples of commercially available products, mention may be made of FA 4001 CM Silicone Acrylate, and FA 4002 ID Silicone Acrylate, manufactured by Dow Corning Toray Co., Ltd., and the like. An acryl silicone dendrimer copolymer having a long chain alkyl group having 8 to 30 carbon atoms and preferably having 14 to 22 carbon atoms at the side chain or the like may be used. In the case of blending the aforementioned acryl silicone dendrimer copolymer alone, a superior property of forming a film can be exhibited. For this reason, by blending the dendrimer copolymer in the preparation for external use according to the present invention, a strong coating film can be formed on the applied part, and durability of a sebum resistance property, a rub resistance property and the like can be considerably improved.

By using the aforementioned co-modified organopolysiloxane together with an acryl silicone dendrimer copolymer, there are advantages in that a surface protective property such as a sebum resistance property can be improved due to strong water repellency provided by the carbosiloxane dendrimer structure; and at the same time, irregularities such as pores and wrinkles of the skin to be applied can be effectively made inconspicuous. In addition, the aforementioned co-modified organopolysiloxane can exhibit a superior dispersion property with respect to the other oil agent(s) and powder(s), and can provide miscibility of an acryl silicone dendrimer copolymer with the other oil agent(s). For this reason, there is an advantage in that makeup running or gathering on the skin can be controlled for a long time. In addition, when powders are treated in accordance with a conventional method by using the aforementioned co-modified organopolysiloxane together with the acryl silicone dendrimer copolymer, a raw material for a preparation for external use (powder composition for use in a preparation for external use) exhibiting superior blending stability can be prepared.

The blending amount of the acryl silicone dendrimer copolymer can appropriately be selected in accordance with the purpose and blending intention. The amount may preferably range from 1 to 99% by weight (mass), and more preferably may range from 30 to 70% by weight (mass), with respect to the total amount of the preparation for external use.

As examples of polyamide-modified silicones, mention may be made of, for example, siloxane-based polyamides described in U.S. Pat. No. 5,981,680 (Japanese Unexamined Patent Application, First Publication No. 2000-038450) and Published Japanese Translation No. 2001-512164 of the PCT International Application, and as examples of commercially available products, mention may be made of 2-8178 Gellant, 2-8179 Gellant and the like (manufactured by Dow Corning Corporation, in the USA). The aforementioned polyamide-modified silicones are useful as an oil-based raw material, and in particular, a thickening/gelling agent of a silicone oil in the same manner as described in the aforementioned oil-soluble gelling agent.

In the case of using the polyamide-modified silicone together with the aforementioned co-modified organopolysiloxane, compatibility with the oil agent such as a silicone oil or the like can be further improved. For this reason, the preparation for external use according to the present invention can exhibit a good spreading property, a good styling property, a superior stable sensation and a superior adhesive property in the case of applying to the skin, hair or the like. In addition, there are advantages in view of qualities in that a glossy transparent sensation and superior gloss can be provided, the viscosity or hardness (flexibility) of the whole preparation for external use containing oil-based raw material(s) can be appropriately adjusted, and an oily sensation (oily and sticky feeling on touch) can be totally controlled. In addition, by use of the aforementioned co-modified organopolysiloxane, dispersion stability of perfume(s), powder(s) and the like can be improved. For this reason, for example, there is a characteristic in that a uniform and fine cosmetic sensation can be maintained for a long time.

The usage amount of the polyamide-modified silicone may appropriately be selected in accordance with the purpose and blending intention. In the case of using as a gelling agent of an oil-based raw material, the amount may preferably range from 0.5 to 80 parts by weight (mass) and more preferably may range from 1 to 50 parts by weight (mass), with respect to 100 parts by weight (mass) of the oil agent.

The alkyl-modified silicone waxes are components useful as a part of a base material of an oil-based solid preparation for external use. In the preparation for external use of the present invention, an alkyl-modified silicone in the form of a wax at room temperature can be used without particular restrictions. As examples thereof, mention may be made of a methyl(long chain alkyl)polysiloxane having both molecular terminals capped with trimethylsiloxy groups, a copolymer of a dimethylpolysiloxane having both molecular terminals capped with trimethylsiloxy groups and a methyl (long chain alkyl)siloxane, a dimethylpolysiloxane modified with long chain alkyls at both terminals, and the like. As examples of commercially available products thereof, mention may be made of, AMS-C30 Cosmetic Wax, 2503 Cosmetic Wax and the like (manufactured by Dow Corning Corporation, in the USA).

The aforementioned co-modified organopolysiloxane can exhibit a superior dispersion property of an alkyl-modified silicone wax, and for this reason, a preparation for external use exhibiting superior storage stability for a long time can be obtained. In addition, a superior forming property of the preparation for external use can also be exhibited. In particular, in a system containing powder(s), there is an advantage in that separation of the alkyl-modified silicone wax hardly occurs, and an oil-based preparation for external use which can exhibit superior form-retaining strength and can be smoothly and uniformly spread during application can be provided.

In the preparation for external use of the present invention, and in particular, the cosmetic, the alkyl-modified silicone wax preferably has a melting point of 60° C. or higher in view of a makeup durability effect and stability at increased temperatures. The blending amount thereof can be appropriately selected in accordance with the purpose and blending intention, and usually ranges from 1 to 50% by weight (mass) with respect to the total amount of the preparation for external use. In order to improve formability and cosmetic durability of the oil-based preparation for external use, the alkyl-modified silicone wax may be blended in an amount more preferably ranging from 5 to 40% by weight (mass). In addition, the alkyl-modified silicone wax can exhibit rich compatibility with silicone oil(s) having a long-chain alkyl group such as the aforementioned alkyl-modified silicone or the like, and crosslinking organopolysiloxanes. For this reason, the aforementioned optional components are preferably used.

The alkyl-modified silicone resin wax is a component for imparting sebum durability, a moisture-retaining property, and a fine texture feeling on touch to the preparation for external use. For example, a silsesquioxane resin wax described in Published Japanese Translation No. 2007-532754 of the PCT International Application may be mentioned. As commercially available products thereof, SW-8005 C30 RESIN WAX (manufactured by Dow Corning Corporation in the USA) and the like may be mentioned.

The aforementioned co-modified organopolysiloxane can uniformly disperse the alkyl-modified silicone resin wax in the preparation for external use, in the same manner as described in the alkyl-modified silicone wax. In addition, an oil phase containing the aforementioned alkyl-modified silicone resin wax can be stably emulsified optionally together with the other surfactant. A conditioning effect with respect to skin or hair can be improved and a fine texture and moisturized feeling on touch can be imparted.

In the preparation for external use of the present invention, the blending amount of the alkyl-modified silicone resin wax may appropriately be selected in accordance with the purpose and blending intention. The amount can usually range from 0.5 to 50% by weight (mass) with respect to the total amount of the preparation for external use. In order to realize sebum durability and a fine texture feeling on touch of the preparation for external use, the blending amount may preferably range from 1 to 30% by weight (mass).

In the preparations for external use, and in particular, the cosmetics of the present invention, other components usually used in preparations for external use can be blended within a range which does not impair the effects of the present invention, such as alcohols, organic resins, moisture-retaining agents, thickening agents, preservatives, anti-microbial agents, perfumes, salts, antioxidants, pH adjusting agents, chelating agents, algefacients, anti-inflammatory agents, physiologically active components, components for beautifying the skin (such as whitening agents, cell activators, agents for ameliorating skin roughness, blood circulation accelerators, astringents, antiseborrheic agents and the like), vitamins, amino acids, nucleic acids, hormones, clathrate compounds and the like. They are not particularly restricted thereto.

As the alcohols, one type or two or more types of polyhydric alcohols and/or lower monovalent alcohols can be used. As examples of lower alcohols, mention may be made of ethanol, isopropanol, n-propanol, t-butanol, s-butanol and the like. As examples of polyhydric alcohols, mention may be made of divalent alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexyleneglycol, octylene glycol and the like; trivalent alcohols such as glycerol, trimethylolpropane, 1,2,6-hexanetriol and the like; polyhydric alcohols having tetra- or more valences such as pentaerythritol, xylitol and the like; sugar alcohols such as sorbitol, mannitol, maltitol, maltotriose, sucrose, erytritol, glucose, fructose, starch-decomposed products, maltose, xylitose, starch-decomposed reduction alcohols and the like. In addition to the aforementioned polyhydric alcohols having a low molecular weight, mention may be made of polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol and the like. Among these, 1,3-propanediol, 1,3-butylene glycol, sorbitol, dipropylene glycol, glycerol, and polyethylene glycol are, in particular, preferred. The blending amount thereof may preferably range from 0.1 to 50% by weight (mass) with respect to the total amount of the preparation for external use. The alcohol(s) can be blended in order to improve storage stability of the preparation for external use, in an amount ranging from about 5 to 30% by weight (mass), with respect to the total amount of the preparation for external use. This is one of the preferable modes for carrying out the present invention.

As examples of organic resins, mention may be made of polyvinyl alcohol, polyvinyl pyrrolidone, poly(alkyl acrylate) copolymers, and the like. The organic resin possesses a superior property of forming a film. For this reason, by blending the organic resin in the preparation for external use of the present invention, a strong coating film can be formed at the applied part, and durability such as sebum resistance and rub resistance or the like can be improved.

As examples of humectants, mention may be made of, for example, hyaluronic acid, chondroitin sulfate, pyrrolidone carboxylic acid salts, polyoxyethylene methylglucoside, polyoxypropylene methylglucoside, and the like. Needless to say, the aforementioned polyhydric alcohols exhibit a function of retaining moisture on the skin or hair.

As examples of the preservatives, mention may be made of, for example, alkyl paraoxybenzoates, benzoic acid, sodium benzoate, sorbic acid, potassium sorbate, phenoxyethanol and the like. As examples of the antimicrobial agents, mention may be made of benzoic acid, salicylic acid, carbolic acid, sorbic acid, alkyl paraoxybenzoates, parachloromethacresol, hexachlorophene, benzalkonium chloride, chlorhexidine chloride, trichlorocarbanilide, trichlosan, photosensitizers, isothiazolinone compounds such as 2-methyl-4-isothiazolin-3-one, 5-chloro-2-methyl-4-isothiazolin-3-one and the like, amine oxides such as dimethyl laurylamine oxide, dihydroxyethyl laurylamine oxide and the like, and the like.

In addition, as examples of anti-microbial agents, mention may be made of apolactoferrin; phenol-based compounds such as resorcinol; anti-microbial or fungicidal basic proteins or peptides such as iturin-based peptides, surfactin-based peptides, protamine or salts thereof (protamine sulfate and the like) and the like; polylysines such as $\epsilon$-polylysine or salts thereof, and the like; anti-microbial metal compounds which can produce a silver ion, a copper ion or the like; antimicrobial enzymes such as protease, lipase, oxydoreductase, carbohydrase, transferase, phytase and the like; and the like.

As examples of perfume, mention may be made of perfume extracted from flowers, seeds, leaves, and roots of various plants; perfume extracted from seaweeds; perfume extracted from various parts or secretion glands of animals such as musk and sperm oil; or artificially synthesized perfume such as menthol, musk, acetate, and vanilla. The conventional perfume can be selected and blended in an appropriate amount in accordance with the formulations of the preparations for external use in order to provide a certain aroma or scent to the preparations for external use, or in order to mask unpleasant odor.

As examples of antioxidants, mention may be made of, for example, tocopherol, butylhydroxyanisole, dibutylhydroxytoluene, phytic acid and the like.

As examples of pH adjustors, mention may be made of, for example, lactic acid, citric acid, glycolic acid, succinic acid, tartaric acid, dl-malic acid, potassium carbonate, sodium hydrogencarbonate, ammonium hydrogencarbonate and the like.

As examples of chelating agents, mention may be made of, for example, alanine, sodium salt of edetic acid, sodium polyphosphate, sodium metaphosphate, phosphoric acid and the like.

As examples of algefacients, mention may be made of l-menthol, camphor and the like.

As examples of physiologically active components, mention may be made of, for example, vitamins, amino acids, nucleic acids, hormones, components extracted from natural Vegetables, seaweed extracted components, herbal medicine components, whitening agents such as placenta extracts, arbutin, glutathione, saxifrageous extracts and the like; cell activators such as royal jelly, and the like; agents for ameliorating skin roughness; blood circulation accelerators such as nonylic acid vanillylamide, benzyl nicotinate, beta-butoxyethyl nicotinate, capsaicin, gingerone, cantharide tincture, ichthammol, caffeine, tannic acid, alpha-borneol, tocopherol nicotinate, inositol hexanicotinate, cyclandelate, cinnarizine, tolazoline, acetylcholine, verapamil, cepharanthine, gamma-orizanol and the like; astringents such as zinc oxide, tannic acid and the like; antiseborrheic agents such as sulfur, thianthol and the like; anti-inflammatory agents such as $\epsilon$-aminocaproic acid, glycyrrhizinic acid, $\beta$-glycyrrhetinic acid, lysozyme chloride, guaiazulene, hydrocortisone, allantoin, tranexamic acid, azulene and the like; and the like.

As examples of vitamins, mention may be made of vitamin As such as vitamin A oil, retinol, retinol acetate, retinol palmitate and the like; vitamin Bs such as vitamin B2s such as riboflavin, riboflavin butyrate, flavin adenine dinucleotide and the like; vitamin B6s such as pyridoxine hydrochloride, pyridoxine dioctanoate, pyridoxine tripalmitate and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester and the like; vitamin Ds such as ergocalciferol, cholecalciferol and the like; vitamin Es such as alpha-tocopherol, beta-tocopherol, gamma-tocopherol, dl-alpha-tocopherol acetate, dl-alpha-tocopherol nicotinate, dl-alpha-tocopherol succinate and the like; vitamin H; vitamin P; nicotinic acids such as nicotinic acid, benzyl nicotinate and the like; pantothenic acids such as calcium pantothenate, D-pantothenyl alcohol, pantothenyl ethyl ether, acetyl pantothenyl ethyl ether and the like; and the like.

As examples of amino acids, mention may be made of glycine, valine, leucine, isoleucine, serine, threonine, phenylalanine, arginine, lysine, aspartic acid, glutamate, cystine, cysteine, methionine, tryptophan and the like.

As examples of nucleic acids, mention may be made of deoxyribonucleic acid and the like.

As examples of hormones, mention may be made of estradiol, ethenyl estradiol and the like.

In the preparations for external use of the present invention, natural vegetable extract components, seaweed extract components and herbal medicine components can be blended in accordance with the purposes thereof. As the aforementioned components, in particular, one or more types of components having effects such as whitening effects, anti-ageing effects, effects of ameliorating ageing, effects of beautifying skin, anti-microbial effects, preservative effects and the like can be preferably blended.

As detailed examples thereof, mention may be made of, for example, *Angelica keiskei* extract, avocado extract, *Hydrangea serrata* extract, *Althaea officinalis* extract, *Arnica montana* extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* bark extract, *Coptis rhizome* extract, *Hordeum vulgare* seed extract, *Hypericum perforatum* extract, *Lamium album* extract, *Nasturtium officinale* extract, orange extract, dried sea water solution, seaweed extract, hydrolyzed elastin, hydrolyzed wheat powders, hydrolyzed silk, *Chamomilla recutita* extract, carrot extract, *Artemisia capillaris* flower extract, *Glycyrrhiza glabra* extract, *Hibiscus sabdariffa* extract, *Pyracantha fortuneana* extract, kiwi extract, *Cinchona succirubra* extract, cucumber extract, guanosine, *Gardenia florida* extract, *Sasa veitchii* extract, *Sophora angustifolia* extract, walnut extract, grapefruit extract, *Clematis vitalba* leaf extract, chlorella extract, *Morus alba* extract, *Gentiana lutea* extract, black tea extract, yeast extract, burdock extract, fermented rice bran extract, rice germ oil, *Symphytum officinale* leaf extract, collagen, *Vaccinum vitis idaea* extract, *Asiasarum sieboldi* extract, *Bupleurum falcatum* extract, umbilical extract, Salvia extract, *Crocus sativus* flower extract, *sasa* bamboo grass extract, *Crataegus cuneata* fruit extract, *Zanthoxylum piperitum* extract, *Corthellus shiitake* extract, *Rehmannia chinensis* root extract, *Lithospermum erythrorhizone* root extract, *Perilla ocymoides* extract, *Tilia cordata* extract, *Spiraea ulmaria* extract, *Paeonia albiflora* extract, *Acorns calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean seed extract, *Zizyphus jujuba* fruit extract, thyme extract, *Camellia sinensis* leaf extract, *Eugenia caryophyllus* flower extract, *Imperata cylindrica* extract, *Citrus unshiu* peel extract, *Angelica acutiloba* root extract, *Calendula officinalis* extract, *Prunus persica* kernel extract, *Citrus aurantium* peel extract, *Houttuynia cordata* extract, tomato extract, natto extract, carrot extract, garlic extract, *Rosa canina* fruit extract, hibiscus extract, *Ophiopogon japonicus* root extract, *Nelumbo nucifera* extract, parsley extract, honey, *Hamamelis virginiana* extract, *Parietaria officinalis* extract, *Isodon trichocarpus* extract, bisabolol, *Eriobotrya japonica* extract, *Tussilago farfara* flower extract, *Petasites japonicus* extract, *Poria cocos* extract, *Ruscus aculeatus* root extract, grape extract, propolis, *Luffa cylindrica* fruit extract, safflower flower extract, peppermint extract, *Tillia miquellana* extract, *Paeonia suffruticosa* root extract, *Humulus lupulus* extract, *Pinus sylvestris* cone extract, horse chestnut extract, *Lysichiton camtschatcense* extract, *Sapindus mukurossi* peel extract, *Melissa officinalis* leaf extract, peach extract, *Centaurea cyanus* flower extract, *Eucalyptus globulus* leaf extract, *Saxifraga sarementosa* extract, *Citrus junos* extract, *Coix lacryma-jobi* seed extract, *Artemisia princeps* extract, lavender extract, apple extract, lettuce extract, lemon extract, *Astragalus sinicus* extract, rose extract, rosemary extract, *Roman chamomile* extract, and royal jelly extract. The aforementioned extracts may be water-soluble or oil-soluble.

In the preparations for external use of the present invention, depending on the purposes thereof, solvents such as light isoparaffins, ethers, LPG, N-methylpyrrolidone, next-generation chlorofluorocarbons, and the like, can be blended in addition to water such as purified water, mineral water and the like.

The preparations for external use of the present invention can be in the form of liquids, milky lotions, creams, solids, pastes, gels, powders, lamellas, mousses, sprays, sheets, and the like. As examples of the preparations for external use of the present invention, mention may be made of, for example, UV-ray protective products such as sunscreen agents and the like; skin care products such as cosmetic lotions, cosmetic milks, creams, cleansing products, products for use in massaging, cleansing agents and the like; makeup products such as foundations, makeup bases, cheek colors, eye shadows, mascaras, eyeliners, lipsticks and the like; products for use on hair such as shampoos, rinses, treatments and the like; antiperspirant products; deodorant products and the like. As examples of the preparations for external use on skin, mention may be made of ointments, hair growth agents, hair tonics, analgistics, fungicides, anti-inflammatory agents, algefacients, and skin ageing preventors.

EXAMPLES

Hereinafter, the present invention is described in detail with reference to examples. It should be understood that the present invention is not restricted to the examples. An Me$_3$SiO group (or a Me$_3$Si group) is indicated as "M", an Me$_2$SiO group is indicated as "D", an Me$_2$HSiO group is indicated as "M$^H$", an MeHSiO group is indicated as "D$^H$", and units in which a methyl group (Me) in M and D is modified by any substituent are respectively indicated as "M$^R$" and "D$^R$".

In addition, the xylitol monoallyl ether and the xylitol residue described in the following Examples and Reference Example 2 are the same raw material and functional group as described in the specification of the present application. More particularly, the xylitol monoallyl ether is a raw material comprising xylitol monoallyl ethers represented by the following structural formula: CH$_2$=CH—CH$_2$—OCH$_2$[CH(OH)]$_3$CH$_2$OH and represented by the following structural formula: CH$_2$=CH—CH$_2$—OCH{CH(OH)CH$_2$OH}$_2$ in a weight (mass) ratio of 9:1. In the co-modified silicone of the present invention, the xylitol residue of C$_3$H$_6$—OCH$_2$[CH(OH)]$_3$CH$_2$OH or —C$_3$H$_6$—OCH{CH(OH)CH$_2$OH}$_2$ corresponding thereto is introduced in the same weight (mass) ratio as described above.

Example 1

Synthesis of Silicone Compound No. 1

159.5 g of a methylhydrogenpolysiloxane represented by the following average compositional formula: MD$_{72}$D$^H_{12}$M, 81.9 g of a vinyltristrimethylsiloxysilane represented by the following average compositional formula: CH$_2$=CH—Si(OSi(CH$_3$)$_3$)$_3$, 19.8 g of xylitol monoallyl ether, and 75 g of isopropyl alcohol (IPA) were placed in a reactor, and the mixture was heated to 80° C. under a nitrogen stream while it was stirred. 30 mg of a platinum catalyst was added thereto, and the mixture was reacted for 2.5 hours at 80° C. It was confirmed that the Si—H bond had disappeared by means of an IR spectrum, and the reaction had proceeded. The reaction mixture was heated under reduced pressure to remove low-boiling components by distillation. Thereby, a novel xylitol-co-modified silicone having a siloxane dendron structure represented by the following compositional formula: $MD_{72}D^{R*1}{}_{3}D^{R*2}{}_{9}M$, wherein
$R^{*1}$=xylitol residue; and
$R^{*2}$=—$C_2H_4Si(OSiMe_3)_3$
was obtained. The yield was 222.0 g (85%). The product had a kinetic viscosity of 298,900 mm²/sec at 25° C., and a refraction index of 1.416, and was in the form of a pale yellow opaque uniform viscous liquid.

Example 2

Synthesis of Silicone Compound No. 2

97.3 g of 1,3-dihydrodisiloxane was placed in a reactor and heated to 75° C. A mixture of 46.8 g of a vinyltristrimethylsiloxysilane represented by the following compositional formula: $CH_2$=CH—$Si(OSi(CH_3)_3)_3$ and 4 mg of a platinum catalyst was added thereto dropwise over 3 hours. After aging was carried out for one hour, it was confirmed that the vinyltristrimethylsiloxysilane had disappeared by means of gas chromatography. The remaining 1,3-dihydrodisiloxane was removed under reduced pressure. Subsequently, 33.8 g of xylitol monoallyl ether and 30 g of isopropyl alcohol (IPA) were added thereto, and the mixture was heated to 80° C. while it was stirred. 8 mg of a platinum catalyst was added thereto, and the mixture was reacted for 2.5 hours at 80° C. It was confirmed that the Si—H bond had disappeared by means of an IR spectrum, and the reaction had proceeded. The reaction mixture was heated under reduced pressure to remove low-boiling components by distillation. Thereby, a novel xylitol-co-modified silicone having a siloxane dendron structure represented by the following compositional formula: $M^{R*1}M^{R*2}$, wherein
$R^{*1}$=xylitol residue; and
$R^{*2}$=—$C_2H_4Si(OSiMe_3)_3$
was obtained. The yield was 86.0 g (86%). The product had a kinetic viscosity of 117,300 mm²/sec at 25° C., and a refraction index of 1.442, and was in the form of a pale yellow translucent uniform viscous liquid.

Example 3

Synthesis of Silicone Compound No. 3

168.1 g of a methylhydrogenpolysiloxane represented by the following compositional formula: $MD_{72}D^{H}{}_{12}M$, 28.8 g of a vinyltristrimethylsiloxysilane represented by the following compositional formula: $CH_2$=CH—$Si(OSi(CH_3)_3)_3$, 18.9 g of xylitol monoallyl ether, 42.9 g of 1-hexadecene, and 75 g of isopropyl alcohol (IPA) were placed in a reactor, and the mixture was heated to 80° C. under a nitrogen stream while it was stirred. 30 mg of a platinum catalyst was added thereto, and the mixture was reacted for 2.5 hours at 80° C. It was confirmed that the Si—H bond had disappeared by means of an IR spectrum, and the reaction had proceeded. The reaction mixture was heated under reduced pressure to remove low-boiling components by distillation. Thereby, a novel xylitol-co-modified silicone having a siloxane dendron structure represented by the following compositional formula: the following compositional formula: $MD_{72}D^{R*1}{}_{3}D^{R*2}{}_{3}D^{R*3}{}_{6}M$ wherein
$R^{*1}$=xylitol residue;
$R^{*2}$=—$C_2H_4Si(OSiMe_3)_3$; and
$R^{*3}$=—$C_{16}H_{33}$
was obtained. The yield was 225.1 g (87%). The product had a kinetic viscosity of 141,000 mm²/sec at 25° C., and a refraction index of 1.424, and was in the form of a pale yellow opaque uniform viscous liquid.

Example 4

Synthesis of Silicone Compound No. 4

226.5 g of a methylhydrogenpolysiloxane represented by the following compositional formula: $MD_{45}D^{H}{}_{2}M$, 20.2 g of a vinyltristrimethylsiloxysilane represented by the following compositional formula: $CH_2$=CH—$Si(OSi(CH_3)_3)_3$, 16.3 g of xylitol monoallyl ether, and 78 g of isopropyl alcohol (IPA) were placed in a reactor, and the mixture was heated to 80° C. under a nitrogen stream while it was stirred. 31 mg of a platinum catalyst was added thereto, and the mixture was reacted for 3 hours at 80° C. It was confirmed that the Si—H bond had disappeared by means of an IR spectrum, and the reaction had proceeded. The reaction mixture was heated under reduced pressure to remove low-boiling components by distillation. Thereby, a novel xylitol-co-modified silicone having a siloxane dendron structure represented by the following compositional formula: $MD_{45}D^{R*1}{}_{1}D^{R*2}{}_{1}M$ wherein
$R^{*1}$=xylitol residue; and
$R^{*2}$=—$C_2H_4Si(OSiMe_3)_3$
was obtained. The yield was 234.9 g (89%). The product had a kinetic viscosity of 4,600 mm²/sec at 25° C., and a refraction index of 1.410, and was in the form of a pale yellow translucent uniform liquid.

Example 5

Synthesis of Silicone Compound No. 5

116.6 g of a methylhydrogenpolysiloxane represented by the following compositional formula: $MD_{72}D^{H}{}_{12}M$, 12.1 g of a vinyltristrimethylsiloxysilane represented by the following compositional formula: $CH_2$=CH—$Si(OSi(CH_3)_3)_3$, 13.5 g of xylitol monoallyl ether, 29.7 g of 1-hexadecene, 38.1 g of a one-terminal vinyl-modified dimethylpolysiloxane represented by the following average structural formula: $CH_2$=$CHSi(CH_3)_2[OSi(CH_3)_2]_{25}OSi(CH_3)_3$ and 63 g of isopropyl alcohol (IPA) were placed in a reactor, and the mixture was heated to 80° C. under a nitrogen stream while it was stirred. 24 mg of a platinum catalyst was added thereto, and the mixture was reacted for 2.5 hours at 80° C. It was confirmed that the Si—H bond had disappeared by means of an IR spectrum, and the reaction had proceeded. The reaction mixture was heated under reduced pressure to remove low-boiling components by distillation. Thereby, a novel xylitol-co-modified silicone having a siloxane dendron structure represented by the following compositional formula: $MD_{72}D^{R*1}{}_{3}D^{R*2}{}_{2}D^{R*3}{}_{6}D^{R*4}{}_{1}M$ wherein
$R^{*1}$=xylitol residue;
$R^{*2}$=—$C_2H_4Si(OSiMe_3)_3$;
$R^{*3}$=—$C_{16}H_{33}$; and
$R^{*4}$=—$C_2H_4Si(CH_3)_2[OSi(CH_3)_2]_{25}OSi(CH_3)_3$
was obtained. The yield was 181.2 g (86%). The product had a kinetic viscosity of 198,000 mm²/sec at 25° C., and a refraction index of 1.422, and was in the form of a pale yellow opaque uniform liquid.

Reference Example 1

Synthesis of Tetraglycerol-Modified Silicone 1

168.9 g of a methylhydrogenpolysiloxane represented by the following compositional formula: $MD_{72}D^H{}_3M$, 41.1 g of tetraglycerol monoallyl ether, 63.0 g of IPA were placed in a reactor, and the mixture was heated to 80° C. under a nitrogen stream while it was stirred. 24 mg of a platinum catalyst was added thereto, and the mixture was reacted for 3 hours at 80° C. It was confirmed that the Si—H bond had disappeared by means of an IR spectrum, and the reaction had proceeded. The reaction mixture was heated under reduced pressure to remove low-boiling components by distillation. Thereby, Tetraglycerol-Modified Silicone 1 represented by the following compositional formula: $MD_{72}D^{R*5}{}_3M$ wherein
$R^{*5}$=—$C_3H_6O$—X (X represents a tetraglycerol moiety) was obtained. The yield was 180.6 g (86%). The product had a kinetic viscosity of 750,000 mm²/sec or more at 25° C., and a refraction index of 1.429, and was in the form of a milky opaque uniform viscous liquid.

Reference Example 2

Synthesis of Xylitol-Modified Silicone 172.6 g of a methylhydrogenpolysiloxane represented by the following compositional formula: $MD_{72}D^H{}_{12}M$, 19.4 g of xylitol monoallyl ether, 66.1 g of 1-hexadecene, and 75.2 g of isopropyl alcohol (IPA) were placed in a reactor, and the mixture was heated to 80° C. under a nitrogen stream while it was stirred. 30 mg of a platinum catalyst was added thereto, and the mixture was reacted for 2.5 hours at 80° C. It was confirmed that the Si—H bond had disappeared by means of an IR spectrum, and the reaction had proceeded. The reaction mixture was heated under reduced pressure to remove low-boiling components by distillation. Thereby, Xylitol-Modified Silicone represented by the following compositional formula: $MD_{72}D^{R*1}{}_3D^{R*2}{}_9M$ wherein
$R^{*1}$=xylitol residue; and
$R^{*2}$=—$C_{16}H_{33}$
was obtained. The yield was 216.8 g (84%). The product had a kinetic viscosity of 750,000 mm²/sec or more at 25° C., and a refraction index of 1.429, and was in the form of a topaz opaque uniform viscous liquid.

Reference Example 3

Synthesis of Tetraglycerol-Modified Silicone 2

69.5 g of a methylhydrogenpolysiloxane represented by the following compositional formula: $MD_{72}D^H{}_{12}M$, 15.5 g of tetraglycerol monoallyl ether, 6.0 g of 1-octene, 119.4 g of a one-terminal vinyl-modified dimethylpolysiloxane represented by the following average structural formula: $CH_2$=$CHSi(CH_3)_2[OSi(CH_3)_2]_{25}OSi(CH_3)_3$, 63.0 g of IPA were placed in a reactor, and the mixture was heated to 80° C. under a nitrogen stream while it was stirred. 24 mg of a platinum catalyst was added thereto, and the mixture was reacted for 3 hours at 80° C. It was confirmed that the Si—H bond had disappeared by means of an IR spectrum, and the reaction had proceeded. The reaction mixture was heated under reduced pressure to remove low-boiling components by distillation. Thereby, Tetraglycerol-Modified Silicone 2 represented by the following compositional formula: $MD_{72}D^{R*6}{}_3D^{R*4}{}_5D^{R*7}{}_4M$ wherein
$R^{*6}$=—$C_3H_6O$—X (X represents a tetraglycerol moiety);
$R^{*4}$=—$C_2H_4Si(CH_3)_2[OSi(CH_3)_2]_{25}OSi(CH_3)_3$; and
$R^{*7}$=—$C_8H_{17}$
was obtained. The yield was 183.1 g (87%). The product had a kinetic viscosity of 237,000 mm²/sec or more at 25° C., and a refraction index of 1.416, and was in the form of a milky opaque uniform viscous liquid.

Examples 6 to 20

Water-in-oil emulsion compositions having the compositions shown in Table 1 were prepared using "Silicone Compound No. 1" obtained in Example 1, "Silicone Compound No. 2" obtained in Example 2, "Silicone Compound No. 3" obtained in Example 3, "Silicone Compound No. 4" obtained in Example 4, and "Silicone Compound No. 5" obtained in Example 5, in accordance with the method described below. Miscibility with an oil agent, emulsion stability, and a functional property (feeling on touch and sensation during use) thereof were evaluated on the basis of the following evaluation criteria. The results are also shown in Table 1 and Table 2. In the tables, the numerical values are indicated by "parts by weight (mass)".

Comparative Examples 1 to 9

Water-in-oil emulsion compositions having the compositions shown in Table 2 were prepared using "Tetraglycerol-Modified Silicone 1" obtained in Reference Example 1, "Xylitol-Modified Silicone" obtained in Reference Example 2, and "Tetraglycerol-Modified Silicone 2" obtained in Reference Example 3, in the same manner as described in Examples 6 to 20. In addition, miscibility with an oil agent, emulsion stability, and a functional property (feeling on touch and sensation during use) thereof were evaluated in the same manner as described in Examples 6 to 20. The results are also shown in Table 2. In the table, the numerical values are indicated by "parts by weight (mass)".

Preparation Method of Water-in-Oil Emulsion Composition

1. An oil agent shown in Table 1 and Table 2 and each of the modified silicones as a surfactant (emulsifying agent) were placed in a vessel with a volume of 150 ml.
2. The modified silicone was uniformly dispersed or dissolved in the oil agent by heating and stirring the mixture (Oil Phase A).
3. Sodium chloride and ion-exchanged water were placed in another vessel and mixed by means of a spatula to dissolve the mixture. In addition, 1,3-butylene glycol was mixed therein and dissolved (Aqueous Phase B).
4. Saw teeth of a homodisper were immersed in the aforementioned Oil Phase A, and the vessel was fixed. Subsequently, while the aforementioned Oil Phase A was stirred at 1,000 rpm, the aforementioned Aqueous Phase B was poured into the aforementioned Oil Phase A at an approximately specified rate over about 40 seconds.
5. The mixture was further stirred for one minute after the revolutions per minute of the homodisper was increased to 3,000 rpm. Thereby, a water-in-oil emulsion composition was obtained.

Evaluation of Miscibility Between an Oil Agent and a Modified-Silicone
O: The mixture was translucently dissolved or uniformly dispersed.
Δ: Dispersion was coarse, and particles of the modified silicone could be observed.
X: The modified silicone was not dispersed, and was separated by sedimentation.

Evaluation of Emulsion Stability
Each of the water-in-oil emulsion compositions was allowed to stand for one month at 40° C. The change in the emulsion condition before and after the aforementioned standing was evaluated in accordance with the evaluation criteria described below.
OO: Viscosity change≤±5%, and the outer appearance did not change and was uniform.
O: ±5%≤viscosity change≤±10%, and the outer appearance was uniform.
Δ: ±10%≤viscosity change≤±20%, or the surface of the emulsion was slightly non-uniform.
X: ±20%≤viscosity change, or aqueous droplets and separation of the aqueous phase were observed.

Evaluation of Functional Property (Feeling on Touch or Sensation During Use)
0.10 g of each of the water-in-oil emulsion compositions was applied to a forearm part by lightly gliding the emulsion. The action of lightly trailing the fingers on the skin (applied part) was repeated several times so that the emulsion was uniformly spread. During application, the feeling on touch and sensation during use were evaluated both on the initial stage of the application and on the late stage of the application in accordance with the evaluation criteria described below. Relative comparison was carried out using the emulsions with the same oil agent each other.

Initial Stage of the Application
OO: A moisturizing aqueous sensation was exhibited, and the emulsion was smoothly spread without stickiness. A smooth slipping sensation was exhibited.
O: A moisturizing aqueous sensation was exhibited, and the emulsion was smoothly spread without stickiness. A viscous slipping sensation was exhibited.
Δ: A moisturizing feeling on touch was exhibited, and the emulsion was normally spread without stickiness, but a slipping sensation was slightly impaired.

Late Stage of the Application (after the Emulsion was Spread on the Skin and the White Part of the Emulsion Disappeared)
O: A lightly and superior smooth sensation was maintained, and an oily sensation was reduced.
Δ: A slightly heavy and thickened sensation was maintained, and a slightly oily sensation was exhibited.
X: A poor and viscous resistance was exhibited, and an oily sensation was strong.

TABLE 1

| Raw material Name | Example 6 | 7 | 8 | 9 | 10 | 11 | 12 | 13 | 14 | 15 | 16 | 17 |
|---|---|---|---|---|---|---|---|---|---|---|---|---|
| Silicone Compound No. 1 | 2 | 2 | 2 | — | — | — | — | — | — | — | — | — |
| Silicone Compound No. 2 | — | — | — | 2 | 2 | 2 | — | — | — | — | — | — |
| Silicone Compound No. 3 | — | — | — | — | — | — | 2 | 2 | 2 | — | — | — |
| Silicone Compound No. 4 | — | — | — | — | — | — | — | — | — | 2 | 2 | 2 |
| Silicone oil | 23 | 11.5 | 11.5 | 23 | 11.5 | 11.5 | 23 | 11.5 | 11.5 | 23 | 11.5 | 11.5 |
| Light liquid isoparaffin | — | 11.5 | — | — | 11.5 | — | — | 11.5 | — | — | 11.5 | — |
| Cetyl 2-ethylhexanoate | — | — | 11.5 | — | — | 11.5 | — | — | 11.5 | — | — | 11.5 |
| Sodium chloride | 0.5 | 0.5 | 0.5 | 0.5 | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 | 6 | 6 | 6 | 6 |
| Miscibility | o | o | o | o | o | o | o | o | o | o | o | o |
| Emulsion stability | oo | oo | o | o | o | oo | o | oo | oo | oo | o | o |
| Feeling on touch and sensation during use (initial stage of the application) | oo | oo | o | oo | oo | o | oo | oo | o | oo | oo | o |
| Feeling on touch and sensation during use (late stage of the application) | o | o | Δ | o | o | Δ | o | o | Δ | o | o | Δ |

TABLE 2

| Raw material Name | Example 18 | 19 | 20 | Comparative Example 1 | 2 | 3 | 4 | 5 | 6 | 7 | 8 | 9 |
|---|---|---|---|---|---|---|---|---|---|---|---|---|
| Silicone Compound No. 5 | 2 | 2 | 2 | — | — | — | — | — | — | — | — | — |
| Tetraglycerol-Modified Silicone 1 | — | — | — | 2 | 2 | 2 | — | — | — | — | — | — |
| Xylitol-Modified Silicone | — | — | — | — | — | — | 2 | 2 | 2 | — | — | — |
| Tetraglycerol-Modified Silicone 2 | — | — | — | — | — | — | — | — | — | 2 | 2 | 2 |
| Silicone oil | 23 | 11.5 | 11.5 | 23 | 11.5 | 11.5 | 23 | 11.5 | 11.5 | 23 | 11.5 | 11.5 |
| Light liquid isoparaffin | — | 11.5 | — | — | 11.5 | — | — | 11.5 | — | — | 11.5 | — |
| Cetyl 2-ethylhexanoate | — | — | 11.5 | — | — | 11.5 | — | — | 11.5 | — | — | 11.5 |
| Sodium chloride | 0.5 | 0.5 | 0.5 | 0.5 | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 | 6 | 6 | 6 | 6 |
| Miscibility | o | o | o | o | o | o | X | X | X | o | o | o |
| Emulsion stability | oo | oo | o | o | Δ | X | Δ | Δ | Δ | o | o | Δ |

TABLE 2-continued

| | Example | | | Comparative Example | | | | | | | | |
|---|---|---|---|---|---|---|---|---|---|---|---|---|
| Raw material Name | 18 | 19 | 20 | 1 | 2 | 3 | 4 | 5 | 6 | 7 | 8 | 9 |
| Feeling on touch and sensation during use (initial stage of the application) | ○○ | ○○ | ○ | Δ | Δ | Δ | ○ | Δ | Δ | Δ | Δ | Δ |
| Feeling on touch and sensation during use (late stage of the application) | ○ | ○ | Δ | Δ | Δ | X | Δ | Δ | X | Δ | Δ | X |

It can be seen that the water-in-oil emulsion compositions using "Silicone Compound No. 1" to "Silicone Compound No. 5" according to the present invention exhibit good miscibility with respect to any oil agent of a silicone oil, a hydrocarbon oil and a fatty acid ester, and in particular, exhibit superior emulsion stability. In addition, in the evaluation of functional properties of the aforementioned emulsion compositions, it can be seen that in particular, on the initial stage of the application, a moisturizing aqueous sensation is exhibited, the compositions are smoothly spread well without stickiness, and a distinctive smoothing sensation can be obtained. On the other hand, in the comparative examples using hydrophilic silicones such as the tetraglycerol-modified silicone without a siloxane dendron structure in the molecule, or the like, poor miscibility with an oil agent and poor emulsion stability are exhibited, as compared with those of the examples of the present invention. In addition, those of the comparative examples exhibit poor results also in view of sensation during use, as compared with those of the examples of the present invention.

Examples 21 to 25

Liquid foundations having compositions shown in Table 3 were prepared by using "Silicone Compound No. 1" to "Silicone Compound No. 5" obtained in Example 1 to Example 5. In accordance with the evaluation criteria described below, a spreading property, beauty of makeup, an adhesive sensation, natural skin impression without a discomfort sensation, and stability thereof were evaluated. The results are also shown in Table 3. In the table, the numerical values are indicated by parts by weight (mass).

Comparative Examples 10 to 12

Liquid foundations having compositions shown in Table 4 were prepared by using "Tetraglycerol-Modified Silicone 1" obtained in Reference Example 1, "Xylitol-Modified Silicone" obtained in Reference Example 2, and "Tetraglycerol-Modified Silicone 2" obtained in Reference Example 3. In the same manner as described in Examples 21 to 25, a spreading property, beauty of makeup, an adhesive sensation, natural skin impression without a discomfort sensation, and stability thereof were evaluated. The results are also shown in Table 4. In the table, the numerical values are indicated by parts by weight (mass).

Evaluation Procedures
1. The obtained liquid foundation, in an amount of 0.15 g, was uniformly applied on a clean skin (forearm part) of which downy hair had been shaved beforehand, in the form of a circle having a diameter of about 5 cm by using a puff. "A spreading property" on the skin was evaluated.
2. 10 minutes (initial stage), 4 hours and 9 hours after the application, "beauty of makeup", "an adhesive sensation", and "natural skin impression without a discomfort sensation" were functionally evaluated by visual judgment and tactile sensation.
3. The obtained liquid foundation was allowed to stand for 2 months at 40° C., and subsequently, stability of the outer appearance and properties was evaluated.

Evaluation Criteria

Each of the evaluation categories was evaluated in accordance with the evaluation criteria described below.

"Spreading Property"

OO: The foundation smoothly spread well.

O: The foundation normally spread.

Δ: An increased power for spreading the foundation was needed, as compared with the usual case.

"Beauty of Makeup"

OO: The skin was closely covered and superior beauty of makeup was exhibited.

O: The skin was closely covered, but runnels due to fine wrinkles were slightly observed.

X: A uniform sensation on the surface of the applied skin was slightly impaired, and a coarse texture was observed.

"Adhesive Sensation"

OO: An adhesive sensation was clearly exhibited.

O: An adhesive sensation was exhibited, but the level of the adhesive sensation was hardly detectable.

X: No adhesive sensation was exhibited.

"Natural Skin Impression without a Discomfort Sensation"

OO: A natural skin impression without a discomfort sensation was exhibited.

O: A natural skin impression with a slightly discomfort sensation was exhibited.

Δ: A slightly unnatural skin impression was exhibited.

"Stability"

O: Uniform outer appearance and properties were maintained without separation or sedimentation of powders.

Δ: Sedimentation of powders was slightly observed, but the powders could be easily and uniformly re-dispersed when shaken.

X: Powders were sedimented, and uniform re-dispersion could not be carried out even if shaken.

TABLE 3

| Raw material | Example 21 | Example 22 | Example 23 | Example 24 | Example 25 |
|---|---|---|---|---|---|
| (1) Cyclopentasiloxane | | | 9.56 | | |
| (2) Octylsilane-treated titanium oxide | | | 2.5 | | |
| (3) Octylsilane-treated yellow iron oxide | | | 3.5 | | |
| (4) Octylsilane-treated black iron oxide | | | 1.37 | | |
| (5) Octylsilane-treated red iron oxide | | | 2.18 | | |
| (6) Isododecane/acrylate polytrimethylsiloxy copolymer | | | 5 | | |
| (7) Isododecane | | | 4 | | |
| (8) Methyltrimethicone | | | 4 | | |
| (9) Caprylylmethicone | | | 4 | | |
| (10) Liquid paraffin | | | 2.35 | | |
| (11) Silicone Compound No. 1 | 7.27 | — | — | — | — |
| (12) Silicone Compound No. 2 | — | 7.27 | — | — | — |
| (13) Silicone Compound No. 3 | — | — | 7.27 | — | — |
| (14) Silicone Compound No. 4 | — | — | — | 7.27 | — |
| (15) Silicone Compound No. 5 | — | — | — | — | 7.27 |
| (19) Purified water | | | remainder | | |
| (20) Sodium chloride | | | 0.97 | | |
| (21) Polysorbate 20 | | | 0.2 | | |
| Spreading property | ⊚ | ⊚ | ○ | ○ | ⊚ |
| Beauty of makeup (initial stage/4 hr/9 hr) | ⊚/○/○ | ⊚/○/○ | ⊚/○/○ | ⊚/○/○ | ⊚/○/○ |
| Adhesive sensation (initial stage/4 hr/9 hr) | ⊚/○/○ | ⊚/○/○ | ⊚/○/○ | ⊚/○/○ | ⊚/○/○ |
| Natural skin impression without a discomfort sensation (initial stage/4 hr/9 hr) | ○/○/○ | ○/○/○ | ○/○/○ | ○/○/○ | ○/○/○ |
| Stability | ○ | ○ | ○ | ○ | ○ |

TABLE 4

| Raw material | Comparative Example 10 | Comparative Example 11 | Comparative Example 12 |
|---|---|---|---|
| (1) Cyclopentasiloxane | | 9.56 | |
| (2) Octylsilane-treated titanium oxide | | 2.5 | |
| (3) Octylsilane-treated yellow iron oxide | | 3.5 | |
| (4) Octylsilane-treated black iron oxide | | 1.37 | |
| (5) Octylsilane-treated red iron oxide | | 2.18 | |
| (6) Isododecane/acrylate polytrimethylsiloxy copolymer | | 5 | |
| (7) Isododecane | | 4 | |
| (8) Methyltrimethicone | | 4 | |
| (9) Caprylylmethicone | | 4 | |
| (10) Liquid paraffin | | 2.35 | |
| (16) Tetraglycerol-Modified Silicone 1 | 7.27 | — | — |
| (17) Xylitol-Modified Silicone | — | 7.27 | — |
| (18) Tetraglycerol-Modified Silicone 2 | — | — | 7.27 |
| (19) Purified water | | remainder | |
| (20) Sodium chloride | | 0.97 | |
| (21) Polysorbate 20 | | 0.2 | |
| Spreading property | Δ | ○ | ○ |
| Beauty of makeup (initial stage/4 hr/9 hr) | ○/○/Δ | ○/○/Δ | ○/Δ/X |
| Adhesive sensation (initial stage/4 hr/9 hr) | ⊚/○/Δ | ○/Δ/Δ | ○/X/X |
| Natural skin impression without a discomfort sensation (initial stage/4 hr/9 hr) | ○/Δ/Δ | ○/Δ/Δ | ○/Δ/X |
| Stability | ○ | ○ | ○ |

Preparation Method

A: Component (1) and components (6) to (18) were mixed at room temperature, and subsequently, the mixture was stirred by means of a homomixer to dissolve them.

B: Components (19) to (21) were mixed and the mixture was completely dissolved.

C: Subsequently, the aforementioned solution B was added to the aforementioned solution A while the solution A was stirred by means of a homomixer.

D: Components (2) to (5) were added thereto, and mixed and dispersed by means of a homomixer, followed by deaerating. A container was charged therewith, and thereby, a liquid foundation was obtained.

The liquid foundations using "Silicone Compound No. 1" to "Silicone Compound No. 5" according to the present invention (Examples 21 to 25) exhibited superiority in view of a spreading property and beauty of makeup, as compared with Comparative Examples 10 to 12. In addition, the liquid foundations of the present invention obtained identical or better evaluation results in view of all of the evaluations of sensation during use, as compared with Comparative Examples 10 to 12. In particular, in the case of comparing the foundations of the present invention with the liquid foundation containing Tetraglycerol-Modified Silicone 1 or 2 which does not contain a siloxane dendron structure in a molecule, the liquid foundations of the present invention exhibited remarkably superior performance in the functional evaluation in the case of using the foundation for a long time of 9 hours or more.

Hereinafter, compositions of cosmetics of the present invention including emulsion compositions, powder treatment agent compositions and the like are particularly described below as examples of the present invention. It should be understood that the present invention is not restricted thereto. In the compositions, in the case of describing "Co-Modified Silicone 1 (or 2)", this indicates the co-modified silicone according to the present invention obtained in Example 1 (or Example 2). In the compositions, "parts" indicates parts by weight (mass).

Example 26

Sunscreen Cosmetic

Preparation of a Slurry of Titanium Oxide

Before a sunscreen cosmetic in accordance with this composition example of the present invention was prepared, a slurry of titanium oxide as a cosmetic raw material was prepared using "Silicone Compound No. 4" obtained in Example 4. More particular, 20 g of titanium oxide fine particles (trade name: MTY-100SAS (manufactured by Tayca Corporation)), 5 g of Silicone Compound No. 4, and 25 g of decamethylpentacyclosiloxane were mixed, and 200 g of zirconia beads (diameter of 0.8 mm) were added thereto. The mixture was mixed for one hour by means of a paint shaker, and thereby, a dispersion in the form of a slurry was prepared.

Preparation of a Slurry of Zinc Oxide

Before the sunscreen cosmetic in accordance with the present Example 26 was prepared, a slurry of zinc oxide as a cosmetic raw material was prepared using "Silicone Compound No. 4" obtained in Example 4. More particular, 30 g of zinc oxide fine particles (trade name: MZY-505S (manufactured by Tayca Corporation)), 2.5 g of Silicone Compound No. 4, and 17.5 g of decamethylcyclopentasiloxane were mixed, and 200 g of zirconia beads (diameter of 0.8 mm) were added thereto. The mixture was mixed for one hour by means of a paint shaker, and thereby, a dispersion in the form of a slurry was prepared.

Next, a sunscreen cosmetic was prepared in accordance with the composition described below using the aforementioned slurry of titanium oxide and the aforementioned slurry of zinc oxide.

|  | (Components) | (part(s)) |
|---|---|---|
| 1. | Polyether-modified silicone (Note 1) | 1.5 |
| 2. | Dimethylsilicone (6 mm²/s) | 5 |
| 3. | Decamethylcyclopentasiloxane | 3.5 |
| 4. | Octyl paramethoxycinnamate | 2 |
| 5. | Trimethylsiloxysilicic acid | 2 |
| 6. | Isodecyl isononanoate | 4 |
| 7. | Slurry of titanium oxide (Note 2) | 2.0 |
| 8. | Slurry of zinc oxide (Note 3) | 10.0 |
| 9. | 1,3-butylene glycol | 8 |
| 10. | Sodium chloride | 0.5 |
| 11. | Purified water | remainder |
| 12. | Preservatives | q.s. |

(Note 1):
SS-2910 manufactured by Dow Corning Toray Co., Ltd., was used.
(Note 2):
The sample prepared in accordance with the aforementioned method was used.
(Note 3):
The sample prepared in accordance with the aforementioned method was used.

Preparation Method

An aqueous phase obtained by mixing and stirring components 9 to 12 was added to an oil phase obtained by mixing and stirring components 1 to 6, and the mixture was stirred to emulsify. Slurries of components 7 and 8 were added to the emulsion, and mixed and stirred. Thereby, a sunscreen cosmetic was obtained.

The slurry of the inorganic powders obtained by using Silicone Compound No. 4 of the present invention exhibited a superior dispersing property of the inorganic powders. The sunscreen cosmetic obtained by blending the aforementioned slurries of the inorganic powders exhibited uniformity as a whole, and superior storage stability, and in particular, even in the case of storing for a long time, separation of the inorganic powder components was not observed. In addition, good compatibility between the oil agent and the inorganic powders was exhibited during use, the cosmetic was moisturizingly spread on the skin, the cosmetic was not easily affected by perspiration, and a comfortable sensation during use could be maintained for a long time.

Example 27

Makeup Base

|  | (Components) | (part(s)) |
|---|---|---|
| 1. | Decamethylcyclopentasiloxane | 9.0 |
| 2. | Polyether-modified silicone (Note 1) | 3.0 |
| 3. | Phenyltrimethicone | 12.49 |
| 4. | Silicone Compound No. 1 | 1.5 |
| 5. | Natural vitamin E | 0.2 |
| 6. | Squalane | 3.0 |
| 7. | Trioctanoin | 2 |
| 8. | Silicone-treated titanium oxide | 1 |
| 9. | Silicone-treated iron oxide | 0.01 |
| 10. | Perfume | 0.04 |
| 11. | Magnesium sulfate | 0.2 |
| 12. | Purified water | remainder |
| 13. | Glycerol | 3.0 |
| 14. | 1,3-butylene glycol | 5.0 |
| 15. | Polyvinyl alcohol | 0.2 |
| 16. | Preservatives | q.s. |

(Note 1):
SS-2910 manufactured by Dow Corning Toray Co., Ltd., was used.

Preparation Method

Components 1 to 7 were uniformly mixed. Components 8 and 9 were dispersed in the aforementioned mixture. Subsequently, a mixture of components 10 to 16 was added thereto to emulsify. After deaeration, a specified container was charged with the obtained emulsion. Thereby, a makeup base was obtained.

In the makeup base obtained by using Silicone Compound No. 1 of the present invention, the oil agent and the like were stably emulsified, a uniform outer appearance was maintained, and superior stability over time was exhibited in the case of storage. In addition, in the case of using the composition as a makeup base, good compatibility to the skin was exhibited, and an effect of improving durability of makeup used after the makeup base was exhibited.

Example 28

Milky Lotion

|     | (Components)                    | (part(s))  |
| --- | ------------------------------- | ---------- |
| 1.  | Dimethicone (2 mm$^2$/s)        | 3          |
| 2.  | Isododecane                     | 7.0        |
| 3.  | Silicone Compound No. 3         | 1.5        |
| 4.  | Polyether-modified silicone (Note 1) | 3.0   |
| 5.  | Liquid paraffin                 | 5          |
| 6.  | Caprylmethicone                 | 5          |
| 7.  | Natural vitamin E               | 0.2        |
| 8.  | Squalane                        | 3.0        |
| 9.  | Octylsilane-treated titanium oxide | 0.8     |
| 10. | Perfume                         | q.s.       |
| 11. | Magnesium sulfate               | 0.2        |
| 12. | Purified water                  | remainder  |
| 13. | Glycerol                        | 3.0        |
| 14. | 1,3-butylene glycol             | 5.0        |
| 15. | Polyvinyl alcohol               | 0.1        |
| 16. | Preservatives                   | q.s.       |

(Note 1):
DC5200 Formulation aid manufactured by Dow Corning Corporation was used.

Preparation Method
Components 1 to 8 were uniformly mixed. Component 9 was dispersed in the aforementioned mixture. Subsequently, a mixture of components 10 to 16 was added thereto to emulsify.

The emulsion obtained by Using Silicone Compound No. 3 of the present invention possessed a stable emulsion state, and a superior moisturizing sensation was exhibited without stickiness to the skin.

Example 29

Cream

|     | (Components)                                    | (part(s))  |
| --- | ----------------------------------------------- | ---------- |
| 1.  | Phenyltrimethicone                              | 3.0        |
| 2.  | Isopropyl myristate                             | 3.5        |
| 3.  | Microcrystalline wax                            | 0.5        |
| 4.  | Decamethylcyclopentasiloxane                    | 6.0        |
| 5.  | 1,3-butylene glycol                             | 3.0        |
| 6.  | Silicone Compound No. 4                         | 0.8        |
| 7.  | Polyether-modified silicone (Note 1)            | 0.7        |
| 8.  | Polyethylene glycol 150                         | 1.0        |
| 9.  | Ethanol                                         | 6.0        |
| 10. | Dimethicone/vinyldimethicone crosspolymer/silica (Note 2) | 6.0 |
| 11. | Silicone-treated titanium mica                  | 0.5        |
| 12. | Phenoxyethanol                                  | 0.4        |
| 13. | Glycylglycine                                   | 5.0        |
| 14. | Perfume                                         | q.s.       |
| 15. | Purified water                                  | remainder  |

(Note 1):
DC5225 Formulation Aid, manufactured by Dow Corning Corporation was used.
(Note 2):
9701 Cosmetic Powder, manufactured by Dow Corning Toray Co., Ltd., was used.

Preparation Method
Components 1 to 11 were mixed, and a mixture of components 12 to 15 was added thereto to emulsify. Thereby, a cream was obtained.

The cream obtained by using Silicone Compound No. 4 of the present invention exhibited good storage stability and possessed a stable emulsion state. In addition, a good spreading property on the skin during use was exhibited, and in particular, even in the case of using the cream for a long time, superior uniformity of the cosmetic film was exhibited, and a superior moisture-retaining property was exhibited without stickiness.

Example 30

W/O Emulsion Foundation

|     | (Components)                                                                | (part(s))  |
| --- | --------------------------------------------------------------------------- | ---------- |
| 1.  | Dimethylpolysiloxane (2 mm$^2$/s)                                           | 10.0       |
| 2.  | Isostearic acid                                                             | 3.0        |
| 3.  | Cyclopentasiloxane/(acrylate/polytrimethylsiloxy methacrylate) copolymer (Note 1) | 1.0  |
| 4.  | Polyether-modified silicone (Note 2)                                        | 2.0        |
| 5.  | Silicone Compound No. 5                                                     | 1.0        |
| 6.  | Propylene glycol                                                            | 2.5        |
| 7.  | Ethanol                                                                     | 6.0        |
| 8.  | Paraben                                                                     | 0.1        |
| 9.  | Dimethicone/vinyldimethicone crosspolymer                                   | 6.0        |
| 10. | Octylsilane-treated titanium mica                                           | 0.8        |
| 11. | Silicone-treated titanium oxide                                             | 2.5        |
| 12. | Silicone-treated mica                                                       | 2.5        |
| 13. | Silicone-treated talc                                                       | 1.5        |
| 14. | Silicone-treated iron oxide                                                 | 4.5        |
| 15. | Antioxidant                                                                 | q.s.       |
| 16. | Glycylglycine                                                               | 3.0        |
| 17. | Perfume                                                                     | 0.05       |
| 18. | Purified water                                                              | remainder  |

(Note 1):
FA4001CM Silicone Acrylate, manufactured by Dow Corning Toray Co., Ltd., was used.
(Note 2):
BY11-030, manufactured by Dow Corning Toray Co., Ltd., was used.

Preparation Method
Components 1 to 14 were mixed, and a mixture of components 15 to 18 was added thereto to emulsify.

The W/O emulsion foundation obtained by using Silicone Compound No. 5 of the present invention exhibited superior uniformity and superior storage stability of the emulsion, and in particular, even at an increased temperature, superior stability over time was exhibited without separating the aqueous phase or the inorganic powder component. In addition, the foundation was comfortably spread on the skin and smooth applicability was exhibited. In addition, after making up, fine texture finishing was provided.

Example 31

UV Protector

|     | (Components)                              | (part(s))  |
| --- | ----------------------------------------- | ---------- |
| 1.  | Phenyltrimethicone                        | 2.0        |
| 2.  | Decamethylcyclopentasiloxane              | 25.0       |
| 3.  | Isodecyl isononanoate                     | 4.0        |
| 4.  | Glycerol                                  | 4.0        |
| 5.  | 1,3-butylene glycol                       | 0.5        |
| 6.  | Polysilicone 13                           | 0.5        |
| 7.  | Silicone Compound No. 1                   | 1.0        |
| 8.  | Ethanol                                   | 9.0        |
| 9.  | Dimethicone/vinyldimethicone crosspolymer | 10.0       |
| 10. | Silicone-treated titanium mica            | 1.5        |
| 11. | Titanium oxide fine particle              | 5.0        |
| 12. | Octyl paramethoxycinnamate                | 5.0        |
| 13. | Glycylglycine                             | 1.0        |
| 14. | Perfume                                   | 0.1        |
| 15. | Purified water                            | remainder  |

Preparation Method

Components 1 to 12 were mixed, and a mixture of components 13 to 15 was added thereto to emulsify.

The UV protector obtained by using Silicone Compound No. 1 of the present invention possessed a uniform emulsion condition, and the inorganic and organic UV-ray protective components were stably blended therein. Superior stability over time and a superior effect of controlling UV rays were exhibited. In addition, a good sensation during use without stickiness was exhibited.

Example 32

Moisture-Retaining Cream

| | (Components) | (part(s)) |
|---|---|---|
| | Oil phase: | |
| 1. | Decamethylcyclopentasiloxane | 10 |
| 2. | Dimethylpolysiloxane | 5 |
| 3. | Tocopherol acetate | 0.1 |
| 4. | Silicone Compound No. 1 | 0.5 |
| 5. | Polymeric polyether-modified silicone (Note 1) | 2 |
| | Aqueous phase: | |
| 6. | Ion-exchanged water | remainder |
| 7. | Glycerol | 5 |
| 8. | 1,3-butylene glycol | 5 |
| 9. | Maltitol | 2 |
| 10. | Polyoxyethylene glucoside (10 EO) | 2 |
| 11. | Salicylic acid | 0.3 |
| 12. | Trimethylglycine | 0.5 |
| 13. | Erythritol | 0.5 |
| 14. | Sodium hyaluronate | 0.01 |
| 15. | Sodium chloride | 1 |
| 16. | Lactic acid | 0.1 |
| 17. | Sodium lactate | 0.05 |
| 18. | EDTA | 0.1 |
| 19. | Phenoxyethanol | 0.1 |
| 20. | Perfume | q.s. |

(Note 1):
BY22-008M manufactured by Dow Corning Toray Co., Ltd., was used.

Preparation Method

The components of the aforementioned oil phase and the components of the aforementioned aqueous phase were independently uniformly dissolved and dispersed. The aqueous phase was added to the oil phase by means of a homogenizer, and thereby, a uniform cream was obtained.

In the moisture-retaining cream obtained by using Silicone Compound No. 1 of the present invention, the oil agent and the like were uniformly emulsified, a superior storage stability was exhibited, and a stable emulsion condition was maintained without occurring change of the outer appearance or change of viscosity caused by temperature change over time. In addition, during use, a superior spreading property, and good compatibility with the skin were exhibited, and an emollient sensation providing a moisture-retaining sensation and moisturizing feeling of the skin was provided without stickiness.

The invention claimed is:

1. A co-modified organopolysiloxane represented by general formula (1):

wherein
each $R^1$ independently represents a monovalent organic group, with the proviso that $R^2$, $L^1$ and Q are excluded therefrom;
each $R^2$ independently represents a substituted or non-substituted, and linear or branched monovalent hydrocarbon group having 9 to 30 carbon atoms, or a linear organosiloxane group represented by general formula (2-1):

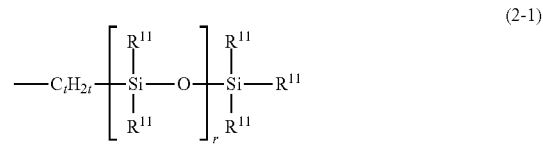

wherein each $R^{11}$ independently is a substituted or non-substituted monovalent hydrocarbon group having 1 to 30 carbon atoms, a hydroxyl group or a hydrogen atom, and at least one $R^{11}$ is said monovalent hydrocarbon group; t is a number ranging from 2 to 10; and r is a number ranging from 1 to 500,
or represented by general formula (2-2):

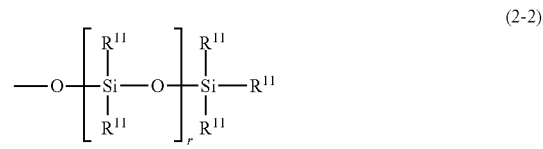

wherein $R^{11}$ and r are the same as defined above;
each $L^1$ independently represents a silylalkyl group having a siloxane dendron structure, in the case of i=1, represented by general formula (3):

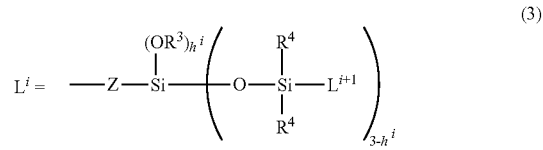

wherein
each $R^3$ independently represents a substituted or non-substituted, and linear or branched monovalent hydrocarbon group having 1 to 30 carbon atoms;
each $R^4$ independently represents an alkyl group having 1 to 6 carbon atoms or a phenyl group;
Z represents a divalent organic group;
i specifies a number of generations of said silylalkyl group, represented by $L^i$, in the case in which a number of generations of said silylalkyl group, which is a number of repetitions of said silylalkyl group, is k, i is an integer ranging from 1 to k, and a number of generations k is an integer ranging from 1 to 10;
$L^{i+1}$ is said silylalkyl group in the case of i<k, and $L^{i+1}$ is any $R^4$ in the case of i=k; and
$h^i$ is 0 or 1;
Q represents an organic group containing a sugar alcohol group; and
each of a, b, c and d is independently a number having the following range: $1.0 \leq a \leq 2.5$, $0 \leq b \leq 1.5$, $0.0001 \leq c \leq 1.5$, and $0.0001 \leq d \leq 1.5$.

2. The co-modified organopolysiloxane according to claim 1, wherein in said general formula (1), $R^1$ represents a substituted or non-substituted, and linear or branched monovalent hydrocarbon group having 1 to 8 carbon atoms, a polyoxyalkylene group represented by formula: —$R^5O(AO)_nR^6$ wherein n=1 to 100; AO represents an oxyalkylene group having 2 to 4 carbon atoms; $R^5$ represents a substituted or non-substituted, and linear or branched divalent hydrocarbon group having 3 to 5 carbon atoms; $R^6$ represents a hydrogen atom, a substituted or non-substituted, and linear or branched monovalent hydrocarbon group having 1 to 24 carbon atoms, or a substituted or non-substituted, and linear or branched acyl group having 2 to 24 carbon atoms; an alkoxy group, a hydroxyl group or a hydrogen atom, with the proviso that all $R^1$s do not represent a hydroxyl group, a hydrogen atom, said alkoxy group or said polyoxyalkylene group.

3. The co-modified organopolysiloxane according to claim 1, wherein in said general formula (1), Q is an organic group containing a sugar alcohol group represented by general formula (4-1):

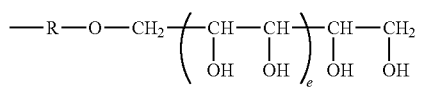
(4-1)

wherein R represents a divalent organic group; and e is 1 or 2, or represented by general formula (4-2):

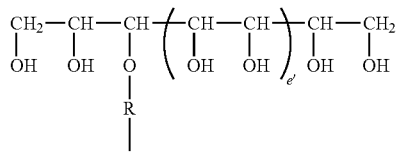
(4-2)

wherein R is the same as defined above; and e' is 0 or 1.

4. The co-modified organopolysiloxane according to claim 3, wherein in said general formula (4-1) or (4-2), R is a substituted or non-substituted, and linear or branched divalent hydrocarbon group having 3 to 5 carbon atoms.

5. The co-modified organopolysiloxane according to claim 1, wherein in said general formula (1), $L^1$ is a functional group represented by general formula (3-1):

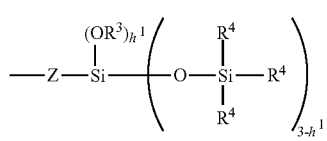
(3-1)

in the case of i=1, or represented by general formula (3-2):

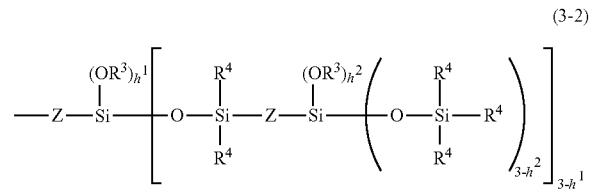
(3-2)

in the case of i=2, wherein $R^3$, $R^4$ and Z are the same as defined above; and each of $h^1$ and $h^2$ is independently 0 or 1.

6. The co-modified organopolysiloxane according to claim 1, which is represented by structural formula (1-1):

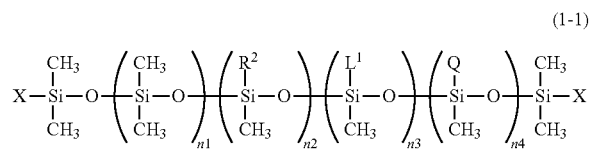
(1-1)

wherein $R^2$, $L^1$ and Q are the same as defined above;

each X independently is a group selected from the group consisting of a methyl group, $R^2$, $L^1$ and Q;

each of n1, n2, n3 and n4 is independently a number ranging from 0 to 2,000, and n1+n2+n3+n4 is a number ranging from 0 to 2,000, with the proviso that in the case of n3=0, at least one X is $L^1$, and in the case of n4=0, at least one X is Q.

7. The co-modified organopolysiloxane according to claim 1, which is represented by structural formula (1-1-1):

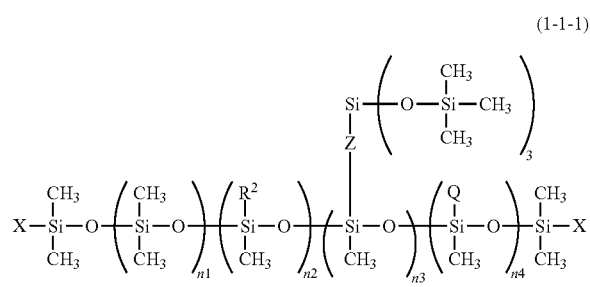
(1-1-1)

wherein $R^2$, Q, $L^1$ and Z are the same as defined above; each X independently is a group selected from the group consisting of a methyl group, $R^2$, $L^1$ and Q; each of n1, n2, n3 and n4 is independently a number ranging from 0 to 2,000, and n1+n2+n3+n4 is a number ranging from 0 to 2,000, with the proviso that in the case of n3=0, at least one X is $L^1$, and in the case of n4=0, at least one X is Q, or represented by structural formula (1-1-2):

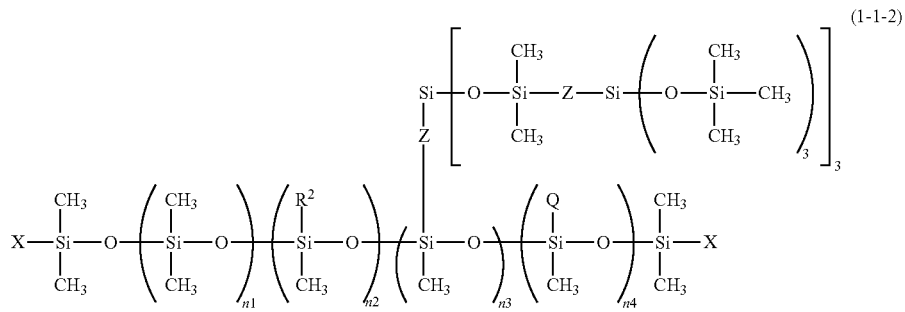

wherein $R^2$, Q, X, Z, n1, n2, n3, and n4 are the same as defined above.

8. The co-modified organopolysiloxane according to claim 7, wherein Z is independently a group selected from divalent organic groups represented by general formulae:

—$R^7$—

—$R^7$—CO—

—$R^7$—COO—$R^8$—

—CO—$R^7$—

—$R^7$—COO—$R^8$—

—$R^7$—CONH—$R^8$—

—$R^7$—$R^8$— wherein
each $R^7$ independently represents a substituted or non-substituted, and linear or branched, alkylene or alkenylene group having 2 to 22 carbon atoms or an arylene group having 6 to 22 carbon atoms;
each $R^8$ independently is a group selected from the group consisting of the following groups:

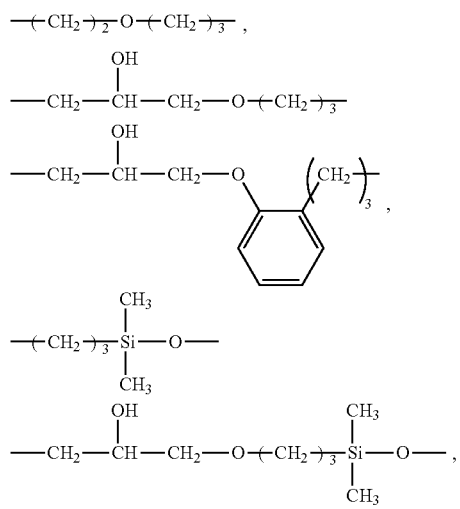

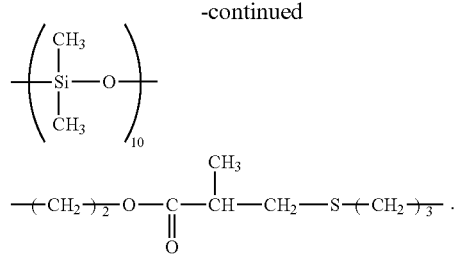

9. A surfactant comprising the co-modified organopolysiloxane according to claim 1.

10. An emulsion composition comprising:
(A) the co-modified organopolysiloxane according to claim 1;
(B) water; and
(C) at least one oil agent, wherein the oil agent is in the form of a liquid at 5 to 100° C., and is selected from the group consisting of a silicone oil, a non-polar organic compound and a low-polar organic compound.

11. A powder treatment agent comprising the co-modified organopolysiloxane according to claim 1.

12. The powder treatment agent according to claim 11, wherein the agent is a powder-surface treatment agent.

13. A powder surface-treated with the powder treatment agent according to claim 12.

14. A cosmetic raw material comprising: (A) the co-modified organopolysiloxane according to claim 1, and (D) powder.

15. The cosmetic raw material according to claim 14, further comprising (C) at least one oil agent, wherein the oil agent is in the form of a liquid at 5 to 100° C., and is selected from the group consisting of a silicone oil, a non-polar organic compound and a low-polar organic compound.

16. A thickening agent or a gelling agent comprising the co-modified organopolysiloxane according to claim 1.

17. A gel composition comprising: (A) the co-modified organopolysiloxane according to claim 1; and (C) at least one oil agent, wherein the oil agent is in the form of a liquid at 5 to 100° C., and is selected from the group consisting of a silicone oil, a non-polar organic compound and a low-polar organic compound.

18. A preparation for external use comprising the co-modified organopolysiloxane according to claim 1.

19. A preparation for external use comprising the emulsion composition according to claim 10.

20. A cosmetic comprising the powder according to claim 13.

21. A cosmetic comprising the cosmetic raw material according to claim 14.

22. A preparation for external use comprising the gel composition according to claim 17.

23. The preparation for external use according to claim 18, wherein the preparation is a cosmetic.

24. A method for producing the co-modified organopolysiloxane according to claim 1, comprising reacting, in the presence of a catalyst for a hydrosilylation reaction, (a) an organopolysiloxane having hydrogen atoms binding to silicon atoms, (b) an organic compound having one reactive unsaturated group in one molecule, (c) a siloxane dendron compound having one reactive unsaturated group in one molecule, and (d) a sugar alcohol-functional organic compound having one reactive unsaturated group in one molecule, to obtain the co-modified organopolysiloxane.

25. The method for producing the co-modified organopolysiloxane according to claim 24, further comprising reacting (e) a hydrocarbon compound having one reactive unsaturated group in one molecule or a linear organopolysiloxane having one reactive unsaturated group in one molecule.

26. The method for producing the co-modified organopolysiloxane according to claim 24, wherein said (c) siloxane dendron compound having one reactive unsaturated group in one molecule is a compound having a siloxane dendron structure having one carbon-carbon double bond at the terminal of the molecular chain, represented by general formula (3'):

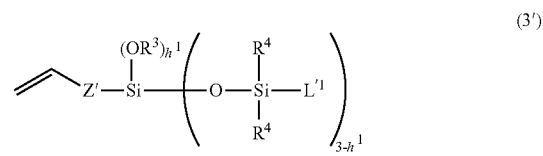

wherein
$R^3$ and $R^4$ are the same as defined above;
Z' represents a divalent organic group;
$h^1$ is 0 or 1;
$L^{'1}$ represents any $R^4$ or a silylalkyl group, in the case of j=1, represented by general formula (3"):

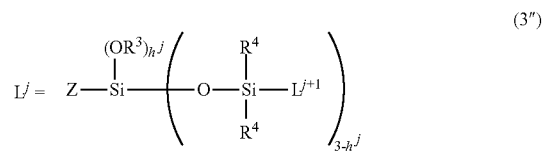

wherein $R^3$ and $R^4$ are the same as defined above;
Z represents a divalent organic group;
j specifies a number of generations of said silylalkyl group, represented by $L^j$, in the case in which a number of generations of said silylalkyl group, which is a number of repetitions of said silylalkyl group, is k', j is an integer ranging from 1 to k', and a number of generations k' is an integer ranging from 1 to 9;
$L^{j+1}$ is said silylalkyl group in the case of j<k', and $L^{j+1}$ is $R^4$ in the case of j=k'; and $h^j$ is 0 or 1.

* * * * *